United States Patent
Wu et al.

(10) Patent No.: US 10,377,747 B2
(45) Date of Patent: Aug. 13, 2019

(54) 2-ARYLAMINO PYRIDINE, PYRIMIDINE OR TRIAZINE DERIVATIVES, PREPARATION METHOD AND USE THEREOF

(71) Applicant: Wuxi Shuangliang Biotechnology Co., Ltd.

(72) Inventors: Jiaquan Wu, Jiangyin (CN); Haijun Zhang, Boxborough, MA (US); Huanyan Cao, Changzhou (CN); Shenshuang Jin, Wuxi (CN); Shuai Zhang, Wuxi (CN); Zhenghua Lu, Jiangyin (CN); Jian Dong, Jiangyin (CN); Chengchen Wang, Jiangyin (CN); Qiu Tan, Jiangyin (CN)

(73) Assignee: Wuxi Shuangliang Biotechnology Co., Ltd., Jiangsu (CN)

( * ) Notice: Subject to any disclaimer, the term of this patent is extended or adjusted under 35 U.S.C. 154(b) by 0 days.

(21) Appl. No.: 15/745,187

(22) PCT Filed: Aug. 31, 2015

(86) PCT No.: PCT/CN2015/088643
§ 371 (c)(1),
(2) Date: Jan. 16, 2018

(87) PCT Pub. No.: WO2017/035753
PCT Pub. Date: Mar. 9, 2017

(65) Prior Publication Data
US 2018/0208585 A1    Jul. 26, 2018

(51) Int. Cl.
| C07D 401/04 | (2006.01) |
| C07D 401/14 | (2006.01) |
| C07D 403/04 | (2006.01) |
| C07D 403/14 | (2006.01) |
| C07D 487/04 | (2006.01) |
| C07D 471/04 | (2006.01) |
| A61K 31/53 | (2006.01) |
| A61K 31/506 | (2006.01) |
| A61K 31/437 | (2006.01) |
| A61P 35/00 | (2006.01) |
| C07D 413/04 | (2006.01) |
| A61K 31/403 | (2006.01) |
| A61K 31/519 | (2006.01) |
| C07D 405/04 | (2006.01) |
| C07D 495/04 | (2006.01) |
| C07D 413/14 | (2006.01) |
| C07D 487/10 | (2006.01) |
| C07D 519/00 | (2006.01) |

(52) U.S. Cl.
CPC .......... *C07D 413/04* (2013.01); *A61K 31/403* (2013.01); *A61K 31/437* (2013.01); *A61K 31/506* (2013.01); *A61K 31/519* (2013.01); *A61P 35/00* (2018.01); *C07D 401/04* (2013.01); *C07D 403/04* (2013.01); *C07D 405/04* (2013.01); *C07D 413/14* (2013.01); *C07D 471/04* (2013.01); *C07D 487/10* (2013.01); *C07D 495/04* (2013.01); *C07D 519/00* (2013.01)

(58) Field of Classification Search
CPC .. C07D 487/04; C07D 403/04; C07D 403/14; C07D 401/04; C07D 401/14; A61K 31/4427; A61K 31/506; A61K 31/53; A61P 35/00
USPC ......... 544/212, 328, 331; 546/304; 514/245, 514/275, 256, 336, 349
See application file for complete search history.

(56) References Cited

FOREIGN PATENT DOCUMENTS

| AU | 2012288626 | 5/2013 | |
| AU | 2015222584 | 9/2015 | |
| CN | 103702990 | 4/2014 | |
| CN | 104761544 | 7/2015 | |
| CN | 104860941 | 8/2015 | |
| CN | 105175349 | 12/2015 | |
| JP | 2013544723 A | 12/2013 | |
| WO | 2013014448 A1 | 1/2013 | |
| WO | WO 2015/127873 | 9/2015 | |
| WO | WO 2015/188747 | 12/2015 | |
| WO | WO-2015188747 A1 * | 12/2015 | ............. A61K 31/53 |
| WO | WO 2016/070816 | 2/2016 | |

OTHER PUBLICATIONS

Cohen, "The Development and Therapeutic Potential of Protein Kinase Inhibitors", Current Opinion in Chemical Biology, 1999, pp. 459-465, vol. 3.*
Dermer, "Another Anniversary for the War on Cancer", Bio/Technology, 1994, p. 12, vol. 320.*
Doebele et al, "New Strategies to Overcome Limitations of Reversible EGFR Tyrosine Kinase Inhibitor Therapy in Non-Small Cell Lung Cancer", Lung Cancer, 2010, pp. 1-12, vol. 69.*

(Continued)

*Primary Examiner* — Venkataraman Balasubramanian
(74) *Attorney, Agent, or Firm* — Fish & Richardson P.C.

(57) ABSTRACT

The present disclosure relates to 2-arylamino pyridine, pyrimidine, or triazine derivatives, and the preparation method and use thereof. The 2-arylamino pyridine, pyrimidine, or triazine derivatives may act on certain mutated forms of epidermal growth factor receptor, for example the L858R activating mutant, the delE746_A750 mutant, the Exonl9 deletion activating mutant, and the T790M resistance mutant, so as to be used for treatment and prevention of diseases and medical conditions. The 2-arylamino pyridine, pyrimidine, or triazine derivatives may be used for treatment and prevention of cancer. The present disclosure also relates to a pharmaceutical composition comprising 2-arylamino pyridine, pyrimidine, or triazine derivatives, intermediates useful in the manufacture of 2-arylamino pyridine, pyrimidine, or triazine derivatives, and to methods of treatment of diseases mediated by various different forms of EGFR using 2-arylamino pyridine, pyrimidine, or triazine derivatives.

21 Claims, No Drawings

(56) References Cited

OTHER PUBLICATIONS

Bennet & Plum (edited by), Cecil Textbook of Medicine, 1996, W.B. Saunders Co., pp. 1004-1010, 20th edition, vol. 1.*
Pao et al., "Rational, Biologically Based Treatment of EGFR-mutant Non-small-cell Lung Cancer", Nature, 2010, pp. 760-774, vol. 10.*
Golub et al., "Molecular Classification of Cancer: Class Discovery and Class Prediction by Gene Expression Monitoring", Science, 1999, pp. 531-537, vol. 286.*
Remon et al., "Beyond EGFR TKI in EGFR-mutant Non-Small Cell Lung Cancer Patients: Main Challenges Still to be Overcome", Cancer Treatment Reviews, 2014, pp. 723-729, vol. 40.*
Fresheny, Culture of Animal Cells, A Manual of Basic Techniques, 1983, Alan R. Liss, Inc., New York, p. 4.*
WO 2015188747, Dec. 17, 2015; EPO Site English Machine Translation of Description.*
International Search Report of ISA/CN for PCT/CN2015/088643 (dated May 12, 2016).
M. Raymond Finlay, et al., "Discovery of a Potent and Selective EGFR Inhibitor (AZD9291) of Both Sensitizing and T790M Resistance Mutations that Spares the Wild Type Form of the Receptor", Journal of Medicinal Chemistry, 2014, pp. 8249-8267.
C.G. Wermuth, Chapter 13 Molecular Transformation Based on Isosteres, In The Practice of Medicinal Chemistry, TECHNOMICS INC, Japan, Aug. 15, 1998, vol. 1, pp. 235-271; and its English Abstract.

* cited by examiner

2-ARYLAMINO PYRIDINE, PYRIMIDINE OR TRIAZINE DERIVATIVES, PREPARATION METHOD AND USE THEREOF

TECHNICAL FIELD

The present disclosure pertains to the field of novel pharmaceutical technology, and in particular, the present disclosure relates to 2-arylamino pyridine, pyrimidine, or triazine derivatives, or pharmaceutically acceptable salts or solvates thereof which may be useful in the treatment or prevention of a certain disease or medical condition mediated through certain mutated forms of epidermal growth factor receptor (for example the L858R activating mutant, the delE746_A750 mutant, the Exonl9 deletion activating mutant and the T790M resistance mutant). Such compounds or salts or solvates thereof may be useful in the treatment or prevention of a number of different cancers. The present disclosure also relates to the preparation method of intermediates useful in the manufacture of said compounds.

BACKGROUND

Major treatments for cancer patients are radiotherapy, chemotherapy, and surgical therapy. Clinically, approximately 80% of lung cancers are non-small-cell lung cancer (NSCLC). According to the statistical data from American Cancer Society, about 200.000 new cases of NSCLC occur in America each year, wherein 65% or more are stage III and stage IV at the time of diagnosis. Except for some cases of stage III NSCLC which may be surgically removed after induction therapy, the majority of NSCLC cases need to be treated with chemotherapy. The treatment of late-stage non-small-cell lung cancer is still challenging. Only about 30% of limited-stage lesions may be cured by surgery. However, chemotherapeutic drugs have significant systemic toxic side effects, which cause considerable pain for patients. Thus, finding high effective and low toxic target therapeutic drugs has become an inevitable trend for anti-tumor drug development.

Epidermal growth factor receptor (EGFR) is a transmembrane protein tyrosine kinase member of the erbB receptor family. Upon binding of growth factor ligand (such as epidermal growth factor (EGF)), the receptor can homodimerise with another EGFR molecule or hetero-dimerise with another family member (such as erbB2 (HER2), erbB3 (HER3), or erbB4 (HER4)).

Homo- and/or hetero-dimerisation of erbB receptors results in the phosphorylation of key tyrosine residues in the intracellular domain, and leads to the stimulation of numerous intracellular signal transduction pathways involved in cell proliferation and survival. Deregulation of erbB family signaling promotes proliferation, invasion, metastasis, angiogenesis, and tumor cell survival, and has been described in many human cancers (including those of the lung, head and neck and breast). The erbB receptor family therefore represents a rational target for anticancer drug development. A number of drugs targeting EGFR are now available on the market, including Gefitinib(IRESSA™), Erlotinib(TARCEVA™), Lapatinib (TYKERB™, TYVERB™), etc. Detailed reviews of erbB receptor signaling and its involvement in tumourigenesis are provided in non-patent document 1 and 2.

Non-patent document 3 and 4 report that activating mutations in epidermal growth factor receptor correlated with response to Gefitinib therapy in non-small-cell lung cancer. The most common epidermal growth factor receptor activating mutations (L858R and delE746_A750) result in an increase in affinity for small molecule tyrosine kinase inhibitors (such as Gefitinib and Erlotinib) and a decrease in affinity for adenosine triphosphate (ATP) relative to wild type (WT) epidermal growth factor receptor. Ultimately, acquired resistance to therapy with Gefitinib and Erlotinib arises, for example by mutation of the gatekeeper residue T790M, which is reportedly detected in 50% of clinically resistant patients. This mutation is not believed to hinder the binding of Gefitinib or Erlotinib to EGFR sterically, merely to alter the affinity to ATP to levels comparable to wild type (WT) epidermal growth factor receptor.

In view of the importance of this mutation in resistance to existing therapies targeting EGFR, we believe that drugs which can inhibit EGFR harbouring the gatekeeper mutation are especially useful in the treatment of cancer.

There remains a need for compounds that may exhibit favorable potency profiles against WT EGFR versus activating mutant forms of EGFR (for example the L858R EGFR mutant, or the delE746_A750 mutant or the Exonl9 deletion EGFR) and/or resistant mutant forms of EGFR (for example T790M EGFR mutant), and/or selectivity over other enzyme receptors which may make the compounds especially promising for development as therapeutic drugs. In this regard, there remains a need for compounds that show a higher inhibition of binding to certain activating or resistance mutant forms of epidermal growth factor receptor while at the same time showing relatively low inhibition of WT EGFR. Due to low toxicology associated with WT EGFR inhibition, such compounds may be expected to be more suitable as therapeutic agents, particularly for the treatment of cancer. In order to overcome related resistance caused by the T790M mutant, a number of irreversible ATP competitive inhibitors (for example PF00299804, CI-1033, HKI-272, AZD9291, etc.) has entered stages of clinical study. The irreversible inhibitors comprise an acceptor fragment of Michael addition, which may form a covalent bond with a mercapto group of a conserved amino acid residue (Cys797) in the binding site. The ability of binding via an irreversible covalent bond between such inhibitor and EGFR is typically stronger than the binding ability between a reversible inhibitor and EGFR (Non-patent document 5). Even so, clinical trial results of these foresaid irreversible inhibitors demonstrate that these inhibitors still have certain limitations, such as toxic effects due to off-target effect, side effects caused by low selectivity, and inability to achieve a sufficient drug concentration in a patient. Therefore, developing novel irreversible EGFR inhibitors has great clinical significance and application prospect.

PRIOR ART DOCUMENT

Non-Patent Document

Non-patent document 1: New England Journal of Medicine, 2008, vol. 358, 1160-1174
Non-patent document 2: Biochemical and Biophysical Research Communications, 2004, vol. 319, 1-11
Non-patent document 3: Science, 2004, vol. 304, 1497-1500
Non-patent document 4: New England Journal of Medicine, 2004, vol. 350, 2129-2139
Non-patent document 5: Journal of Medicinal Chemistry, 2009, vol. 52, 1231-1236

SUMMARY

The present inventors designed and synthesized a series of 2-arylamino pyridine, pyrimidine, or triazine derivatives that are unreported in the literature, and conducted structural characterization. In addition, activity tests at cellular level were conducted on this series of compounds, which may showed high EGFR inhibitory activity while exhibited relatively low inhibitory activity for WT EGFR.

EGFR inhibitors of 2-arylamino pyridine, pyrimidine, or triazine derivative classes of the present disclosure may block the phosphorylation process of EGFR, and inhibit growth, proliferation, and differentiation of tumor cells. Thus, the inhibitors may be developed as new anti-tumor drugs.

The present disclosure is described as follows.

1. A compound represented by formula (I), or a pharmaceutically acceptable salt or a solvate thereof:

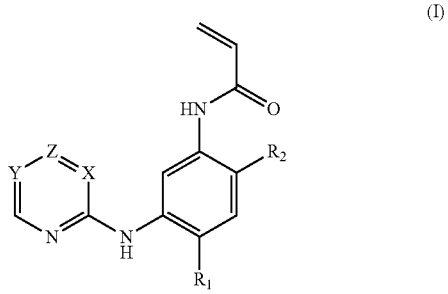

(I)

wherein X is selected from carbon, Y is selected from carbon, Z is selected from C—$R_a$, $R_1$ is selected from methoxy; or X is selected from nitrogen. Y is selected from carbon, Z is selected from C—$R_b$, $R_1$ is selected from methoxy or difluoromethoxy; or X is selected from nitrogen, Y is selected from nitrogen, Z is selected from C—$R_c$. $R_1$ is selected from methoxy or difluoromethoxy; or X is selected from nitrogen, Y is selected from nitrogen. Z is selected from C—$R_d$, $R_1$ is selected from difluoromethoxy;

$R_a$ is selected from 3-methyl-1H-indazol-1-yl, 1-methyl-1H-pyrrolo[2,3-b]pyridin-3-yl, 1-methyl-1H-thieno[3,2-c]pyrazol-3-yl, 1-methyl-1H-pyrazolo[4,3-b]pyridin-3-yl, pyrazolo[1,5-a]pyrimidin-3-yl or imidazo[1,2-a]pyridin-3-yl;

$R_b$ is selected from benzo[d]isoxazol-3-yl, 1-methyl-1H-pyrrolo[3,2-b]pyridin-3-yl, 2,4-dimethyl-4H-thieno[3,2-b]pyrrol-6-yl, 2,5,6-trimethyl-6H-thieno[2,3-b]pyrrol-4-yl or 1-methyl-1H-thieno[3,2-c]pyrazol-3-yl;

$R_c$ is selected from 1H-benzo[d]imidazol-1-yl, 1H-indol-7-yl or 1-methyl-1H-indol-7-yl;

$R_d$ is selected from 1-methyl-1H-pyrrolo[2,3-b]pyridin-3-yl;

$R_2$ is selected from (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl or 5-methyl-2,5-diazaspiro[3.4]oct-2-yl.

2. The compound according to item 1, or a pharmaceutically acceptable salt or a solvate thereof, which has a structure represented by formula (II),

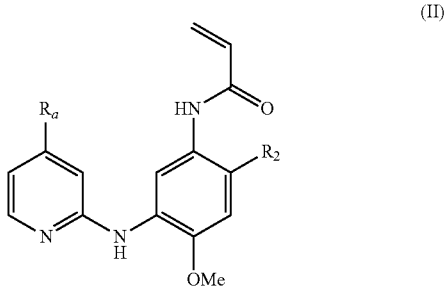

(II)

wherein $R_a$ is selected from 3-methyl-1H-indazol-1-yl, 1-methyl-1H-pyrrolo[2,3-b]pyridin-3-yl, 1-methyl-1H-thieno[3,2-c]pyrazol-3-yl, 1-methyl-1H-pyrazolo[4,3-b]pyridin-3-yl, pyrazolo[1,5-a]pyrimidin-3-yl or imidazo[1,2-a]pyridin-3-yl;

$R_2$ is selected from (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl or 5-methyl-2,5-diazaspiro[3.4]oct-2-yl.

3. The compound according to item 1, or a pharmaceutically acceptable salt or a solvate thereof, which has a structure represented by formula (III),

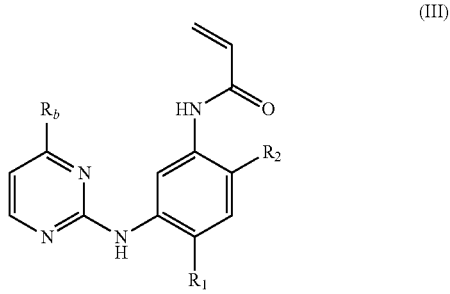

(III)

wherein $R_b$ is selected from benzo[d]isoxazol-3-yl, 1-methyl-1H-pyrrolo[3,2-b]pyridin-3-yl, 2,4-dimethyl-4H-thieno[3,2-b]pyrrol-6-yl, 2,5,6-trimethyl-6H-thieno[2,3-b]pyrrol-4-yl or 1-methyl-1H-thieno[3,2-c]pyrazol-3-yl;

$R_1$ is selected from methoxy or difluoromethoxy:

$R_2$ is selected from (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl or 5-methyl-2,5-diazaspiro[3.4]oct-2-yl.

4. The compound according to item 1, or a pharmaceutically acceptable salt or a solvate thereof, which has a structure represented by formula (IV),

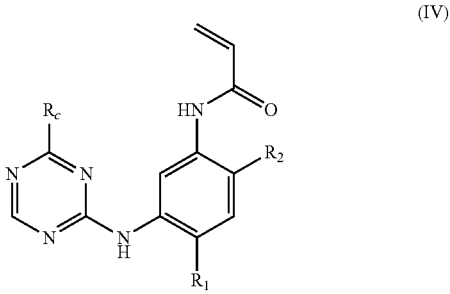

(IV)

wherein $R_c$ is selected from 1H-benzo[d]imidazol-1-yl, 1H-indol-7-yl or 1-methyl-1H-indol-7-yl:

$R_1$ is selected from methoxy or difluoromethoxy;

$R_2$ is selected from (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl or 5-methyl-2,5-diazaspiro[3.4]oct-2-yl.

5. The compound according to item 1, or a pharmaceutically acceptable salt or a solvate thereof, which has a structure represented by formula (V),

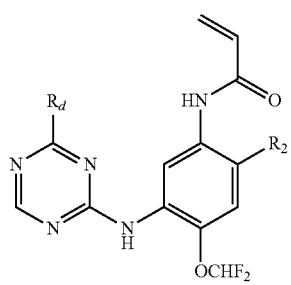

(V)

wherein $R_d$ is selected from 1-methyl-1H-pyrrolo[2,3-b]pyridin-3-yl;

$R_2$ is selected from (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl or 5-methyl-2,5-diazaspiro[3.4]oct-2-yl.

6. The compound according to item 3, or a pharmaceutically acceptable salt or a solvate thereof, wherein $R_b$ is selected from benzo[d]isoxazol-3-yl, 1-methyl-1H-pyrrolo[3,2-b]pyridin-3-yl or 1-methyl-1H-thieno[3,2-c]pyrazol-3-yl.

7. The compound according to item 4, or a pharmaceutically acceptable salt or a solvate thereof, wherein $R_c$ is 1H-indol-7-yl.

8. The compound according to any one of items 1-7, or a pharmaceutically acceptable salt or a solvate thereof, wherein $R_2$ is (2-(dimethylamino)ethyl)(methyl)amino.

9. The compound according to any one of item 1-5, or a pharmaceutically acceptable salt or a solvate thereof wherein the compound represented by the formula (I) is selected from any one of the following compounds: N-(5-((4-(benzo[d]isoxazol-3-yl)pyrimidin-2-yl)amino)-4-(difluoromethoxy)-2-((2-(dimethylamino)ethyl)(methyl)amino)phenyl)acrylamide, N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide, N-(4-(difluoromethoxy)-2-((2-(dimethylamino)ethyl)methyl)amino)-5-((4-(1-methyl-1H-pyrrolo[3,2-b]pyridin-3-yl)pyrimidin-2-yl)amino)phenyl)acrylamide, N-(4-(difluoromethoxy)-2-((2-(dimethylamino)ethyl)(methyl)amino)-5-(4-(1-methyl-1H-thieno[3,2-c]pyrrol-3-yl)pyrimidin-2-yl)amino)phenyl)acrylamide, N-(5-((4-(1H-indol-7-yl)-1,3,5-triazin-2-yl)amino)-4-(difluoromethoxy)-2-((2-(dimethylamino)ethyl)(methyl)amino)phenyl)acrylamide, N-(4-(difluoromethoxy)-2-((2-(dimethylamino)ethyl)(methyl)amino)-5-((4-(1-methyl-H-pyrrolo[2,3-b]pyridin-3-yl)-1,3,5-triazin-2-yl)amino)phenyl)acrylamide, N-(5-((4-(benzo[d]isoxazol-3-yl)pyrimidin-2-yl)amino)-2-((2-(diethylamino)ethyl)(methyl)amino)-4-methoxyphenyl)acrylamide, N-(2-((2-(dimethylamino)ethyl)(methyl)amino)-4-methoxy-5-((4-(1-methyl-1H-thieno[3,2-c]pyrrol-3-yl)pyrimidin-2-yl)amino)phenyl)crylamide, or N-(5-((4-(1H-indol-7-yl)-1,3,5-triazin-2-yl)amino)-2-((2-(dimethylamino)ethyl)(methyl)amino-4-methoxyphenyl)acrylamide.

10. The compound according to any one of items 1-9, or a pharmaceutically acceptable salt or a solvate thereof, which is used for treatment of cancer.

11. The compound according to item 10, or a pharmaceutically acceptable salt or a solvate thereof, the cancer includes non-small-cell lung cancer, breast cancer, neurogliocytoma, prostate cancer, ovarian cancer, head and neck squamous carcinoma, cervical cancer, esophageal cancer, liver cancer, renal cancer, pancreatic cancer, colorectal cancer, skin cancer, leukemia, lymphoma, gastric cancer, multiple myeloma or solid tumor.

12. A pharmaceutical composition comprising the compound according to any one of items 1-11, or a pharmaceutically acceptable salt or a solvate thereof, and a pharmaceutically acceptable diluent and/or carrier.

13. Use of the compound according to any one of items 1-11 or a pharmaceutically acceptable salt or a solvate thereof as a medicament.

14. Use of the compound according to any one of items 1-11 or a pharmaceutically acceptable salt or a solvate thereof in the preparation of a medicament for the treatment of cancer.

15. The use according to item 14, wherein the cancer includes non-small-cell lung cancer, breast cancer, neurogliocytoma, prostate cancer, ovarian cancer, head and neck squamous carcinoma, cervical cancer, esophageal cancer, liver cancer, renal cancer, pancreatic cancer, colorectal cancer, skin cancer, leukemia, lymphoma, gastric cancer, multiple myeloma or solid tumor.

16. A method for producing an anti-cancer effect in a warm-blooded animal, such as human being, in need of such treatment, which comprises administering to the animal an effective amount of the compound according to any one of items 1-11 or a pharmaceutically acceptable salt or a solvate thereof.

17. Use of the compound according to any one of items 1-11 or a pharmaceutically acceptable salt or a solvate thereof and an additional anti-tumor substance for the simultaneous, separate or sequential treatment of cancer.

18. A method for preparing the compound according to any one of items 1-11 or a pharmaceutically acceptable salt or a solvate thereof, which comprises:

in the presence of an organic solvent, making a compound represented by the following formula (VI) or a salt thereof react with a carboxylic acid or carboxylic acid derivatives,

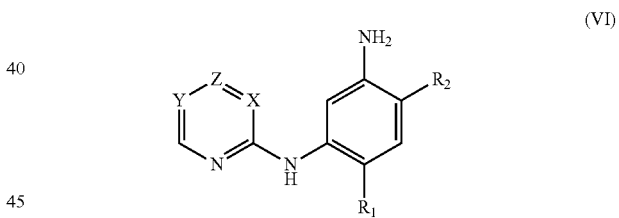

(VI)

wherein, in formula (VI), X, Y, Z, $R_1$, and $R_2$ have the same meaning as in the formula (I).

19. The method according to item 18, wherein the organic solvent includes dichloromethane, tetrahydrofuran. N,N-dimethylformamide, or N,N-dimethylacetamide.

20. The method according to item 18 or 19, wherein the carboxylic acid or carboxylic acid derivatives includes acrylic acid, acryloyl chloride or acrylic ester.

21. The method according to any one of items 18-20, wherein the compound represented by the formula (VI) is selected from any one of the following compounds: $N^4$-(4-(benzo[d]isoxazol-3-yl)pyrimidin-2-yl)-$N^1$-(2-(dimethylamino)ethyl)-5-methoxy-$N^1$-tolu ene-1,2,4-triamine, $N^4$-(4-(benzo[d]isoxazol-3-yl)pyrimidin-2-yl)-5-(difluoromethoxy)-$N^1$-(2-(dimethylamino)ethyl)-$N^1$-toluene-1,2,4-triamine, $N^1$-(2-(dimethylamino)ethyl)-5-methoxy-$N^1$-methyl-$N^4$-(4-(1-methyl-1H-pyrrolo[3,2-b]pyridin-3-yl)pyrimidin-2-yl)benzene-1,2,4-triamine, 5-(difluoromethoxy)-$N^1$-(2-(dimethylamino)ethyl)-$N^1$-methyl-$N^4$-(4-(1-methyl-1H-pyrrolo[3,2-b]pyridin-3-yl)pyrimidin-2-yl)benzene-1,2,4-triamine, $N^1$-(2-(dimethylamino)ethyl)-5-methoxy-$N^1$-methyl-$N^1$-(4-(1-methyl-1H-thieno[3,2-c]pyrazol-3-yl)pyrimidin-2-yl)benzene-1,2,4-triamine, 5-(difluoromethoxy)-$N^1$-(2-(dimethylamino)ethyl)-$N^1$-methyl-$N^4$-(4-(1-methyl-1H-thieno[3,2-c]pyrazol-3-yl)pyrimidin-2-yl)benzene-1,24-triamine, $N^4$-(4-(1H-indol-7-yl)-1,3,5-triazin-2-yl)-$N^1$-(2-(dimethylamino)ethyl)-5-methoxy-$N^1$-toluene-1,2,4-triamine, $N^4$-(4-(H-indol-7-yl)-1,3,5-triazin-2-yl)-5-(difluoromethoxy)-$N^1$-(2-(dimethylamino)ethyl)-$N^1$-toluene-1,2,4-triamine, or 5-(difluoromethoxy)-$N^1$-(2-(dimethylamino)ethyl)-$N^1$-methyl-$N^4$-(4-(1-methyl-1H-pyrrolo[2,3-b]pyridin-3-yl)-1,3,5-triazin-2-yl)benzene-1,2,4-triamine.

In the present disclosure, a suitable pharmaceutically acceptable salt of a compound represented by formula (I), formula (II), formula (II), formula (IV), or formula (V) is, for example, an acid-addition salt. For example, the acid-addition salt may be formed using an inorganic acid or organic acid. The acid-addition salt may be formed using an inorganic acid selected from hydrochloric acid, hydrobormic acid, sulphuric acid, or phosphoric acid. The acid-addition salt may be formed using an organic acid selected from trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid, or p-toluene-sulfonic acid.

In one embodiment, there is provided the mesylate salt of N-(5-((4-(benzo[d]isoxazol-3-yl)pyrimidin-2-yl)amino)-4-(difluoromethoxy)-2-((2-(dimethylamino)ethyl)(methyl)amino)phenyl)acrylamide.

In one embodiment, there is provided the mesylate salt of N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide.

In one embodiment, there is provided the mesylate salt of N-(4-(difluoromethoxy)-2-((2-(dimethylamino)ethyl)(methyl)amino)-5-((4-(1-methyl-1H-pyrrolo[3,2-b]pyridin-3-yl)pyrimidin-2-yl)amino)phenyl)acrylamide.

In one embodiment, there is provided the mesylate salt of N-(4-(difluoromethoxy)-2-((2-(dimethylamino)ethyl)(methy)amino)-5-((4-(1-methyl-1H-thien o[3,2-c]pyrrol-3-yl)pyrimidin-2-yl)amino)phenyl)acrylamide.

In one embodiment, there is provided the mesylate salt of N-(5-((4H-indol-7-yl))-1,3,5-triazin-2-yl)amino)-4-(difluoromethoxy)-2-((2-(dimethylamino)ethyl)(methyl)amino)phenyl)acrylamide.

In one embodiment, there is provided the mesylate salt of N-(4-(difluoromethoxy)-2-((2-(dimethylamino)ethyl)(methyl)amino)-5-((4-(1-methyl-1H-pyrrolo[2,3-b]pyridin-3-yl)-1,3,5-triazin-2-yl)amino)phenyl)acrylamide.

It will be understood that the compound represented by formula (I), formula (II), formula (III), formula (IV), or formula (V) or pharmaceutically acceptable salts thereof may exist in solvated forms and unsolvated forms. For example, the solvated form may be a hydrated form. It is to be understood that the present disclosure encompasses all such solvated and unsolvated forms.

The compound represented by formula (I), formula (II), formula (III), formula (IV), or formula (V) may be administered in the form of prodrug, which are broken down in the human or animal body to give a compound represented by formula (I), formula (II), formula (III), formula (IV), or formula (V). Examples of the prodrug include the in-vivo hydrolysable esters of the compound represented by formula (I), formula (II), formula (III), formula (IV), or formula (V). The in-vive hydrolysable esters can be formed by esterification of the hydroxyl group in the compound represented by formula (I), formula (II), formula (III), formula (IV), or formula (V). Various forms of prodrugs are known in the art. For examples of such prodrug derivatives, see:

(a) Design of Prodrugs, edited by H. Bundgaard (Elsevier, 1985) and Methods in Enzymology, Vol. 42, p. 309-396, edited by K. Wedder, et al. (Academic Press, 1985);

(b) A Textbook of Drug Design and Development, edited by Krogsgaard-Larsen and H. Bundgaard, Chapter 5: "Design and Application of Prodrugs", edited by H. Bundgaard, p. 113-191 (1991).

One aspect of the present disclosure provides the compounds represented by formula (I), formula (II), formula (III), formula (IV), or formula (V), which inhibit one or more activating or resistance mutations of EGFR, for example the L858R EGFR mutant, or the delE746_A750 mutant or the Exonl9 deletion EGFR and/or resistance mutant forms of EGFR (for example the T790M EGFR mutant). The compounds may be useful for the treatment of cancer in a patient who has developed, or may be at risk of developing a level of resistance to an existing therapy based on an EGFR inhibitor.

In one aspect of the present disclosure, there are provided the compounds represented by formula (I), formula (II), formula (III), formula (IV), or formula (V), which show a higher inhibition of activating or resistance mutant forms of EGFR than of WT EGFR. Due to reduction of toxicology associated with WT EGFR inhibition, such compounds are expected to be more suitable as therapeutic agents, particularly for the treatment of cancer. Such toxicologies are known to manifest themselves in human being as skin rashes and/or diarrhoea.

In another aspect, in the preparation method of the compound represented by formula (I), the compounds represented by formula (VI) may be prepared by deprotection of the corresponding amine compounds protected by amino groups. For examples of protecting groups, including protecting groups suitable for protecting nitrogen atoms, as well as means of formation and eventual deprotection, see T. W. Greene and P. G M. Wuts, "Protective Groups in Organic Synthesis", Second Edition, John Wiley & Sons, New York, 1991.

Another aspect of the present disclosure provides these other intermediates.

Therefore, another aspect of the present disclosure provides the compound represented by formula (VII), or a salt thereof:

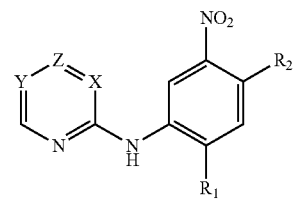

(VII)

wherein X is selected from carbon, Y is selected from carbon, Z is selected from C—$R_a$, $R_1$ is selected from methoxy; or X is selected from nitrogen, Y is selected from carbon, Z is selected from C—$R_b$, $R_1$ is selected from methoxy or difluoromethoxy; or X is selected from nitrogen, Y is selected from nitrogen, Z is selected from C—$R_c$, $R_1$ is selected from methoxy or difluoromethoxy; or X is selected from nitrogen. Y is selected from nitrogen, Z is selected from C—$R_d$, $R_1$ is selected from difluoromethoxy;

$R_a$ is selected from 3-methyl-1H-indazol-1-yl, 1-methyl-1H-pyrrolo[2,3-b]pyridin-3-yl, 1-methy-1H-thieno[3,2-c]pyrazol-3-yl, 1-methyl-1H-pyrazolo[4,3-b]pyridin-3-yl, pyrazolo[1,5-a]pyrimidin-3-yl or imidazo[1,2-a]pyridin-3-yl;

$R_b$ is selected from benzo[d]isoxazol-3-yl, 1-methyl-1H-pyrrolo[3,2-b]pyridin-3-yl, 2,4-dimethyl-4H-thieno[3,2-b]

pyrrol-6-yl, 2,5,6-trimethyl-6H-thieno[2,3-b]pyrrol-4-yl or 1-methyl-1H-thieno[3,2-c]pyrazol-3-yl;

$R_c$ is selected from 1H-benzo[d]imidazol-1-yl, 1H-indol-7-yl or 1-methyl-1H-indol-7-yl;

$R_d$ is selected from 1-methyl-1H-pyrrolo[2,3-b]pyridin-3-yl;

$R_2$ is selected from (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl or 5-methyl-2,5-diazaspiro[3.4]oct-2-yl.

Only parts of examples in the foresaid embodiments are given hereinbelow:

In one embodiment, there is provided intermediate compound 12a or a salt thereof.

Therefore, in this case, there is provided $N^1$-(4-(benzo[d]isoxazol-3-yl)pyrimidin-2-yl)-$N^4$-(2-(dimethylamino)ethyl)-2-methoxy-$N^4$-methyl-5-nitrobenzene-1,4-diamine, or a salt thereof.

In one embodiment, there is provided intermediate compound 19a or a salt thereof.

Therefore, in this case, there is provided $N^1$-(4-(benzo[d]isoxazol-3-yl)pyrimidin-2-yl)-2-(difluoromethoxy)-$N^4$-(2-(dimethylamino)ethyl)-$N^4$-methyl-5-nitrobenzene-1,4-diamine, or a salt thereof.

In one embodiment, there is provided intermediate compound 29a or a salt thereof.

Therefore, in this case, there is provided $N^1$-(2-(dimethylamino)ethyl)-5-methoxy-$N^1$-methyl-$N^4$-(4-(1-methyl-1H-pyrrolo[3,2-b]pyridin-3-yl)pyrimidin-2-yl)-2-nitrobenzene-1,4-diamine, or a salt thereof.

In one embodiment, there is provided intermediate compound 37a or a salt thereof.

Therefore, in this case, there is provided 2-(difluoromethoxy)-$N^4$-(2-(dimethylamino)ethyl)-$N^1$-methyl-$N^1$-(4-(1-methyl-1H-pyrrolo[3,2-b]pyridin-3-yl)pyrimidin-2-yl)-5-nitrobenzene-1,4-diamine, or a salt thereof.

In one embodiment, there is provided intermediate compound 49a or a salt thereof.

Therefore, in this case, there is provided $N^1$-(2-(dimethylamino)ethyl)-5-methoxy-$N^1$-methyl-$N^1$-(4-(1-methyl-1H-thieno[3,2-c]pyrazol-3-yl)pyrimidin-2-yl)-2-nitrobenzene-1,4-diamine, or a salt thereof.

In one embodiment, there is provided intermediate compound 49b or a salt thereof.

Therefore, in this case, there is provided 2-(difluoromethoxy)-$N^4$-(2-(dimethylamino)ethyl)-$N^4$-ethyl-$N^1$-(4-(1-ethyl-H-thieno[3,2-c]pyrazol-3-yl)pyrimidin-2-yl)-5-nitrobenzene-1,4-diamine, or a salt thereof.

In one embodiment, there is provided intermediate compound 78a or a salt thereof.

Therefore, in this case, there is provided $N^1$-(4-(1H-indol-7-yl)-1,3,5-triazin-2-yl)-$N^4$-(2-(dimethylamino)ethyl)-2-methyoxy-$N^4$-methyl-5-nitrobenzene-1,4-diamine, or a salt thereof.

In one embodiment, there is provided intermediate compound 78b or a salt thereof.

Therefore, in this case, there is provided $N^1$-(4-(1H-indol-7-yl)-1,3,5-triazin-2-yl)-2-(difluoromethoxy)-$N^4$-(2-(dimethylamino)ethyl)-$N^4$-methyl-5-nitrobenzene-1,4-diamine, or a salt thereof.

In one embodiment, there is provided intermediate compound 83 or a salt thereof.

Therefore, in this case, there is provided 2-(difluoromethoxy)-$N^1$-(2-(dimethylamino)ethyl)-$N^4$-methyl-$N^1$-(4-(1-methyl-1H-pyrrolo[2,3-b]pyridin-3-yl)-1,3,5-triazin-2-yl)-5-nitrobenzene-1,4-diamine, or a salt thereof.

In another aspect, in the pharmaceutical compositions of the present disclosure, there is no particular limitation with respect to pharmaceutically acceptable diluent and/or carrier, and currently known diluents and/or carriers may be used.

Dosage forms suitable for the following modes of administration may be applied for the pharmaceutical compositions of the present disclosure: oral use (for example, tablets, lozenges, hard or soft capsules, aqueous or oily suspensions, emulsions, dispersible powers or granules, or syrups, etc.); topical use (for example, creams, ointments, gels, or aqueous or oily solutions, or suspensions); administration by inhalation (for example, a finely divided powder or a liquid aerosol); administration by insufflation (for example, a finely divided powder) or parenteral administration (for example, a sterile aqueous or oily solution for intravenous, subcutaneous, intramuscular or intramuscular dosing or as a suppository for rectal dosing).

The pharmaceutical compositions of the present disclosure may be obtained by conventional procedures using conventional pharmaceutical expients, well known in the art. Thus, compositions intended for oral use may contain, for example, one or more colouring, sweetening, flavouring and/or preservative agents.

Though needs of each individual are different, those skilled in the art may determine the optimal dose for each active ingredient in the pharmaceutical compositions of the present disclosure. Normally, the compounds of the present disclosure or pharmaceutically acceptable salts or solvates thereof are orally administered to mammals daily. The administration dosage is about 0.0025 to 50 mg/kg body weight. However, preferably about 0.01 to 10 mg is orally administrated per kg body weight. The daily dosage will necessarily be varied depending upon the host treated, the particular route of administration, and the severity of the illness being treated.

The compounds or pharmaceutical compositions of the present disclosure may be used for treating various diseases mediated by epidermal growth factor receptor kinase (EGFR). The diseases mediated by EGFR are herein various cancers. The cancers include, but are not limited to, non-small-cell lung cancer, breast cancer, neurogliocytoma, prostate cancer, ovarian cancer, head and neck squamous carcinoma, cervical cancer, esophageal cancer, liver cancer, renal cancer, pancreatic cancer, colorectal cancer, skin cancer, leukemia, lymphoma, gastric cancer, multiple myeloma, or solid tumor.

It is to be understood that in the present disclosure, EGFR includes the wild type and various variants that may lead to diseases. These variants include, but are not limited to the variants comprising the following mutations: T790M, L858R, L861Q, or L858R/T790M. The present disclosure also includes truncated forms of EGFR that may lead to diseases. Thus, the compounds of the present disclosure or pharmaceutical compositions thereof may be used for treating various diseases mediated by EGFR wild type or various variants that may lead to diseases, including various cancers described above, or for inhibiting the biological activity of EGFR wild type or various variants that may lead to diseases.

DETAILED DESCRIPTION

Synthesis of EGFR Inhibitors

The present disclosure will be further illustrated by way of example in the following examples. Such examples are for illustrating the present disclosure only, but not for limiting the present disclosure in any way.

The synthesis route of compounds 14a-14e is as shown in scheme 1:

Scheme 1

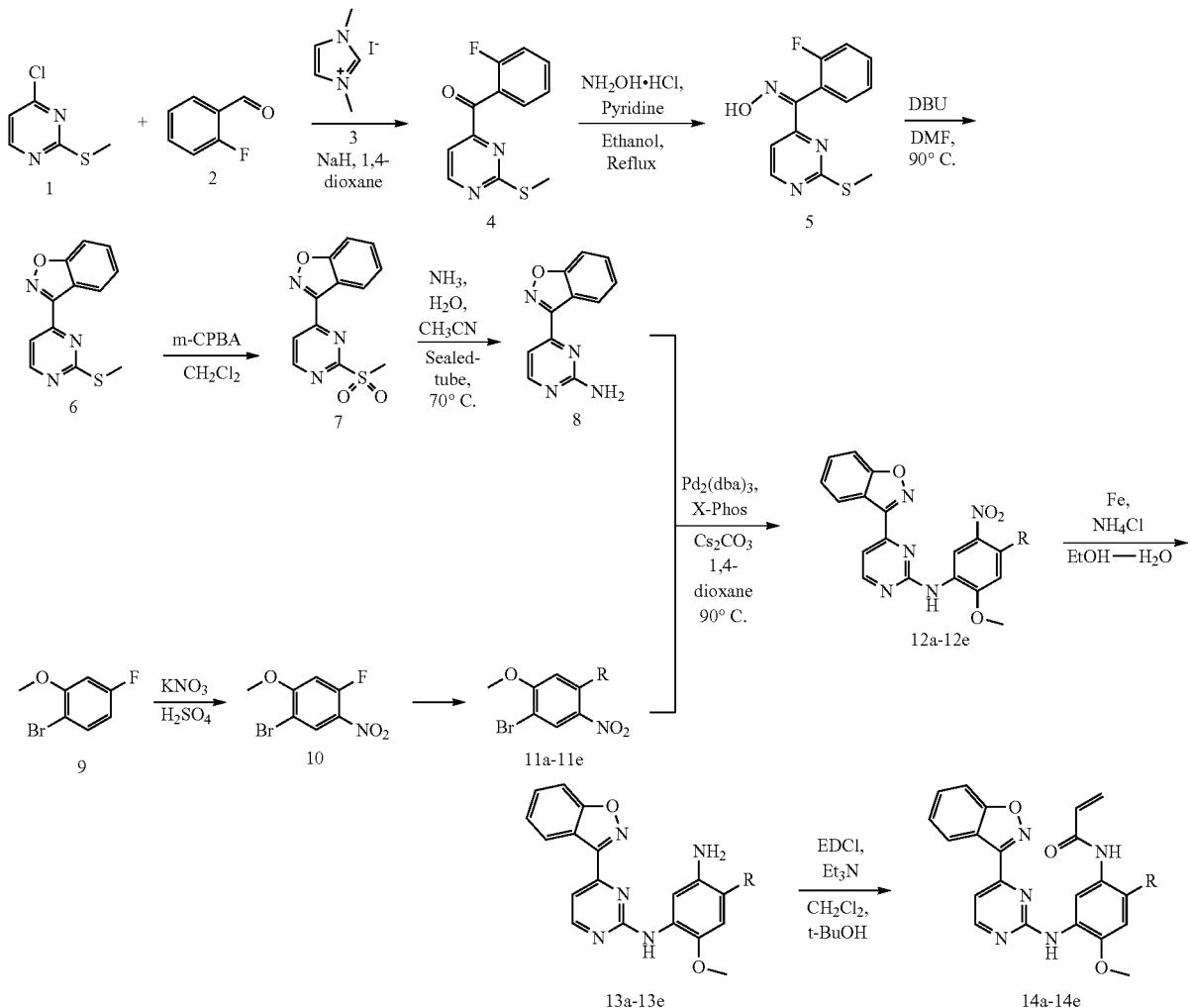

(2-fluorophenyl)(2-(methylthio)pyrimidin-4-yl)ketone (compound 4)

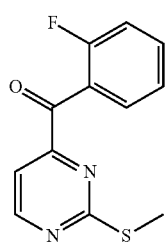 [SMILES: CSc1nccc(C(=O)c2ccccc2F)n1]

Compound 1 (51.84 g, 0.32 mol) was dissolved in 1,4-dioxane (600 mL), then compound 2 (48 g, 0.39 mol) and compound 3 (23.68 g, 0.11 mol) were added under stirring at room temperature, and NaH (60%) (15.36 g, 0.39 mol) was slowly added under cooling in an ice water bath After addition was completed, the ice water bath was removed. The reaction system was heated to reflux and react overnight. The reaction solution was cooled to room temperature, poured slowly into ice water, and extracted three times with ethyl acetate. The organic phase was washed once with saturated brine, dried over anhydrous sodium sulfate, filtered, spin-dried under reduced pressure, and subjected to column chromatography to obtain 41 g of compound 4 as a white solid. $^1$H NMR (400 MHz, CDCl$_3$): δ 8.80 (d, J=4.9 Hz, 1H), 7.77-7.75 (m, 1H), 7.65-7.57 (m, 1H), 7.53 (d, J=4.9 Hz, 1H), 7.34-7.29 (m, 1H), 7.20-7.12 (m, 1H), 2.47 (s, 3H).

(Z)-(2-fluorophenyl)(2-(methylthio)pyrimidin-4-yl)ethanone oxime (compound 5)

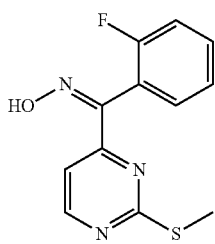 [SMILES: CSc1nccc(/C(=N\O)c2ccccc2F)n1]

Hydroxylamine hydrochloride (51.8 g, 0.75 mol) was added into anhydrous ethanol (700 mL). Pyridine (58.9 g, 0.75 mol) was added under stirring at room temperature, stirred for 5 min at room temperature, and then compound 4 (37 g, 0.15 mol) was added. The reaction system was heated to reflux and react overnight. The reaction solution was cooled to room temperature. Ethanol was evaporated under reduced pressure, and water and ethyl acetate were added into the residue and stirred. Liquid phases were separated, and the aqueous phase was further extracted once with ethyl acetate. The organic phases were combined, washed once with saturated brine, dried over anhydrous sodium sulfate, filtered, and evaporated under reduced pressure to obtain 54 g of yellow oily liquid compound 5, which was used directly in the next reaction. MS (ESI) (m/z): [M+H]$^+$ 264.0.

3-(2-(methylthio)pyrimidin-4-yl)benzo[d]isoxazole (compound 6)

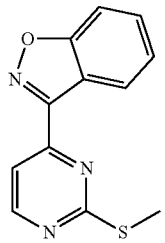

The crude product of compound 5 (54 g, 0.15 mol) was dissolved in DMF (500 mL), and DBU (40.2 g, 0.26 mol) was added at room temperature. The temperature was increased to 90° C. to react for 3 hours. The reaction solution was cooled to room temperature, poured slowly into ice water, stirred to precipitate solids, and filtered. The filter cake was washed twice with water, and dried to obtain 47 g of yellow solid. $^1$H NMR (400 MHz, CDCl$_3$): δ 8.71 (d, J=5.1 Hz, 1H), 8.54 (d, J=8.0 Hz, 1H), 7.88 (d, J=5.1 Hz, 1H), 7.71-7.63 (m, 2H), 7.52-7.42 (m, 1H), 2.74 (s, 3H); MS (ESI) (m/z): [M+H]$^+$ 244.0.

3-(2-(methylsulfonyl)pyrimidin-4-yl)benzo[d]isoxazole (compound 7)

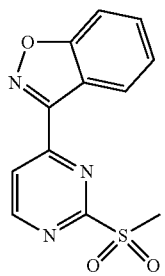 [SMILES: CS(=O)(=O)c1nccc(-c2noc3ccccc23)n1]

Compound 6 (24.3 g, 0.1 mol) was dissolved in dichloromethane (300 mL), and m-chloroperoxybenzoic acid (25.9 g, 0.15 mol) was added in batches under cooling in an ice water bath. After the completion of addition, the temperature was increased to room temperature to react overnight. Saturated sodium bicarbonate solution was added into the reaction solution, which was stirred for 10 min, and then the liquid phases were separated. The organic phase was washed once with saturated brine, dried over anhydrous sodium sulfate, filtered, and evaporated under reduced pressure to obtain 24 g of white solid, which was used directly in the next reaction. MS (ESI) (m/z): [M+H]$^+$ 276.0.

4-(benzo[d]isoxazol-3-yl)pyrimidin-2-amine (compound 8)

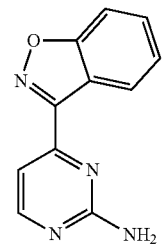 [SMILES: Nc1nccc(-c2noc3ccccc23)n1]

Compound 7 (12 g, 0.044 mol) was added into a 250 mL sealed-tube reactor, and acetonitrile (100 mL) and ammonia water (30 mL) were added. The temperature was increased to 70° C. to react overnight. The reaction solution was cooled, and filtered to obtain 6 g of white solid. $^1$H NMR (400 MHz, CDCl$_3$): δ 8.52-8.50 (m, 2H), 7.70-7.62 (m, 2H), 7.53 (d, J=5.1 Hz, 1H), 7.46-7.42 (m, 1H), 5.30 (s, 2H); MS (ESI) (m/z): [M+H]$^+$ 213.1.

1-bromo-4-fluoro-2-methoxy-5-nitrobenzene (compound 10)

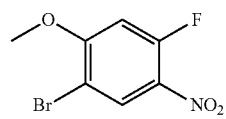

Compound 9 (15 g, 0.073 mol) was dissolved in concentrated sulfuric acid (150 mL), and potassium nitrate (7.4 g, 0.073 mol) was slowly added under cooling in an ice-salt bath. After the completion of addition, the temperature was increased to room temperature to react for 1 h. The reaction solution was poured slowly into ice water, stirred to precipitate solids, and filtered. The filter cake was washed twice with water, and oven-dried to obtain 13.2 g of grey solid. MS (ESI) (m/z): [M+H]$^+$ 250.9.

N$^1$-(4-bromo-5-methoxy-2-nitrophenyl)-N$^1$,N$^2$,N$^2$-trimethylethane-1,2-diamine (compound 11a)

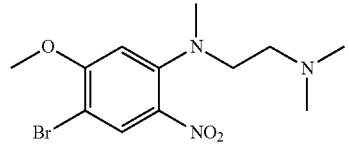

Compound 10 (15 g, 0.06 mol) was dissolved in acetonitrile (150 mL), and N,N,N'-trimethylethylenediamine (6.74 g, 0.066 mol) and potassium carbonate (16.56 g, 0.12 mol) were added. The reaction system was heated to reflux and react overnight. The reaction solution was cooled to room temperature and filtered. The filter cake was washed twice with dichloromethane. The filtrates were combined, evaporated under reduced pressure, and subjected to column chromatography to obtain 15 g of yellow oily liquid. $^1$H NMR (400 MHz, CDCl$_3$): δ 8.10 (s, 1H), 6.62 (s, 1H), 3.94 (s, 3H), 3.33 (t, J=6.9 Hz, 2H), 2.89 (s, 3H), 2.57 (t. J=6.9 Hz, 2H), 2.26 (s, 6H); MS (ESI) (m/z): [M+H]$^+$ 332.1.

N$^1$-(4-(benzo[d]isoxazol-3-yl)pyrimidin-2-yl)-N$^4$-(2-(dimethylamino)ethyl)-2 methoxy-methyl-5-nitrobenzene-1,4-diamine (compound 12a)

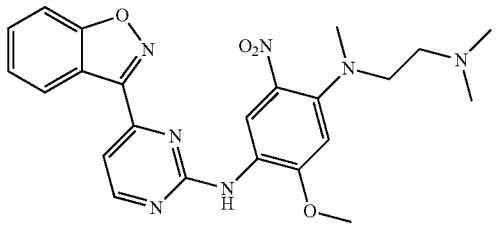 [SMILES: COc1cc(N(C)CCN(C)C)c([N+](=O)[O-])cc1Nc1nccc(-c2noc3ccccc23)n1]

Compound 8 (100 mg, 0.47 mmol) was dissolved in toluene (10 mL), and compound 11a (236 mg, 0.71 mmol), potassium tert-butoxide (162 mg, 1.44 mmol), 2-dicyclohexylphosphino-2,4,6-triisopropylbiphenyl (X-Phos) (448 mg 0.94 mmol), and tris(dibenzylideneacetone)dipalladium (431 mg, 0.47 mmol) were added. After the air was replaced with nitrogen for three times, the temperature was raised to 90° C. to react overnight. The reaction solution was cooled to room temperature and filtered. The filter cake was washed twice with dichloromethane. The filtrates were combined, evaporated under reduced pressure, and subjected to column chromatography to obtain 60 mg of yellow power. $^1$H NMR (400 MHz, CDCl$_3$): δ 9.04 (s, 1H), 8.61 (d, J=4.7 Hz, 1H), 8.52 (d, J=7.6 Hz, 1H), 7.70-7.63 (m, 4H), 7.51-7.47 (m, 1H), 6.76 (s, 1H), 4.02 (s, 3H), 3.37 (m, 2H), 2.91 (s, 3H), 2.69 (m, 2H), 2.36 (s, 6H); MS (ESI) (m/z): [M+H]$^+$ 464.2.

N$^4$-(4-(4-(benzo[d]isoxazol-3-yl)pyrimidin-2-yl)-N$^1$-(2-(dimethylamino)ethyl)-5-methoxy-N$^1$-toluene-1,2,4-triamine (compound 13a)

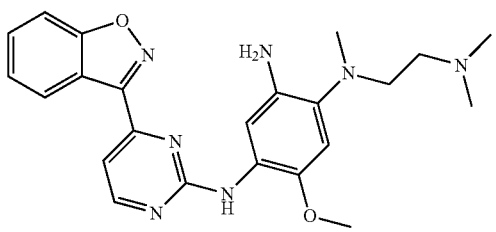

Compound 12a (60 mg, 0.13 mmol) was dissolved in ethanol (9 mL) and water (3 mL), and reduced iron power (43 mg, 0.77 mmol) and ammonium chloride (5 mg, 0.09 mmol) were added. The reaction system was heated to reflux and reacted for 2 h. The reaction solution was cooled to room temperature and filtered. The filtrate was adjusted to alkaline with saturated potassium carbonate, and extracted twice with dichloromethane. The organic phases were combined, washed once with saturated brine, dried over anhydrous sodium sulfate, filtered, evaporated under reduced pressure, and scraped to obtain 40 mg of yellow power. MS (ESI) (m/z): [M+H]$^+$ 434.2.

Example 1: N-(5-(4-(benzo[d]isoxazol-3-yl)pyrimidin-2-yl)amino)-4-(difluoromethoxy)-2-((2-(dimethylamino)ethyl)methyl)amino)phenyl)acrylamide (compound 14a)

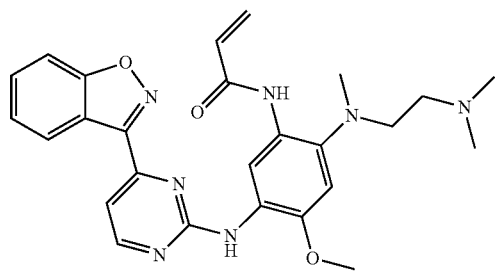 [SMILES: C=CC(=O)Nc1cc(Nc2nccc(-c3noc4ccccc34)n2)c(OC)cc1N(C)CCN(C)C]

Compound 13a (40 mg, 0.14 mmol) was dissolved in dichloromethane (10 mL) and tert-butanol (1 mL), and 1-(3-dimethylaminopropyl)-3-ethylcarbodiimide hydrochloride (EDCI, 35 mg, 0.28 mmol), triethylamine (19 mg, 0.28 mmol), and acrylic acid (13 mg, 0.28 mmol) were added under cooling in an ice-salt bath. After addition was complete, the temperature was increased to room temperature to react for 2 h. Saturated potassium carbonate solution was added into the reaction solution, stirred for 10 min, and the liquid phases were separated. The organic phase was dried, evaporated, and purified by preparative chromatography to obtain 8 mg of light yellow solid. $^1$H NMR (400 MHz, CDCl$_3$): δ 10.23 (s, 1H), 9.50 (s, 1H), 8.69 (d, J=5.0 Hz, 1H), 8.57 (d, J=8.0 Hz, 1H), 7.68-7.57 (m, 4H), 7.38-7.29 (m, 1H), 6.85 (s, 1H), 6.45-6.28 (m, 2H), 5.71 (m, 1H), 3.93 (s, 3H), 2.96-2.88 (m, 2H), 2.75 (s, 3H), 2.39-2.28 (m, 8H); MS (ESI) (m/z): [M+H]$^+$ 488.2.

1-(4-bromo-5-methoxy-2-nitrophenyl)-4-methylpiperazine (compound 11 b)

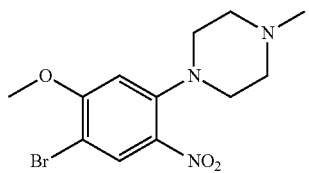

Compound 11b was prepared in the same manner as compound 11a, except that 4-methylpiperazine was used instead of N,N,N'-trimethylethylenediamine. $^1$H NMR (400 MHz, CDCl$_3$): δ 8.23 (s, 1H), 6.52 (s, 1H), 3.98 (s, 3H), 3.20-3.10 (m, 4H), 2.69-2.59 (m, 4H), 2.40 (s, 3H); MS (ESI) (m/z): [M+H]$^+$ 330.0.

4-(benzo[d]isoxazol-3-yl)-N-(2-methoxy-4-(4-methylpiperazin-1-yl)-5-nitrophenyl)pyrimidine-2-amine (compound 12b)

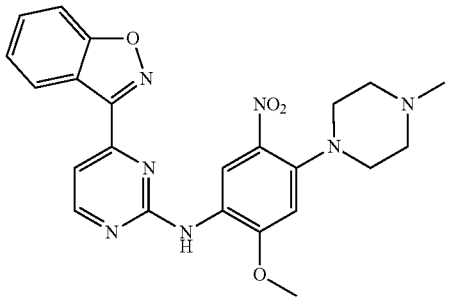

Compound 8 (200 mg, 0.94 mmol) was dissolved in 1,4-dioxane (10 mL), and compound 11b (311 mg, 0.94 mmol), cesium carbonate (1.23 g, 3.77 mmol), 2-dicyclohexylphosphino-2,4,6-triisopropylbiphenyl (X-Phos) (270 mg, 0.57 mmol), and tris(dibenzylideneacetoue)dipalladium (173 mg, 0.19 mmol) were added. After the air was replaced with nitrogen for three times, the temperature was increased to 90° C. to react overnight. The reaction solution is cooled to room temperature and filtered. The filter cake was washed twice with dichloromethane. The filtrates were combined, evaporated under reduced pressure, and subjected to column chromatography to obtain 180 mg of red oily liquid. MS (ESI) (m/z): [M+H]$^+$ 462.2.

$N^1$-(4-(benzo[d]isoxazol-3-yl)pyrimidin-2-yl)-6-methoxy-4-(4-methylpiperazin-1-yl)benzene-1,3-diamine (compound 13b)

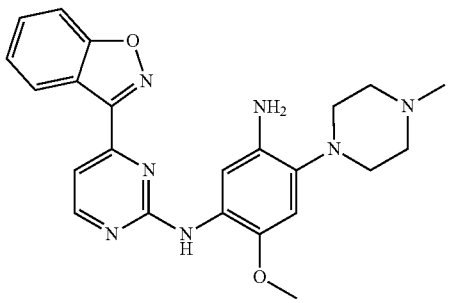 [SMILES: COc1cc(N2CCN(C)CC2)c([N+](=O)[O-])cc1Nc1nccc(-c2noc3ccccc23)n1]

Compound 13b was prepared in the same manner as compound 13a, except that compound 12b was used instead of compound 12a. MS (ESI) (m/z): [M+H]$^+$ 432.2.

Example 2: N-(5-(((4-(benzo[d]isoxazol-3-yl)pyrimidin-2-yl)amino)-4-methoxy-2-(4-methylpiperazin-1-yl)phenyl)acrylamide (compound 14b)

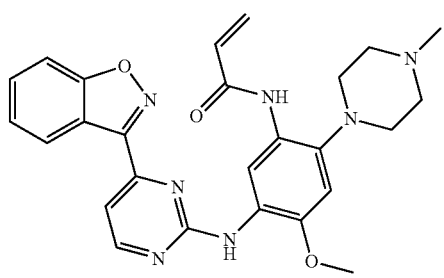 [SMILES: C=CC(=O)Nc1cc(Nc2nccc(-c3noc4ccccc34)n2)c(OC)cc1N1CCN(C)CC1]

Compound 14b was prepared in the same manner as compound 14a, except that compound 13b was used instead of compound 13a. $^1$H NMR (400 MHz, CDCl$_3$): δ 9.45 (s, 1H), 8.68 (d, J=5.0 Hz, 1H), 8.56-8.54 (m, 2H), 7.68-7.58 (m, 4H), 7.39-7.35 (m, 1H), 6.85 (s, 1H), 6.44-6.23 (m, 2H), 5.78 (d, J=9.1 Hz, 1H), 3.93 (s, 3H), 2.99-2.98 (m, 4H), 2.69 (m, 4H), 2.45 (s, 3H); MS (ESI) (m/z): [M+H]$^+$ 486.2.

1-(4-bromo-5-methoxy-2-nitrophenyl)-N,N-dimethylpiperidin-4-amine (compound 11c)

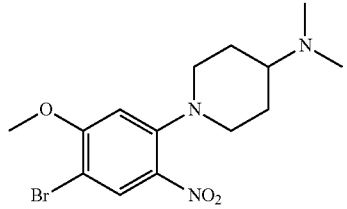

Compound 11c was prepared in the same manner as compound 11a, except that N,N-dimethylpiperidin-4-amine was used instead of N,N,N'-trimethylethylenediamine. $^1$H NMR (400 MHz, CDCl$_3$) δ 8.22 (s, 1H), 6.51 (s, 1H), 3.97 (s, 3H), 3.38 (d, J=12.4 Hz, 2H), 2.93-2.87 (m, 2H), 2.45-2.31 (m, 7H), 1.95-1.92 (m, 2H), 1.84-1.74 (m, 2H); MS (ESI) (m/z): [M+H]$^+$ 358.1.

4-(benzo[d]isoxazol-3-yl)-N-(4-(4-(dimethylamino)piperidin-1-yl)-2-methoxy-5-nitrophenyl)pyrimidine-2-amine (compound 12c)

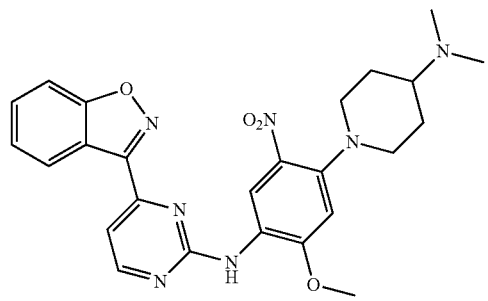 [SMILES: COc1cc(N2CCC(N(C)C)CC2)c([N+](=O)[O-])cc1Nc1nccc(-c2noc3ccccc23)n1]

Compound 12c was prepared in the same manner as compound 12a, except that compound 11c was used instead of compound 11a. $^1$H NMR (400 MHz, CDCl$_3$): δ 9.18 (s, 1H), 8.66 (d, J=5.1 Hz, 1H), 8.55 (d, J=7.7 Hz, 1H), 7.78-7.63 (m, 4H), 7.55-7.50 (m, 1H), 6.67 (s, 1H), 4.05 (s, 3H), 3.42-3.36 (m, 2H), 2.94-2.78 (m, 2H), 2.37-2.35 (m, 7H), 1.96-1.83 (m, 4H); MS (ESI) (m/z): [M+H]$^+$ 490.2.

$N^1$-(4-(benzo[d]isoxazol-3-yl)pyrimidin-2-yl)-4-(4-(dimethylamino)piperidin-1-yl)-6-methoxyphenyl-1,3-diamine (compound 13c)

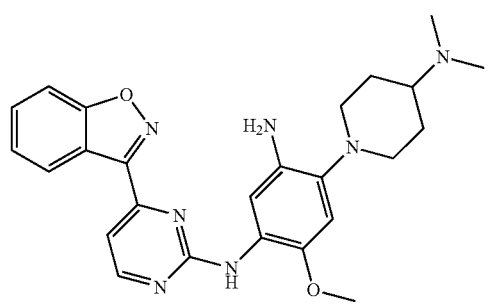 [SMILES: COc1cc(N2CCC(N(C)C)CC2)c(N)cc1Nc1nccc(-c2noc3ccccc23)n1]

Compound 13c was prepared in the same manner as compound 13a, except that compound 12c was used instead of compound 12a. MS (ESI) (m/z): [M+H]+ 460.2.

Example 3: N-(5-((4-(benzo[d]isoxazol-3-yl)pyrimidin-2-yl)amino)-2-(4-(dimethylamino)piperidin-1-yl)-4-methoxyphenyl)acrylamide (compound 14c)

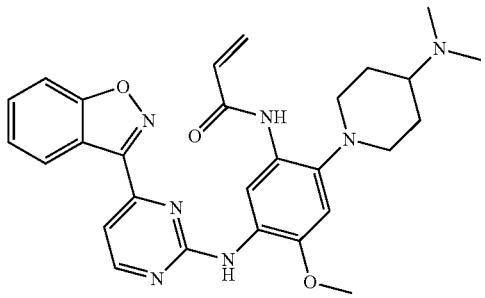 [SMILES: C=CC(=O)Nc1cc(Nc2nccc(-c3noc4ccccc34)n2)c(OC)cc1N1CCC(N(C)C)CC1]

Compound 14c was prepared in the same manner as compound 14a, except that compound 13c was used instead of compound 13a. $^1$H NMR (400 MHz, CDCl$_3$): δ 9.39 (s, 1H), 8.65 (d, J=5.0 Hz, 1H), 8.52 (d, J=7.9 Hz, 1H), 8.41 (s, 1H), 7.75-7.53 (nm, 4H), 7.36 (t, J=7.4 Hz, 1H), 6.76 (s, 1H), 6.37-6.36 (m, 2H), 5.78-5.77 (m, 1H), 3.92 (s, 3H), 3.18-3.15 (m, 2H), 2.81-2.76 (m, 3H), 2.67 (s, 6H), 2.25-2.22 (m, 2H), 1.98-1.96 (m, 2H); MS (ESI) (m/z): [M+H]+ 514.3.

(S)-1-(1-(4-bromo-5-methoxy-2-nitrophenyl)pyrrolidin-2-yl)-N,N-dimethylmethanamine

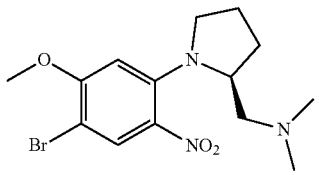

Compound 11d was prepared in the same manner as compound 11a, except that (S)—N,N-dimethyl-1-(pyrrolidin-2-yl)-methanamine was used instead of N,N,N'-trimethylethylenediamine. $^1$H NMR (400 MHz, CDCl$_3$): δ 8.12 (s, 1H), 6.71 (s, 1H), 3.95 (s, 3H), 3.62-3.55 (m, 1H), 2.72-2.61 (m, 2H), 2.49-2.23 (m, 8H), 2.09-1.71 (m, 4H); MS (ESI) (m/z): [M+H]+ 359.1.

(S)-4-(benzo[d]isoxazol-3-yl)-N-(4-(2-((dimethylamino)methyl)pyrrolidin-1-yl)-2-methoxy-5-nitrophenyl)pyrimidine-2-amine (compound 12d)

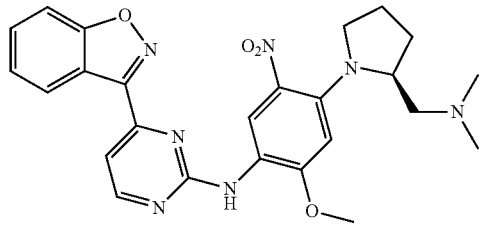 [SMILES: COc1cc(N2CCC[C@H]2CN(C)C)c([N+](=O)[O-])cc1Nc1nccc(-c2noc3ccccc23)n1]

Compound 12d was prepared in the same manner as compound 12a, except that compound 11d was used instead of compound 11a. MS (ESI) (m/z): [M+H]+ 490.2.

(S)—N$_1$-(4-(benzo[d]isoxazol-3-yl)pyrimidin-2-yl)-4-(2-((dimethylamino)methyl)pyrrolidin-1-yl)-6-methoxyphenyl-1,3-diamine (compound 13d)

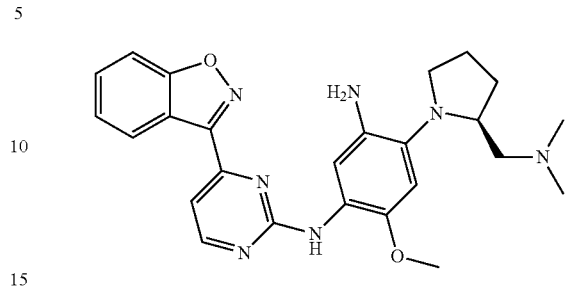

Compound 13d was prepared in the same manner as compound 13a, except that compound 12d was used instead of compound 12a. MS (ESI) (m/z): [M+H]+ 460.2.

Example 4: (S)—N-(5-((4-(benzo[d]isoxazol-3-yl)pyrimidin-2-yl)amino)-2-(2-((dimethylamino)methyl)pyrrolidin-1-yl)-4-methoxyphenyl)acrylamide (compound 14d)

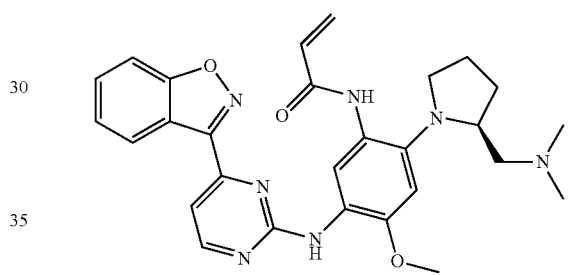

Compound 14d was prepared in the same manner as compound 14a, except that compound 13d was used instead of compound 13a. $^1$H NMR (400 MHz, CDCl$_3$): δ 12.02 (s, 1H), 9.55 (s, 1H), 9.29 (s, 1H), 8.66 (d, J=5.0 Hz, 1H), 8.54 (d, J=8.0 Hz, 1H), 7.73-7.53 (m, 4H), 7.45 (m, 1H) 6.72 (s, 1H), 6.37 (d, J=16.1 Hz, 1H), 5.72 (d, J=11.4 Hz, 1H), 3.94 (s, 3H), 2.97 (m, 1H), 2.83-2.20 (m, 8H), 2.13-1.60 (m, 4H); MS (ESI) (m/z): [M+H]+ 514.3.

2-(4-bromo-5-methoxy-2-nitrophenyl)-5-methyl-2,5-diazaspiro[3.4]octane (compound 11e)

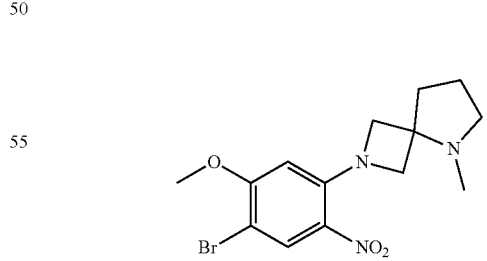

Compound 11e was prepared in the same manner as compound 11a, except that 5-methyl-2,5-diazaspiro[3.4]octane was used instead of N,N,N'-trimethylethylenediamine. $^1$H NMR (400 MHz, CDCl$_3$): δ 8.16 (s, 1H), 5.97 (s, 1H), 4.15 (d, J=9.2 Hz, 2H), 3.96 (s, 3H), 3.75 (d, J=9.2 Hz, 2H), 2.77 (t, J=7.2 Hz, 2H), 2.50 (s, 3H), 2.15-2.11 (m, 2H), 1.88-1.75 (m, 2H); MS (ESI) (m/z): [M+H]+ 357.1.

4-(benzo[d]isoxazol-3-yl)-N-(2-methoxy-4-(5-methyl-2,5-diazaspiro[3.4]oct-2-yl)-5-nitrophenyl)pyrimidine-2-amine (compound 12e)

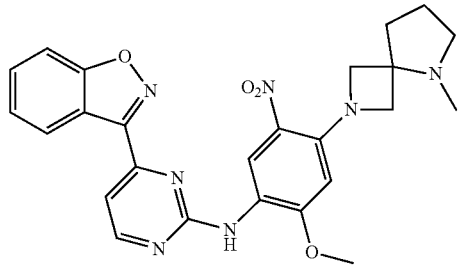

Compound 12e was prepared in the same manner as compound 12a, except that compound 11e was used instead of compound 11a. MS (ESI) (m/z): [M+H]$^+$ 488.2.

$N^1$-(4-(benzo[d]isoxazol-3-yl)pyrimidin-2-yl)-6-methoxy-4-(5-methyl-2,5-diazaspiro[3.4]oct-2-yl)benzene-1,3-diamine (compound 13e)

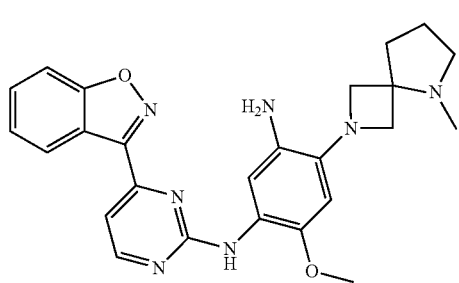 [SMILES: COc1cc(N2CC3(CCCN3C)C2)c([N+](=O)[O-])cc1Nc1nccc(-c2noc3ccccc23)n1]

Compound 13e was prepared in the same manner as compound 13a, except that compound 12e was used instead of compound 12a. MS (ESI) (m/z): [M+H]$^+$ 458.2.

Example 5: N-(5-((4-(benzo[d]isoxazol-3-yl)pyrimidin-2-yl)amino)-4-methoxy-2-(5-methyl-2,5-diazaspiro[3.4]oct-2-yl)phenyl)acrylamide (compound 14e)

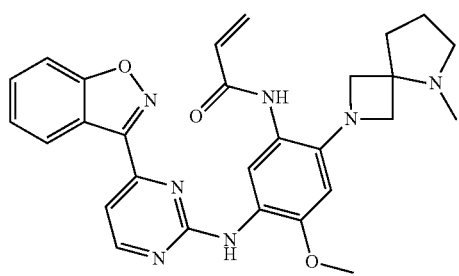 [SMILES: C=CC(=O)Nc1cc(Nc2nccc(-c3noc4ccccc34)n2)c(OC)cc1N1CC2(CCCN2C)C1]

Compound 14e was prepared in the same manner as compound 14a, except that compound 13e was used instead of compound 13a. $^1$H NMR (400 MHz, CDCl$_3$): δ 8.58 (d, J=5.0 Hz, 1H), 8.55-8.23 (m, 2H), 7.72-7.51 (m, 4H), 7.48-7.38 (m, 1H), 7.18-6.91 (m, 1H), 6.53-6.14 (m, 3H), 5.78-5.64 (m, 1H), 4.10-4.06 (m, 2H), 3.98-3.95 (m, 3H), 3.77-3.71 (m, 2H), 2.93-2.76 (m, 2H), 2.60-2.52 (m, 3H), 2.28-2.12 (m, 2H), 1.89-1.84 (m, 2H); MS (ESI) (m/z): [M+H]$^+$ 512.2.

The synthesis route of compounds 21a-21f is as shown in scheme 2:

Scheme 2

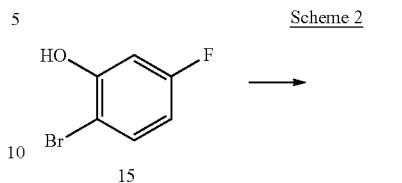

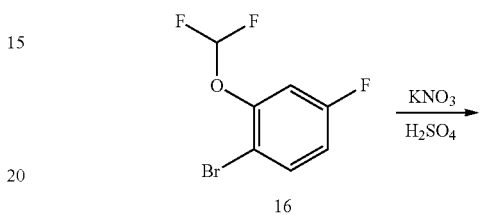

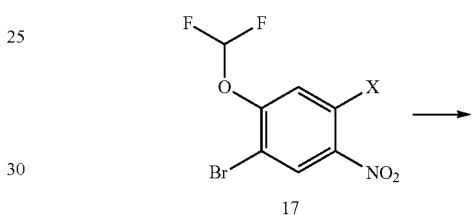

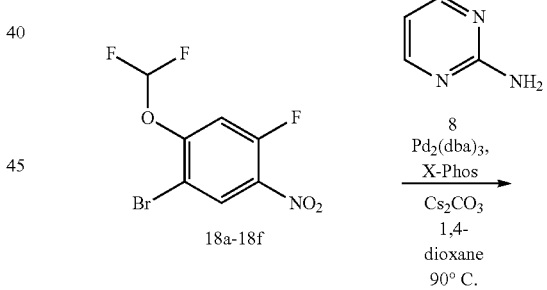

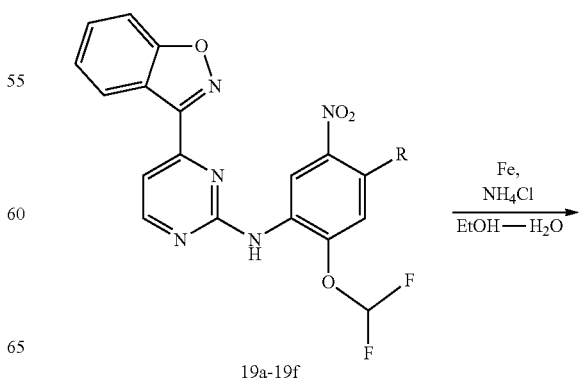

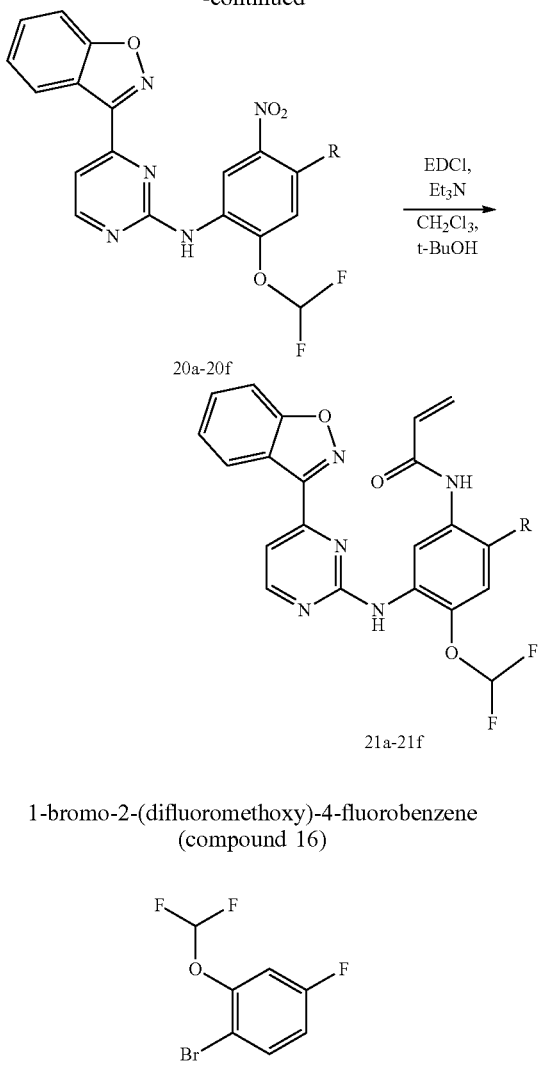

20a-20f 21a-21f 1-bromo-2-(difluoromethoxy)-4-fluorobenzene (compound 16)

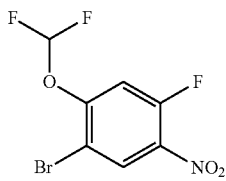

Compound 15 (80 g, 0.42 mol) was dissolved in DMF (800 mL), and sodium carbonate (266 g, 2.5 mol) was added. The temperature was increased to 90° C. Chlorodifluoroacetic acid (191 g, 1.46 mol) was added dropwise. After the completion of addition, temperature was maintained at 90° C. to react overnight. The reaction solution is cooled to room temperature, poured slowly into ice water, and extracted twice with ethyl acetate. The organic phases were combined, washed once with saturated brine, dried over anhydrous sodium sulfate, and spin-dried to obtain 95 g of crude product, which was used directly in the next reaction. $^1$H NMR (400 MHz, CDCl$_3$): δ 7.62-7.58 (m, 1H), 7.04-7.01 (m, 1H), 6.93-6.88 (m, 1H), 6.57 (t, J=72.8 Hz, 1H); MS (ESI) (m/z): [M+H]$^+$ 240.9.

1-bromo-2-(difluoromethoxy)-4-fluoro-5-nitrobenzene (compound 17)

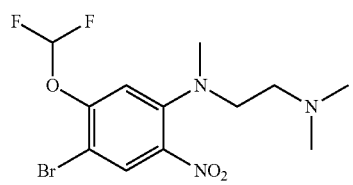 [SMILES: CN(C)CCN(C)c1cc(OC(F)F)c(Br)cc1[N+](=O)[O-]]

Compound 17 was prepared in the same manner as compound 10, except that compound 16 was used instead of compound 9. $^1$H NMR (400 MHz, CDCl$_3$): δ 8.44 (d, J=7.8 Hz, 1H), 7.25 (d, J=11.1 Hz, 1H), 6.71 (t, J=71.0 Hz, 1H); MS (ESI) (m/z): [M+H]$^+$ 286.9.

N$^1$-(4-bromo-5-(difluoromethoxy)-2-nitrophenyl)-N$^1$,N$^2$,N$^2$-trimethylethane-1,2-diamine (compound 18a)

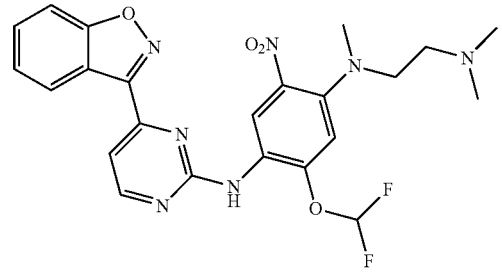 [SMILES: CN(C)CCN(C)c1cc(OC(F)F)c(Nc2nccc(-c3noc4ccccc34)n2)cc1[N+](=O)[O-]]

Compound 18a was prepared in the same manner as compound 11a, except that compound 17 was used instead of compound 10. $^1$H NMR (400 MHz, CDCl$_3$): δ 8.03 (s, 1H), 7.03 (s, 1H), 6.60 (t, J=72.6 Hz, 1H), 3.33 (t, J=6.8 Hz, 2H), 2.87 (s, 3H), 2.57 (t, J=6.8 Hz, 2H), 2.28 (s, 6H); MS (ESI) (m/z): [M+H]$^+$ 369.0.

N$^1$-(4-(benzo[d]isoxazol-3-yl)pyrimidin-2-yl)-2-(difluoromethoxy)-N$^4$-(2-(dimethylamino)ethyl)-N$^4$-methyl-5-nitrobenzene-1,4-diamine (compound 19a)

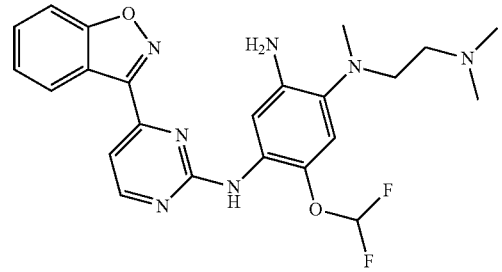

Compound 19a was prepared in the same manner as compound 12a, except that compound 18a was used instead of compound 11a. $^1$H NMR (400 MHz, CDCl$_3$): δ 9.00 (s, 1H), 8.66 (d, J=4.9 Hz, 1H), 8.45 (d, J=7.7 Hz, 1H), 7.69-7.66 (m, 3H), 7.60-7.45 (m, 2H), 7.08 (s, 1H), 6.70 (t, J=72.3 Hz, 1H), 3.30 (t, J=7.0 Hz, 2H), 2.90 (s, 3H), 2.62-2.53 (m, 2H), 2.29 (s, 6H); MS (ESI) (m/z): [M+H]$^+$ 500.2.

N$^4$-(4-(benzo[d]isoxazol-3-yl)pyrimidin-2-yl)-2-yl)-5-(difluoromethoxy)-N$^1$-(2-(dimethylamino)ethyl)-N$^1$-toluene-1,2,4-triamine (compound 20a)

Compound 20a was prepared in the same manner as compound 13a, except that compound 19a was used instead of compound 12a. $^1$H NMR (400 MHz, CDCl$_3$): δ 8.61 (d, J=5.0 Hz, 1H), 8.54 (d, J=8.0 Hz, 1H), 7.90 (s, 1H), 7.73-7.60 (m, 3H), 7.49-7.44 (m, 2H), 6.94 (s, 1H), 6.49 (t, J=74.4 Hz, 1H), 2.97 (t, J=6.4 Hz, 2H), 2.72 (s, 3H), 2.46 (t, J=6.4 Hz, 2H), 2.31 (s, 6H); MS (ESI) (m/z): [M+H]+ 470.2.

Example 6: N-(5-((4-(benzo[d]isoxazol-3-yl)pyrimidin-2-yl)amino)-4-(difluoromethoxy)-2-((2-(dimethylamino)ethyl)(methyl)amino)phenyl)acrylamide (compound 21a)

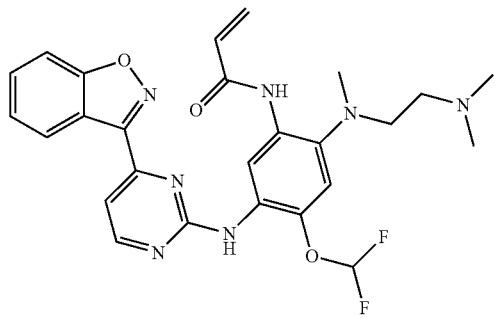 [SMILES: C=CC(=O)Nc1cc(Nc2nccc(-c3noc4ccccc34)n2)c(OC(F)F)cc1N(C)CCN(C)C]

Compound 21a was prepared in the same manner as compound 14a, except that compound 20a was used instead of compound 13a. $^1$H NMR (400 MHz, CDCl$_3$): δ 10.33 (s, 1H), 9.53 (s, 1H), 8.69 (d, J=5.0 Hz, 1H), 8.48 (d, J=8.0 Hz, 1H), 7.67-7.57 (m, 3H), 7.45 (s, 1H), 7.34 (t, J=7.5 Hz, 1H), 7.12 (s, 1H), 6.77-6.28 (m, 3H), 5.75-5.72 (m, 1H), 2.96-2.84 (m, 2H), 2.75 (s, 3H), 2.39-2.32 (m, 8H); MS (ESI) (m/z): [M+H]+ 524.2.

1-(4-bromo-5-(difluoromethoxy)-2-nitrophenyl)-4-methylpiperazine (compound 18b)

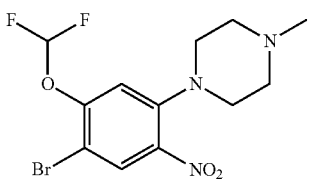

Compound 18b was prepared in the same manner as compound 11a, except that compound 17 was used instead of compound 10 and 4-methylpiperazine was used instead of N,N,N'-trimethylethylenediamine. MS (ESI) (m/z): [M+H]+ 366.0.

4-(benzo[d]isoxazol-3-yl)-N-(2-(difluoromethoxy)-4-(4-methylpiperazin-1-yl)-5-nitrophenyl)pyrimidine-2-amine (compound 19b)

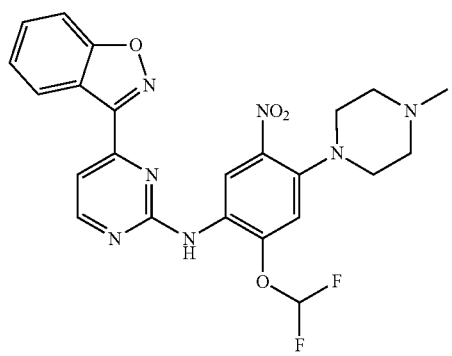 [SMILES: CN1CCN(c2cc(OC(F)F)c(Nc3nccc(-c4noc5ccccc45)n3)cc2N)CC1]

Compound 19b was prepared in the same manner as compound 12a, except that compound 18b was used instead of compound IIa. $^1$H NMR (400 MHz, CDCl$_3$): δ 8.63 (d, J=5.0 Hz, 1H), 8.53 (d, J=8.0 Hz, 1H), 8.03 (s, 1H), 7.77-7.61 (m, 3H), 7.55 (s, 1H), 7.46 (t, J=7.4 Hz, 1H), 6.97 (s, 1H), 6.52 (t, J=74.0 Hz, 1H), 3.21 (m, 4H), 3.03 (m, 4H), 2.68 (s, 3H); MS (ESI) (m/z): [M+H]+ 498.2.

N$^1$-(4-(benzo[d]isoxazol-3-yl)pyrimidin-2-yl)-6-(difluoromethoxy)-4-(4-methylpiperazin-1-yl)benzene-1,3-diamine (compound 20b)

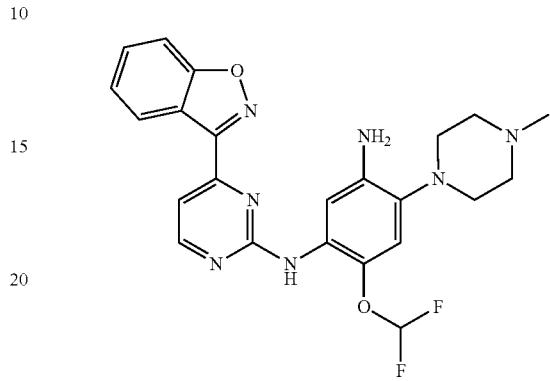

Compound 20b was prepared in the same manner as compound 13a, except that compound 19b was used instead of compound 12a. MS (ESI) (m/z): [M+H]+ 468.2.

Example 7: N-(5-((4-(benzo[d]isoxazol-3-yl)pyrimidin-2-yl)amino)-4-(difluoromethoxy)-2-(4-methylpiperazin-1-yl)phenyl)acrylamide (compound 21b)

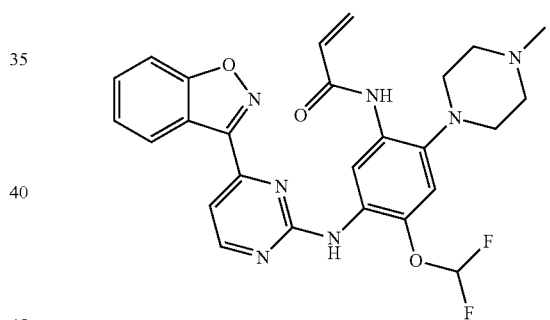

Compound 21b was prepared in the same manner as compound 14a, except that compound 20b was used instead of compound 13a. $^1$H NMR (400 MHz, CDCl$_3$): δ 9.48 (s, 1H), 8.69 (d, J=5.0 Hz, 1H), 8.63 (s, 1H), 8.47 (d, J=8.0 Hz, 1H), 7.73-7.55 (m, 3H), 7.47 (s, 1H), 7.36 (t, J=7.4 Hz, 1H), 7.11 (s, 1H), 6.80-6.25 (m, 3H), 5.82 (d, J=9.8 Hz, 1H), 2.98 (m, 4H), 2.71 (m, 4H), 2.47 (s, 3H); MS (ESI) (m/z): [M+H]+ 522.2.

1-bromo-5-(difluoromethoxy)-2-nitrophenyl)-N,N-dimethylazetidin-3-amine (compound 18c)

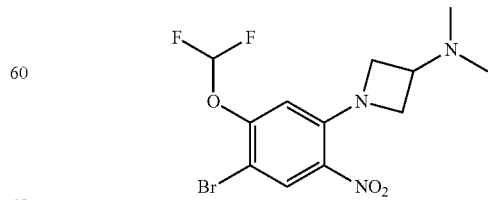

Compound 18c was prepared in the same manner as compound 11a, except that compound 17 was used instead of compound 10 and N,N-dimethylazetidin-3-amine was used instead of N,N,N'-trimethylethylenediamine. MS (ESI) (m/z): [M+H]+ 366.1.

4-(benzo[d]isoxazol-3-yl)-N-(2-(difluoromethoxy)-4-(3-(dimethylamino) azetidin-1-yl)-5-nitrophenyl) pyrimidin-2-amine (compound 19c)

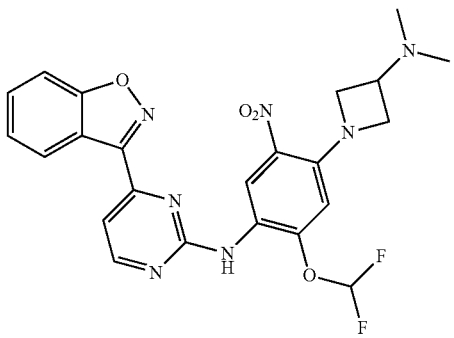

Compound 19c was prepared in the same manner as compound 12a, except that compound 18c was used instead of compound 11a. $^1$H NMR (400 MHz, CDCl$_3$): δ 8.98 (s, 1H), 8.63 (s, 1H), 8.43 (d, J=7.7 Hz, 1H), 7.78-7.61 (m, 3H), 7.52-7.37 (m, 2H), 6.67 (t, J=72.3 Hz, 1H), 6.45 (s, 1H), 4.14 (t, J=7.7 Hz, 2H), 3.76-3.73 (m, 2H), 3.27-3.18 (m, 1H), 2.23 (s, 6H); MS (ESI) (m/z): [M+H]+ 498.2.

N$^1$-(4-(benzo[d]isoxazol-3-yl)pyrimidin-2-yl)-6-(difluoromethoxy)-4-(3-(dimethylamino) azetidin-1-yl)benzene-1,3-diamine (compound 20c)

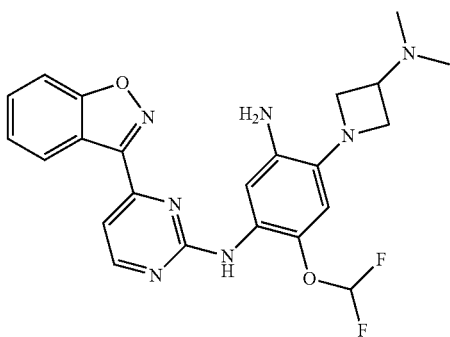 [SMILES: CN(C)C1CN(c2cc(OC(F)F)c(Nc3nccc(-c4noc5ccccc45)n3)cc2[N+](=O)[O-])C1]

Compound 20c was prepared in the same manner as compound 13a, except that compound 19c was used instead of compound 12a. MS (ESI) (m/z): [M+H]+ 468.2.

Example 8: N-(5-((4-(benzo[d]isoxazol-3-yl)pyrimidin-2-yl)amino)-4-(difluoromethoxy)-2-(3-(dimethylamino)azetidin-1-yl)phenyl)acylamide (compound 21c)

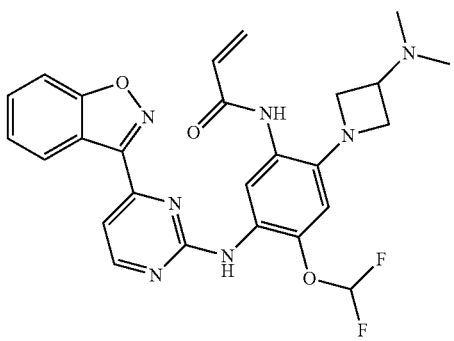 [SMILES: C=CC(=O)Nc1cc(Nc2nccc(-c3noc4ccccc34)n2)c(OC(F)F)cc1N1CC(N(C)C)C1]

Compound 21c was prepared in the same manner as compound 14a, except that compound 20c was used instead of compound 13a. $^1$H NMR (400 MHz. CDCl$_3$): δ 8.77 (s, 1H), 8.61 (d, J=5.0 Hz, 1H), 8.41 (d, J=7.9 Hz, 1H), 7.72-7.49 (m, 4H), 7.39-7.36 (m, 21H), 6.47-6.33 (m, 4H), 5.79 (d, J=8.4 Hz, 1H), 3.94 (t, J=6.6 Hz, 2H), 3.72 (t, J=6.3 Hz, 2H), 3.26-3.14 (m, 1H), 2.28 (s, 6H); MS (ESI) (m/z): [M+H]+ 522.2.

1-(4-bromo-5-(difluoromethoxy)-2-nitrophenyl)-N,N-dimethylpiperidine-4-amine (compound 18d)

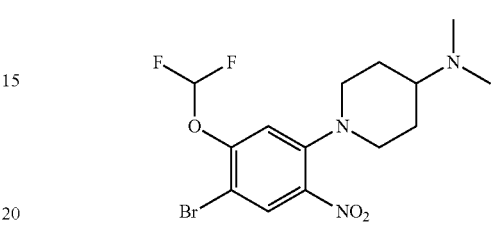

Compound 18d was prepared in the same manner as compound 11a, except that compound 17 was used instead of compound 10 and N,N-dimethylpiperidin-4-amine was used instead of N,N,N'-trimethylethylenediamine. MS (ESI) (m/z): [M+H]+ 394.0.

4-(benzo[d]isoxazol-3-yl)-N-(2-(difluoromethoxy)-4-(4-(diethylamino)piperidin-1-yl)-5-nitrophenyl) pyrimidine-2-amine (compound 19d)

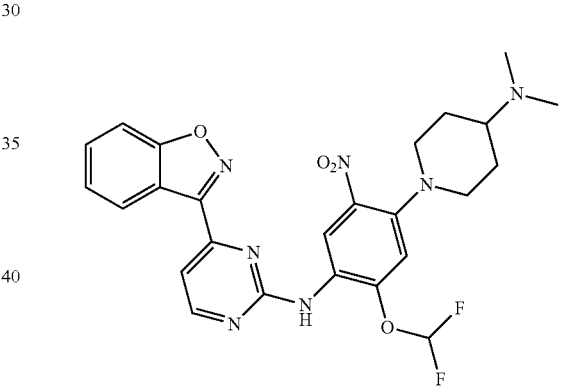

Compound 19d was prepared in the same manner as compound 12a, except that compound 18d was used instead of compound 11a. MS (ESI) (m/z): [M+H]+ 526.2.

N$^1$-(4-(benzo[d]isoxazol-3-yl)pyrimidin-2-yl)-6-(difluoromethoxy)-4-(4-(dimethyamino) piperidin-1-yl)benzene-1,3-diamine (compound 20d)

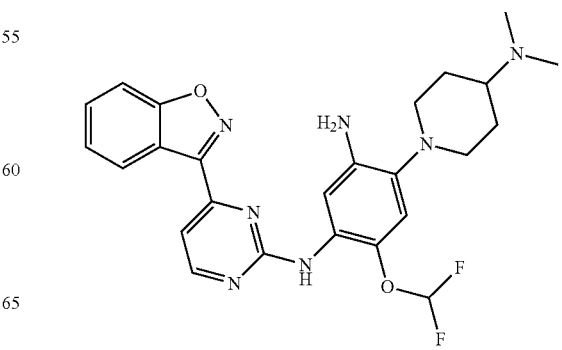

Compound 20d was prepared in the same manner as compound 13a, except that compound 19d was used instead of compound 12a. MS (ESI) (m/z): [M+H]+ 496.2.

Example 9: N-(5-((4-(benzo[d]isoxazol-3-yl)pyrimidin-2-yl)amino)-4-(difluoromethoxy)-2-(4-(dimethylamino)piperidin-1-yl)phenyl)acrylamide (compound 2d)

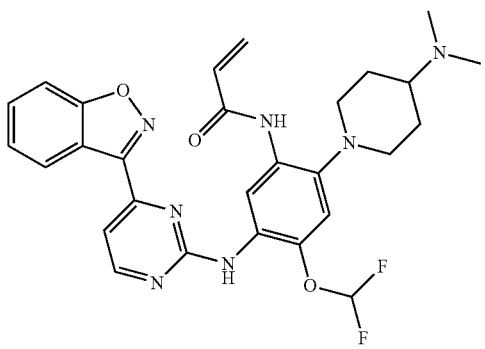 [SMILES: C=CC(=O)Nc1cc(Nc2nccc(-c3noc4ccccc34)n2)c(OC(F)F)cc1N1CCC(N(C)C)CC1]

Compound 21d was prepared in the same manner as compound 14a, except that compound 20d was used instead of compound 13a. $^1$H NMR (400 MHz, CDCl$_3$): δ 9.44 (s, 1H), 8.67 (d, J=5.0 Hz, 1H), 8.55 (s, 1H), 8.45 (d, J=8.0 Hz, 1H), 7.75-7.55 (m, 3H), 7.47 (s, 1H), 7.35 (t, J=7.4 Hz, 1H), 7.04 (s, 1H), 6.79-6.31 (m, 3H), 5.83-5.80 (m, 1H), 3.17-3.14 (m, 2H), 2.83-2.66 (m, 3H), 2.63 (s, 6H), 2.24-2.21 (m, 2H), 2.01-1.93 (m, 2H); MS (ESI) (m/z): [M+H]+ 550.2.

(S)-1-(1-(4-bromo-5-(difluoromethoxy)-2-nitrophenyl)pyrrolidin-2-yl)-N,N-dimethylmethanamine (compound 18e)

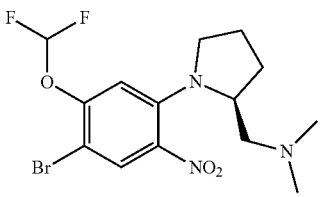 [SMILES: CN(C)C[C@@H]1CCCN1c1cc(OC(F)F)c(Br)cc1[N+](=O)[O-]]

Compound 18e was prepared in the same manner as compound 11a, except that compound 17 was used instead of compound 10 and (S—N,N-dimethyl-1-(pyrrolidin-2-yl)-methanamine was used instead of N,N,N'-trimethylethylenediamine. MS (ESI) (m/z): [M+H]+ 394.0.

(S)-4-(benzo[d]isoxazol-3-yl)-N-(2-(difluoromethoxy)-4-(2-((dimethylamino)methyl)pyrrolidin-1-yl)-5-nitrophenyl)pyrimidin-2-amine (compound 19e)

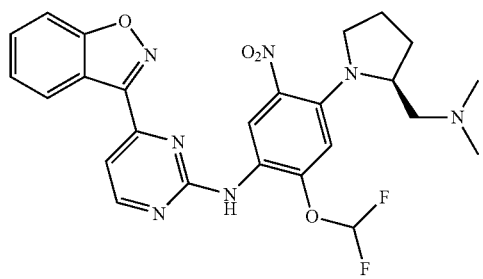 [SMILES: CN(C)C[C@@H]1CCCN1c1cc(OC(F)F)c(Nc2nccc(-c3noc4ccccc34)n2)cc1[N+](=O)[O-]]

Compound 19e was prepared in the same manner as compound 12a, except that compound 18e was used instead of compound 11a. MS (ESI) (m/z): [M+H]+ 526.2.

(S)—N$^1$-(4-(benzo[d]isoxazol-3-yl)pyrimidin-2-yl)-6-(difluoromethoxy)-4-(2-((dimethylamino)methyl)pyrolidin-1-yl)benzene-1,3-diamine (compound 20e)

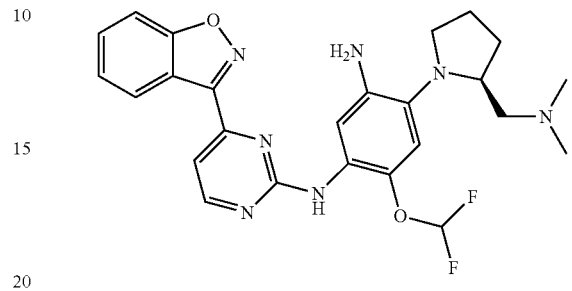

Compound 20e was prepared in the same manner as compound 13a, except that compound 19e was used instead of compound 12a. MS (ESI) (m/z): [M+H]+ 496.2.

Example 10: (S)—N-(5-((4-(benzo[d]isoxazol-3-yl)pyrimidin-2-yl)amino)-4-difluoromethoxy)-2-(2-((dimethylamino)methyl)pyrrolidin-1-yl)phenyl)acrylamide (compound 21e)

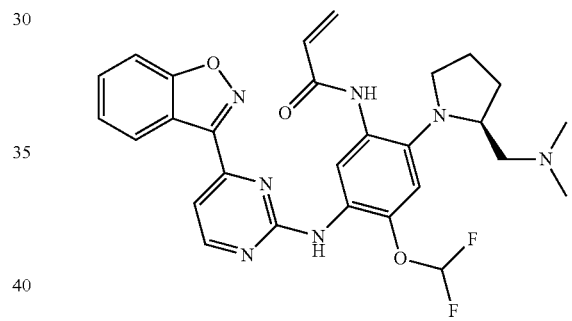

Compound 21e was prepared in the same manner as compound 14a, except that compound 20e was used instead of compound 13a. $^1$H NMR (400 MHz, CDCl$_3$): δ 9.87 (s, 1H), 9.31 (s, 1H), 8.66 (d, J=5.1 Hz, 1H), 8.46 (d, J=8.0 Hz, 1H), 7.73-7.55 (m, 3H), 7.44-7.41 (m, 2H), 6.96 (s, 1H), 6.85-6.32 (m, 3H), 5.75 (d, J=11.6 Hz, 1H), 3.83-3.52 (m, 2H), 3.01-2.95 (m, 1H), 2.53 (s, 6H), 2.32-1.95 (m, 4H), 1.88-1.78 (m, 2H); MS (ESI) (m/z): [M+H]+ 550.2.

2-(4-bromo-5-(difluoromethoxy)-2-nitrophenyl)-5-methyl-2,5-diazaspiro[3.4]octane (compound 18f)

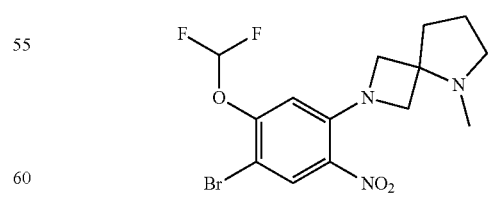

Compound 18f was prepared in the same manner as compound 11a, except that compound 17 was used instead of compound 10 and 5-methyl-2,5-diazaspiro[3.4]octane was used instead of N,N,N'-trimethylethylenediamine. $^1$H NMR (400 MHz, CDCl$_3$): δ 8.12 (s, 1H), 6.84-6.36 (m, 2H), 4.15 (d, J=9.2 Hz, 2H), 3.73 (d, J=9.2 Hz, 21H), 2.79 (t, J=7.2 Hz, 2H), 2.51 (s, 3H), 2.21-2.05 (m, 2H), 1.86-1.79 (m, 2H); MS (ESI) (m/z): [M+H]+ 392.0.

4-(benzo[d]isoxazol-3-yl)-N-(2-(difluoromethoxy)-4-(5-methyl-2,5-diazaspiro[3.4]oct-2-yl)-5-nitrophenyl)pyrimidin-2-amine (compound 19f)

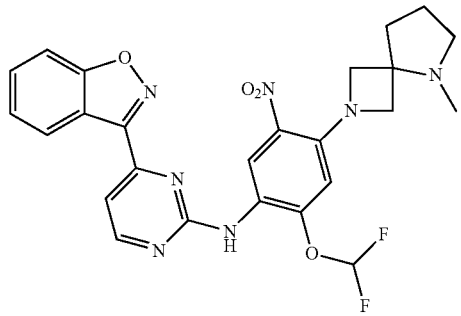 [SMILES: CN1CCCC12CN(c1cc(OC(F)F)c(Nc3nccc(-c4noc5ccccc45)n3)cc1[N+](=O)[O-])C2]

Compound 19f was prepared in the same manner as compound 12a, except that compound 18f was used instead of compound 11a. MS (ESI) (m/z): [M+H]+524.2.

N1-(4-(benzo[d]isoxazol-3-yl)pyrimidin-2-yl)-6-(difluoromethoxy)-4-(5-methyl-2,5-diazaspiro[3.4]oct-2-yl)benzene-1,3-diamine (compound 20f)

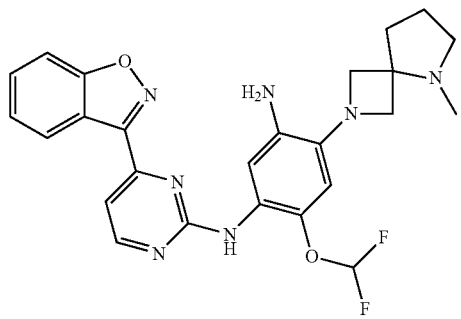

Compound 20f was prepared in the same manner as compound 13a, except that compound 19f was used instead of compound 12a. MS (ESI) (m/z): [M+H]+ 494.2.

Example 11: N-(5-((4-(benzo[d]isoxazol-3-yl)pyrimidin-2-yl)amino)-4-(difluoromethoxy)-2-(5-methyl-2,5-diazaspiro[3.4]oct-2-yl)phenyl)acrylamide (compound 21f)

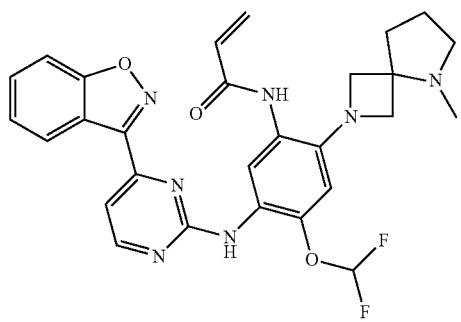 [SMILES: C=CC(=O)Nc1cc(Nc2nccc(-c3noc4ccccc34)n2)c(OC(F)F)cc1N1CC2(CCCN2C)C1]

Compound 21f was prepared in the same manner as compound 14a, except that compound 20f was used instead of compound 13a. 1H NMR (400 MHz, CDCl3): δ 8.67 (s, 1H), 8.60 (d, J=5.0 Hz, 1H), 8.41 (d, J=7.6 Hz, 1H), 7.72-7.48 (m, 4H), 7.48-7.36 (m, 2H), 6.81-6.30 (m, 4H), 5.79 (m, 1H), 4.10 (d, J=8.0 Hz, 2H), 3.71 (d, J=7.7 Hz, 2H), 2.93 (m, 2H), 2.64 (s, 3H), 2.31-2.17 (m, 2H), 1.91-1.90 (m, 2H); MS (ESI) (m/z): [M+H]+ 548.2.

The synthesis route of compounds 31a-31f is as shown in Scheme 3:

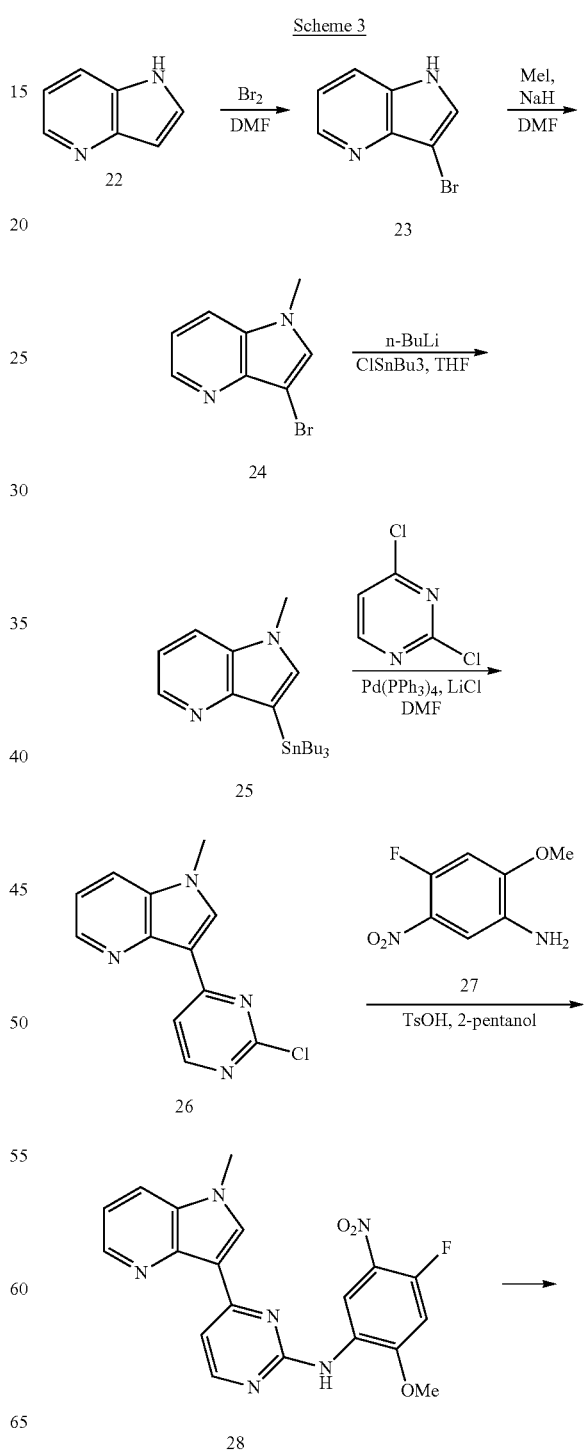

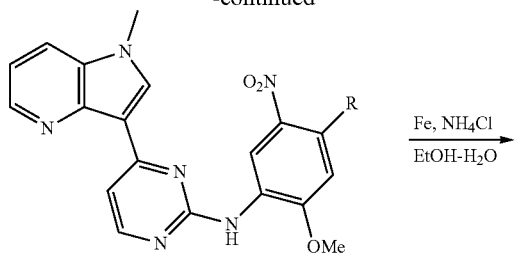

29a-29f

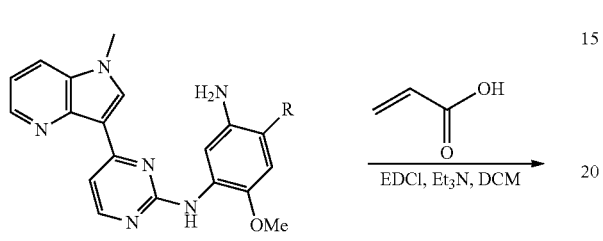

30a-30f

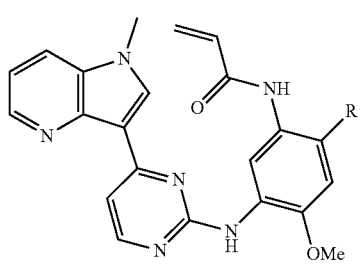

31a-31f 1-methyl-3-(tributyltin)-1H-pyrrolo[3,2-b]pyridine (compound 25)

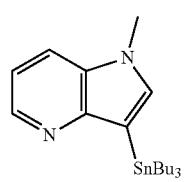

3-bromo-1-methyl-1H-pyrrolo[3,2-b]pyridine (compound 24, synthesized with reference to Bioorganic and Medicinal Chemistry Letters, 2014, 24, 3238-3242) (2.4 g, 11.4 mmol) was dissolved in dry THF (60 mL), and n-butyllithium (2.5 M n-hexane solution, 5.0 mL, 12.5 mmol) was added dropwise at −70° C. After the completion of addition, the temperature of the system was maintained at −70° C. and stirring continued for 30 min. Then tributyltin chloride (4.06 g, 12.5 mmol) was added dropwise at the same temperature. After the completion of addition, the temperature was increased slowly to room temperature, and the mixture was stirred for 3 h. 500 mL ethyl acetate was added, and the organic phase was washed with water and saturated brine sequentially. After drying and concentration, the crude product was obtained as a yellow oily liquid (5.4 g, purity 70%). This crude product could be used directly in the next reaction without purification.

3-(2-chloropyrimidin-4-yl)-1-methyl-1H-pyrrolo[3,2-b]pyridine (compound 26)

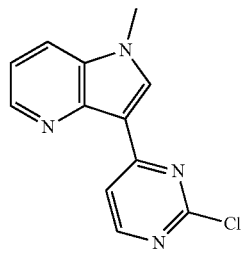 [SMILES: Cn1cc(-c2ccnc(Cl)n2)c2ncccc21]

Compound 25 (5.4 g. purity 70%, 9.0 mmol) was dissolved in DMF (70 mL), and 2,4-dichloropyrimidine (1.34 g, 9.0 mmol), lithium chloride (1.89 g, 45.0 mmol), and bis(triphenylphosphino)dichloropalladium (320 mg, 0.45 mmol) were added sequentially. The system was replaced three times with nitrogen, and heated to 100° C. to react for 16 h. After the system was cooled to room temperature, a large quantity of ethyl acetate was added. The organic phase was washed with water and saturated brine sequentially. The organic phase was dried and concentrated, and was purified over a column to obtain the crude product as a light yellow solid (500 mg, purity 80%), which could be used directly in the next reaction without purification. MS (ESI) (m/z): [M+H]$^+$ 245.0.

N-(4-fluoro-2-methoxy-5-nitrophenyl)-4-(1-methyl-H-pyrrolo[3,2-b]pyridin-3-yl)pyrimidin-2-amine (compound 28)

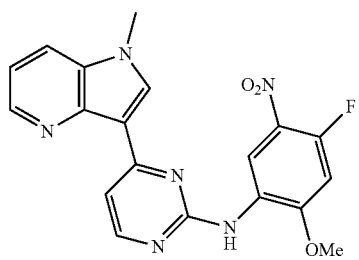 [SMILES: COc1cc(F)c([N+](=O)[O-])cc1Nc1nccc(-c2cn(C)c3cccnc23)n1]

Compound 26 (500 mg, purity 80%, 1.64 mmol) was dissolved in sec-pentanol (20 mL), and p-toluene sulfonic acid (420 mg, 2.46 mmol) and compound 27 (310 mg, 1.64 mmol) were added sequentially. The mixture was heated to 110° C. to react for 18 h. After the completion of reaction, the system was cooled to room temperature and stirring was continued for 30 min before filtration. The precipitated solid was washed with a small amount of sec-pentanol to obtain undried yellow crude product compound. The crude product was slurried with an appropriate amount of acetonitrile and filtered to obtain the light yellow solid compound (650 mg). MS (ESI) (m/z): [M+H]$^+$ 395.1.

N[1]-(2-(dimethylamino)ethyl)-5-methoxy-N[1]-methyl-N[4]-(4-(1-methyl-1H-pyrrolo[3,2-b]pyridin-3-yl)pyrimidin-2-yl)-2-nitrobenzene-1,4-diamine (compound 29a)

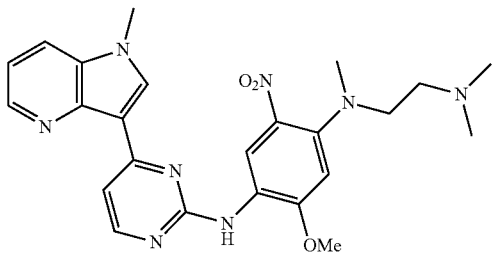 [SMILES: COc1cc(N(C)CCN(C)C)c([N+](=O)[O-])cc1Nc1nccc(-c2cn(C)c3cccnc23)n1]

N,N-diisopropylethylamine (280 mg, 2.14 mmol) and N,N,N'-trimethylethylenediamine (202 mg, 1.98 mmol) were added sequentially to a solution of compound 28 (650 mg, 1.65 mmol) in N,N-dimethylacetamide (15 mL) at room temperature. The mixture was heated to 70° C. to react for 6 hours. After the completion of reaction, ethyl acetate and water was added. The mixture was fully stirred and filtered over celite. The organic phase was washed several times with saturated brine, and dried and concentrated to obtain compound 29a as a dark red solid (450 mg, 57%). $^1$H NMR (400 MHz. CDCl$_3$): δ 9.77 (s 1H), δ 8.65 (s, 1H), 8.64-8.60 (m, 1H), 8.46 (d, J=5.2 Hz, 1H), 8.26 (d, J=5.2 Hz, 1H), 7.72-7.68 (m, 1H), 7.56 (s, 1H), 7.24-7.20 (m, 1H), 6.67 (s, 1H), 3.99 (s, 6H), 3.30 (t, J=7.2 Hz, 2H), 3.01 (s, 3H), 2.58 (t, J=7.2 Hz, 2H), 2.27 (s, 6H); MS (ESI) (m/z): MS (ESI) (m/z): [M+H]$^+$477.2.

N[1]-(2-(dimethylamino)ethyl)-5-methoxy-N[1]-methyl-N[4]-(4-(1-methyl-1H-pyrrolo[3,2-b]pyridin-3-yl)pyrimidin-2-yl)benzene-1,2,4-triamine (compound 30a)

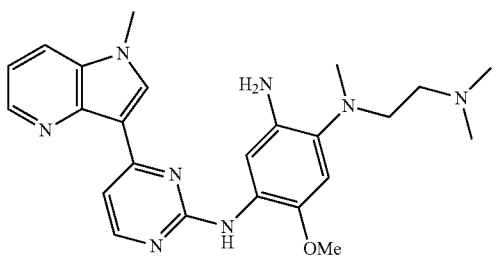

Compound 29a (450 mg, 0.95 mmol) was dissolved in ethanol (18 mL)/H$_2$O (6 mL), and iron powder (300 mg, 5.70 mmol) and ammonium chloride (36 mg, 0.67 mmol) were added. The reaction system was heated to reflux and react for 2 h. After the completion of reaction, the reactant was poured into a solution of dichloromethane:methanol=10:1, and an appropriate amount of water was added and stirred. The mixture was filtered over celite. The organic phase was dried and concentrated, and purified by column chromatography (dichloromethane:methanol=100:1 to 10:1) to obtain a light yellow solid 30a (200 mg, 47%). $^1$H NMR (400 MHz, CDCl$_3$): δ 8.62 (dd, J=4.8, 1.6 Hz, 1H), 8.45 (d, J=5.2 Hz, 1H), 8.23 (s, 1H), 8.17 (d, J=5.2 Hz, 1H), 8.15 (s, 1H), 7.69-7.65 (m, 1H), 7.58 (s, 1H), 7.24-7.18 (m, 1H), 6.70 (s, 1H), 3.89 (s, 3H), 3.84 (s, 3H), 3.04 (t, J=7.2 Hz, 2H), 2.68 (s, 3H), 2.50 (t, J=7.2 Hz, 2H), 2.34 (s, 6H); MS (ESI) (m/z): [M+H]$^+$ 447.2.

Example 12: N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide (compound 31a)

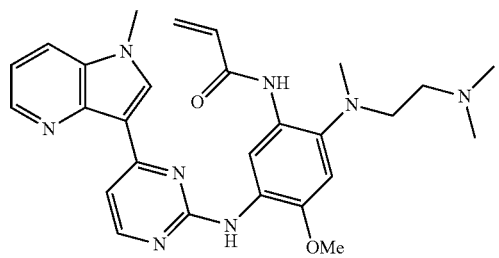 [SMILES: C=CC(=O)Nc1cc(Nc2nccc(-c3cn(C)c4cccnc34)n2)c(OC)cc1N(C)CCN(C)C]

Compound 30a (120 mg, 0.27 mmol) was dissolved in dichloromethane (10 mL)/tert-butanol (1 mL), and triethylamine (50 mg, 0.54 mmol), EDCI (100 mg, 0.54 mmol), and acrylic acid (40 mg, 0.54 mmol) were added sequentially at 0-5° C. The mixture was stirred at room temperature for 2 h, and an appropriate amount of ethyl acetate was added. The organic phase was washed with water. The organic phase was dried and concentrated, and purified by column chromatography to obtain a whitish solid 31a (80 mg, 59%). $^1$H NMR (400 MHz, CDCl$_3$): δ 10.24 (bs, 1H), 9.94 (s, 1H), 9.56 (bs, 1H), 8.61-8.57 (m, 1H), 8.42 (d, J=5.2 Hz, 1H), 8.24 (d, J=5.2 Hz, 1H), 7.77 (s, 1H), 7.70-7.65 (m, 1H), 7.21-7.15 (m, 1H), 6.80 (s, 1H), 6.50-6.34 (m, 2H), 5.72 (m, 1H), 4.04 (s, 3H), 3.89 (s, 3H), 2.90 (t, J=7.2 Hz, 2H), 2.71 (s, 3H), 2.30-2.22 (m, 8H); MS (ESI) (m/z): [M+H]$^+$ 501.3.

N-(2-methoxy-4-(4-methylpiperazin-1-yl)-5-nitrophenyl)-4-(1-methyl-H-pyrrolo[3,2-b]pyridin-3-yl)pyrimidin-2-amine (compound 29b)

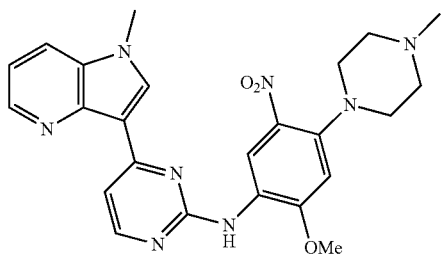

Compound 29b was prepared in the same manner as compound 29a, except that 4-methylpiperazine was used instead of N,N,N'-trimethylethylenediamine, MS (ESI) (m/z): [M+H]$^+$ 475.1.

6-methoxy-N[1]-(4-(1-methyl-1H-pyrrolo[3,2-b]pyridin-3-yl)pyrimidin-2-yl)-4-(4-methylpiperazin-1-yl)benzene-1,3-diamine (compound 30b)

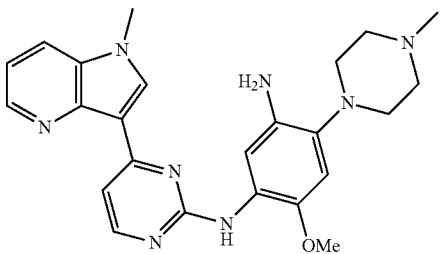 [SMILES: COc1cc(N2CCN(C)CC2)c([N+](=O)[O-])cc1Nc1nccc(-c2cn(C)c3cccnc23)n1]

Compound 30b was prepared in the same manner as compound 30a, except that compound 29b was used instead of compound 29a. $^1$H NMR (400 MHz, CDCl$_3$): δ 8.63-8.59 (m, 1H), 8.44 (d, J=5.2 Hz, 1H), 8.22 (s, 1H), 8.17 (d, J=5.2 Hz, 1H), 8.15 (s, 1H), 7.70-7.64 (m, 1H), 7.56 (s, 1H), 7.24-7.18 (m, 1H), 6.71 (s, 1H), 3.89 (s, 3H), 3.84 (s, 3H), 2.94 (m, 4H), 2.58 (m, 4H), 2.37 (s, 3H); MS (ESI) (m/z): [M+H]$^+$ 445.2.

Example 13: N-(4-methoxy-5-((4-(1-methyl-H-pyrrolo[3,2-b]pyridin-3-yl)pyrimidin-2-yl)amino)-2-(4-methylpiperazin-1-yl)phenyl)acrylamide (compound 31b)

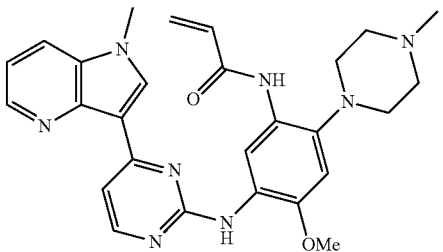 [SMILES: C=CC(=O)Nc1cc(Nc2nccc(-c3cn(C)c4cccnc34)n2)c(OC)cc1N1CCN(C)CC1]

Compound 31b was prepared in the same manner as compound 31a, except that compound 30b was used instead of compound 30a. $^1$H NMR (400 MHz, CDCl$_3$): δ 9.91 (bs, 1H), 9.47 (s, 1H), 8.80 (bs, 1H), 8.59-8.55 (m, 1H), 8.42 (d, J=5.2 Hz, 1H), 8.24 (d, J=5.2 Hz, 1H), 7.77 (s, 1H), 7.67-7.63 (m, 1H), 7.20-7.16 (m, 1H), 6.80 (s, 1H), 6.48-6.30 (m, 2H), 5.78 (m, 1H), 4.02 (s, 3H), 3.88 (s, 3H), 2.92 (m, 4H), 2.62 (m, 4H), 2.41 (s, 3H); MS (ESI) (m/z): [M+H]$^+$ 499.2.

N-(4-(3-(dimethylamino)azetidin-1-yl)-2-methoxy-5-nitrophenyl)-4-(1-methyl-1H-pyrrolo[3,2-b]pyridin-3-yl)pyrimidin-2-amine (compound 29c)

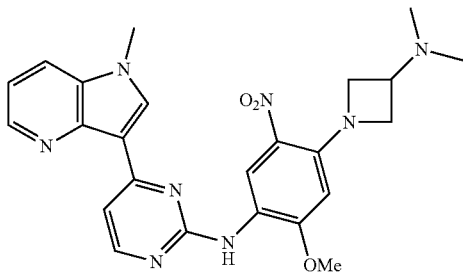

Compound 29c was prepared in the same manner as compound 29a, except that N,N-dimethylazetidin-3-amine was used instead of N,N,N'-trimethylethylenediamine. $^1$H NMR (400 MHz, CDCl$_3$): δ 9.82 (s, 1H), 8.73 (s, 1H), 8.64 (d, J=4.4 Hz, 1H), 8.47 (d, J=5.1 Hz, 1H), 8.27 (d, J=5.2 Hz, 1H), 7.73 (d, J=8.1 Hz, 1H), 7.54 (s, 1H), 7.26-7.23 (m, 1H), 6.07 (s, 1H), 4.22 (t, J=7.6 Hz, 2H), 4.01 (s, 6H), 3.80-3.72 (m, 2H), 3.25-3.22 (m, 1H), 2.25 (s, 6H); MS (ESI) (m/z): [M+H]$^+$ 475.2.

4-(3-(dimethylamino)azetidin-1-yl)-6-methoxy-N[1]-(4-(1-methyl-1H-pyrrolo[3,2-b]pyridin-3-yl)pyrimidin-2-yl)benzene-1,3-diamine (compound 30c)

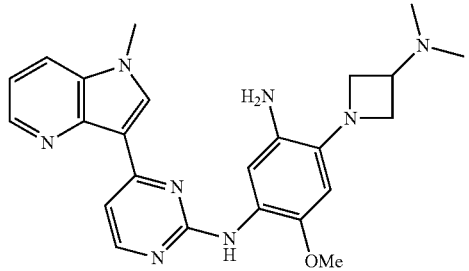 [SMILES: COc1cc(N2CC(N(C)C)C2)c([N+](=O)[O-])cc1Nc1nccc(-c2cn(C)c3cccnc23)n1]

Compound 30c was prepared in the same manner as compound 30a, except that compound 29c was used instead of compound 29a. MS (ESI) (m/z): [M+H]$^+$ 445.2.

Example 14: N-(2-(3-(dimethylamino)azetidin-1-yl)-4-methoxy-5-((4-(1-methyl-1H-pyrrolo[3,2-b]pyridin-3-yl)pyrimidin-2-yl)amino)phenyl)acrylamide (compound 31c)

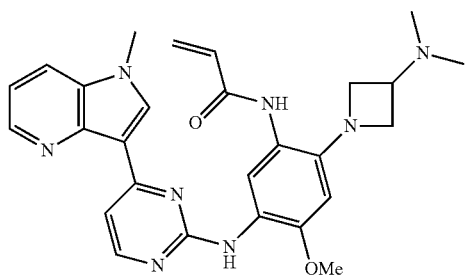 [SMILES: C=CC(=O)Nc1cc(Nc2nccc(-c3cn(C)c4cccnc34)n2)c(OC)cc1N1CC(N(C)C)C1]

Compound 31c was prepared in the same manner as compound 31a, except that compound 30c was used instead of compound 30a. $^1$H NMR (400 MHz, CDCl$_3$): δ 9.40 (s, 1H), 9.23 (s, 1H), 8.60 (d, J=4.5 Hz, 1H), 8.42 (d, J=5.2 Hz, 1H), 8.21 (d, J=5.2 Hz, 1H), 7.76 (s, 1H), 7.67 (d, J=8.0 Hz, 1H), 7.62 (s, 1H), 7.21-7.18 (m, 1H), 6.56-6.40 (m, 3H), 5.80-5.78 (m, 1H), 4.01 (s, 3H), 3.92 (s, 3H), 3.88 (t, J=6.8 Hz, 2H), 3.64 (t, J=6.5 Hz, 2H), 3.17-3.11 (m, 1H), 2.24 (s, 6H); MS (ESI) (m/z): [M+H]$^+$ 499.2.

N-(4-(4-(dimethylamino)piperidin-1-yl)-2-methoxy-5-nitrophenyl)-4-(1-methyl-1H-pyrrolo[3,2-b]pyridin-3-yl)pyrimidin-2-amine (compound 29d)

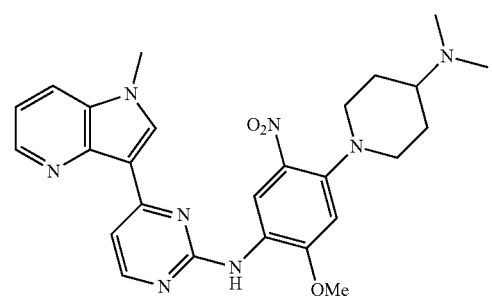 [SMILES: COc1cc(N2CCC(N(C)C)CC2)c([N+](=O)[O-])cc1Nc1nccc(-c2cn(C)c3cccnc23)n1]

Compound 29d was prepared in the same manner as compound 29a, except that N,N-dimethylpiperidin-4-amine was used instead of N,N,N'-trimethylethylenediamine. ¹H NMR (400 MHz, CDCl₃): δ 9.86 (s, 1H), 8.67 (s, 1H), 8.63-8.58 (m, 1H), 8.46 (d, J=5.2 Hz, 1H), 8.26 (d, J=5.2 Hz, 1H), 7.73-7.67 (m, 1H), 7.56 (s, 1H), 7.24-7.18 (m, 1H), 6.59 (s, 1H), 3.99 (s, 3H), 3.98 (s, 3H), 3.38 (m, 2H), 2.85 (m, 2H), 2.48-2.22 (m, 7H), 1.98-1.74 (m, 4H); MS (ESI) (m/z): [M+H]⁺ 503.2.

4-(4-(dimethylamino)piperidin-1-yl)-6-methoxy-N¹-(4-(1-methyl-1H-pyrrolo[3,2-b]pyridin-3-yl)pyrimidin-2-yl)benzene-1,3-diamine (compound 30d)

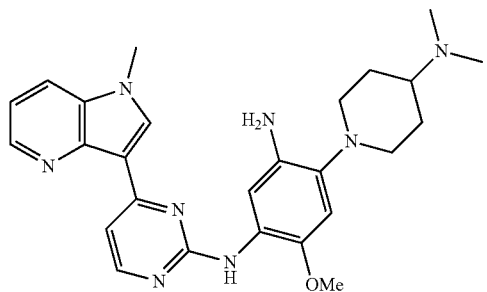

Compound 30d was prepared in the same manner as compound 30a, except that compound 29d was used instead of compound 29a. ¹H NMR (400 MHz, CDCl₃): δ 8.63-8.59 (m, 1H), 8.45 (d J=5.2 Hz, 1H), 8.23 (s, 1H), 8.17 (d, J=5.2 Hz, 1H), 8.14 (s, 1H), 7.70-7.65 (m, 1H), 7.54 (s, 1H), 7.24-7.18 (m, 1H), 6.67 (s, 1H), 3.89 (s, 3H), 3.84 (s, 3H), 3.18 (m, 2H), 2.68-2.60 (m, 2H), 2.34 (s, 6H), 2.28 (m, 1H), 1.95 (m, 2H), 1.68 (m, 2H); MS (ESI) (m/z): [M+H]⁺ 473.2.

Example 15: N-(2-(4-(dimethylamino)piperidin-1-yl)-4-methoxy-5-((4-(1-methyl-1H-pyrrolo[3,2-b]pyridin-3-yl)pyrimidin-2-yl)amino)phenyl)acrylamide (compound 31d)

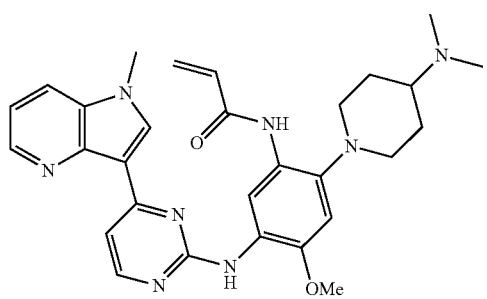 [SMILES: C=CC(=O)Nc1cc(Nc2nccc(-c3cn(C)c4cccnc34)n2)c(OC)cc1N1CCC(N(C)C)CC1]

Compound 31d was prepared in the same manner as compound 31a, except that compound 30d was used instead of compound 30a. ¹H NMR (400 MHz, CDCl₃): δ 9.89 (bs, 1H), 9.48 (s, 1H), 8.77 (bs, 1H), 8.61-8.57 (m, 1H), 8.42 (d, J=5.2 Hz, 1H), 8.24 (d, J=5.2 Hz, 1H), 7.74 (s, 1H), 7.69-7.65 (m, 1H), 7.21-7.15 (m, 1H), 6.76 (s, 1H), 6.44-6.30 (m, 2H), 5.78 (m, 1H), 4.02 (s, 3H), 3.89 (s, 3H), 3.03 (m, 2H), 2.74 (m, 2H), 2.36 (s, 6H), 2.19 (m, 1H), 2.04 (m, 2H), 1.64 (m, 2H); MS (ESI) (m/z): [M+H]⁺ 527.2.

(S)—N-(4-(2-((dimethylamino)methyl)pyrrolidin-1-yl)-2-methoxy-5-nitrophenyl)-4-(1-methyl-H-pyrrolo[3,2-b]pyridin-3-yl)pyrimidin-2-amine (compound 29e)

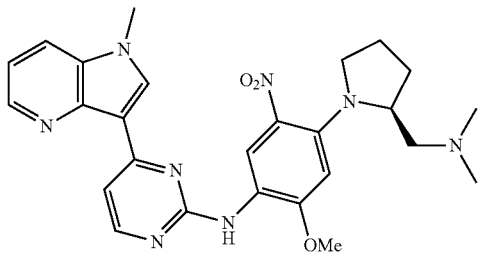 [SMILES: COc1cc(N2CCC[C@H]2CN(C)C)c([N+](=O)[O-])cc1Nc1nccc(-c2cn(C)c3cccnc23)n1]

Compound 29e was prepared in the same manner as compound 29a, except that (S)—N,N-dimethyl-1-(pyrrolidin-2-yl)-methanamine was used instead of N,N,N'-trimethylethylenediamine. MS (ESI) (m/z): [M+H]⁺ 503.2.

(S)-4-(2-((dimethylamino)methyl)pyrrolidin-1-yl)-6-methoxy-N¹-(4-(1-methyl-1H-pyrrolo[3,2-b]pyridin-3-yl)pyrimidin-2-yl)benzene-1,3-diamine (compound 30e)

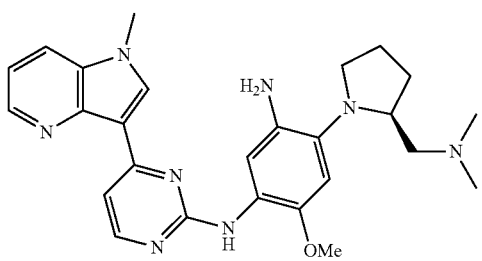 [SMILES: COc1cc(N2CCC[C@H]2CN(C)C)c(N)cc1Nc1nccc(-c2cn(C)c3cccnc23)n1]

Compound 30e was prepared in the same manner as compound 30a, except that compound 29e was used instead of compound 29a. MS (ESI) (m/z): [M+H]⁺ 473.3.

Example 16: (S)—N-(2-(2-((dimethylamino)methyl)pyrrolidin-1-yl)-4-methoxy-5-(4-(1-methyl-1H-pyrrolo[3,2-b]pyridin-3-yl)pyrimidin-2-yl)amino)phenyl)acrylamide (compound 31e)

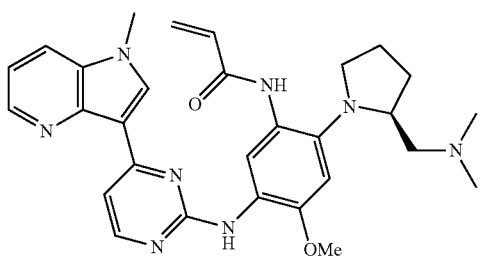 [SMILES: C=CC(=O)Nc1cc(Nc2nccc(-c3cn(C)c4cccnc34)n2)c(OC)cc1N1CCC[C@H]1CN(C)C]

Compound 31e was prepared in the same manner as compound 31a, except that compound 30e was used instead of compound 30a. ¹H NMR (400 MHz, CDCl₃): δ 9.83 (s, 1H), 9.43 (s, 1H), 9.39 (s, 1H), 8.65-8.56 (m, 1H), 8.43 (d, J=5.2 Hz, 1H), 8.27 (d, J=5.2 Hz, 1H), 7.75 (s, 1H), 7.73-7.67 (m, 1H), 7.22-7.19 (m, 1H), 7.06 (d, J=28.2 Hz, 1H), 6.68 (s, 1H), 6.51-6.46 (m, 1H), 5.79-5.76 (m, 1H), 4.02 (s, 3H), 3.91 (s, 3H), 3.75-3.66 (m, 1H), 2.93-2.81 (m, 2H), 2.65 (s, 6H), 2.40-2.21 (m, 2H), 2.19-1.89 (nm, 4H); MS (ESI) (m/z): [M+H]⁺ 527.3.

N-(2-methoxy-4-(5-methyl-2,5-diazaspiro[3.4]oct-2-yl)-5-nitrophenyl)-4-(1-methyl-1H-pyrrolo[3,2-b]pyridin-3-yl)pyrimidin-2-amine (compound 29f)

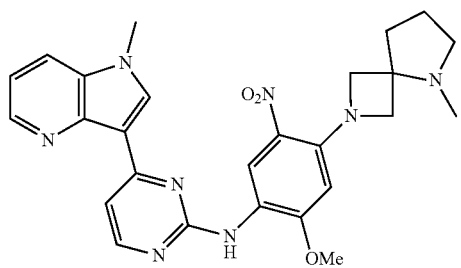

Compound 29f was prepared in the same manner as compound 29a, except that 5-methyl-2,5-diazaspiro[3.4]octane was used instead of N,N,N'-trimethylethylenediamine. ¹H NMR (400 MHz, CDCl₃): δ 9.75 (s, 1H), 8.70 (s, 1H), 8.65-8.58 (m, 1H), 8.44 (d, J=5.2 Hz, 1H), 8.24 (d, J=5.2 Hz, 1H), 7.73-7.67 (m, 1H), 7.50 (s, 1H), 7.24-7.18 (m, 1H), 6.05 (s, 1H), 4.13 (m, 2H), 3.98 (s, 6H), 3.76 (m, 2H), 2.74 (m, 2H), 2.50 (s, 3H), 2.12 (m, 2H), 1.81 (m, 2H); MS (ESI) (m/z): [M+H]⁺ 501.2.

6-methoxy-N¹-(4-(1-methyl-1H-pyrrolo[3,2-b]pyridin-3-yl)pyrimidin-2-yl)-4-(5-methyl-2,5-diazaspiro[3.4]oct-2-yl)benzene-1,3-diamine (compound 30f)

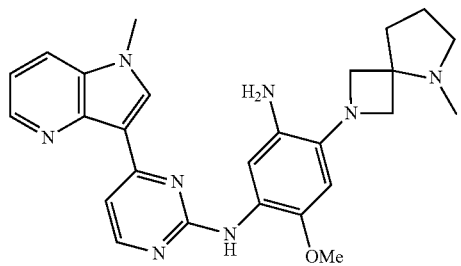 [SMILES: COc1cc(N2CC3(CCCN3C)C2)c([N+](=O)[O-])cc1Nc1nccc(-c2cn(C)c3cccnc23)n1]

Compound 30f was prepared in the same manner as compound 30a, except that compound 29f was used instead of compound 29a. ¹H NMR (400 MHz, CDCl₃): δ 8.63-8.59 (m, 1H), 8.44 (d, J=5.2 Hz, 1H), 8.23 (s, 1H), 8.13 (d, J=5.2 Hz, 1H), 8.05 (s, 1H), 7.70-7.64 (m, 1H), 7.43 (s, 1H), 7.22-7.17 (m, 1H), 6.35 (s, 1H), 4.13-3.54 (m, 10H), 2.76 (m, 2H), 2.53 (s, 3H), 2.20 (m, 2H), 1.82 (m, 2H); MS (ESI) (m/z): [M+H]⁺ 471.2.

Example 17: N-(4-methoxy-5-((4-(1-methyl-1H-pyrrolo[3,2-b]pyridin-3-yl)pyrimidin-2-yl)amino)-2-(5-methyl-2,5-diazaspiro[3.4]oct-2-yl)phenyl)acrylamide (compound 31f)

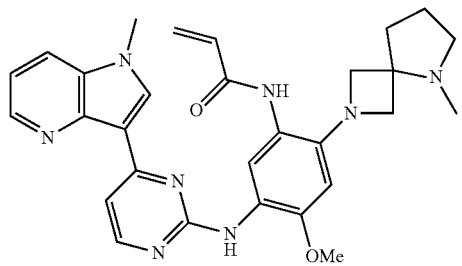 [SMILES: C=CC(=O)Nc1cc(Nc2nccc(-c3cn(C)c4cccnc34)n2)c(OC)cc1N1CC2(CCCN2C)C1]

Compound 31 f was prepared in the same manner as compound 31a, except that compound 30f was used instead of compound 30a. ¹H NMR (400 MHz, CDCl₃): δ 9.22 (be, 1H), 9.14 (s, 1H), 8.59-8.55 (m, 1H), 8.40 (d, J=5.2 Hz, 1H), 8.18 (d, J=5.2 Hz, 1H), 7.68-7.64 (m, 1H), 7.54 (s, 1H), 7.41 (s, 1H), 7.20-7.14 (m, 1H), 6.50-6.30 (m, 3H), 5.76 (m, 1H), 3.99 (s, 3H), 3.92 (m, 2H), 3.91 (s, 3H), 3.76-3.64 (m, 2H), 2.78-2.74 (m, 2H), 2.53 (s, 3H), 2.22-2.18 (m, 2H), 1.86-1.82 (m, 2H); MS (ESI) (m/z): [M+H]⁺ 525.2.

The synthesis route of compounds 39a-39f is as shown in Scheme 4:

Scheme 4

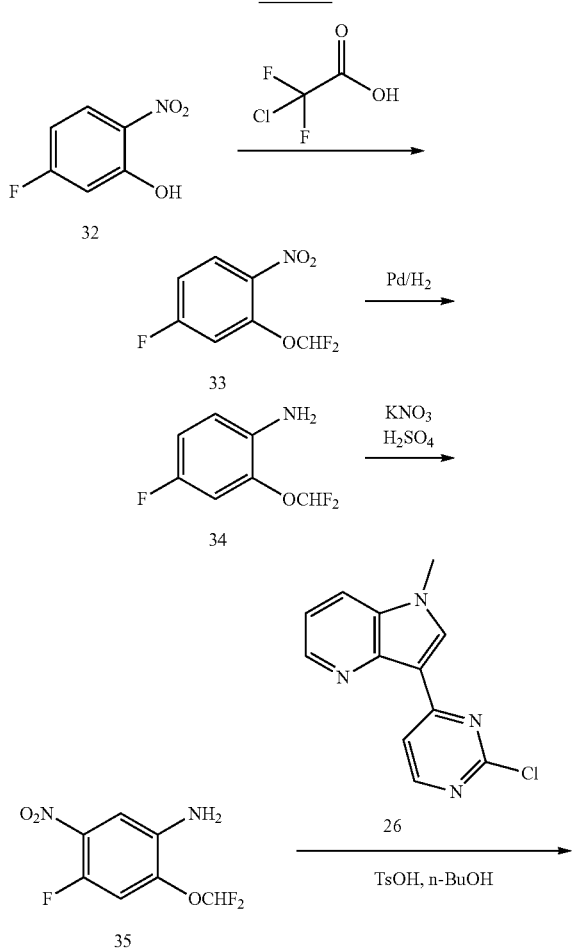

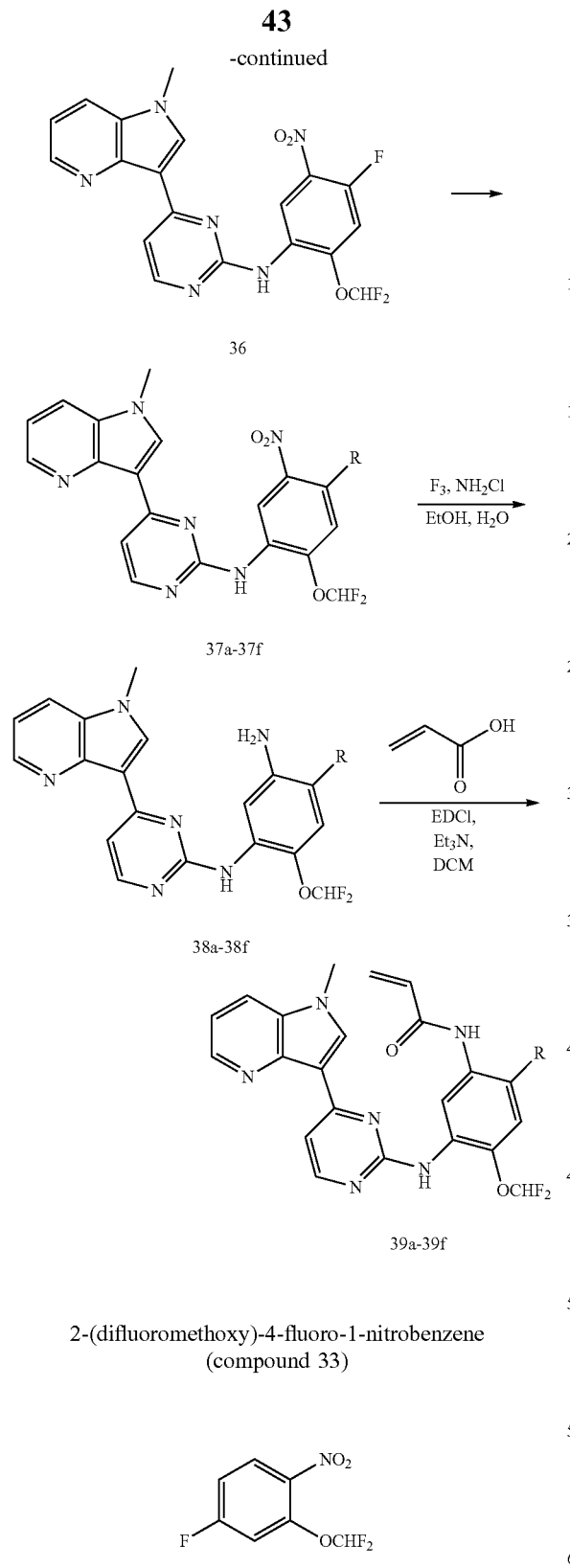

reaction solution was poured slowly into ice water (200 mL), and extracted with ethyl acetate (100 mL, 2 times). The organic phase was washed twice with saturate brine, dried over an appropriate amount of sodium sulfate, purified by column chromatography, and finally yellow oily target product 33 (11 g, 83.44%) was obtained. $^1$H NMR (400 MHz, CDCl$_3$): δ 8.08-8.04 (m, 1H), 7.21-7.09 (m, 2H), 6.88-6.48 (m, 1H); MS (ESI) (m/z): [M+H]$^+$ 208.0.

2-(difluoromethoxy)-4-fluoro-1-anilline (compound 34)

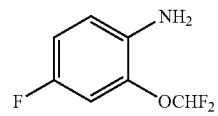

Compound 33 (11 g, 53.11 mmol) was dissolved in ethanol (100 mL), and Pd/C (2.2 g) was added. The system was replaced 3 times with H$_2$. Hydrogen was charged using a balloon of hydrogen, and the mixture was reacted overnight at room temperature. As post-treatment, the mixture was filtered with suction through celite, and the filtrate was spin-dried directly to obtain relatively pure product 34 (9.0 g, 95.74%) as a brown oil. $^1$H NMR (400 MHz, CDCl$_3$) δ 6.89-6.83 (m, 1H), 6.83-6.71 (m, 2H), 6.70-6.31 (m, 1H), 3.59 (s, 2H); MS (ESI) (m/z): [M+H]$^+$ 178.0.

2-(difluoromethoxy)-4-fluoro-5-nitroaniline (compound 35)

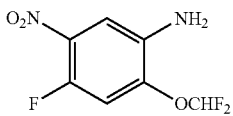 [SMILES: Nc1cc([N+](=O)[O-])c(F)cc1OC(F)F]

Compound 34 (9 g, 50.8 mmol) was dissolved in concentrated sulfuric acid (100 mL), cooled in an ice water bath, and potassium nitrate (5.14 g, 50.8 mmol) was added slowly. The reaction was complete in 1 h. The reaction solution was poured into ice water to quench the reaction. The mixture was extracted with dichloromethane, dried over sodium sulfate, and purified by column chromatography to obtain target product 35 (10.4 g, 92.15%) as an orange-red solid. MS (ESI) (m/z): [M+H]$^+$ 223.0.

N-(2-(difluoromethoxy)-4-fluoro-5-nitrophenyl)-4-(1-methyl-1H-pyrrolo[3,2-b]pyridin-3-yl)pyrimidin-2-amine (compound 36)

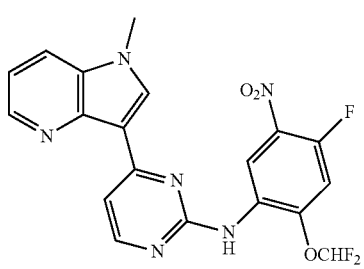 [SMILES: Cn1cc(-c2ccnc(Nc3cc([N+](=O)[O-])c(F)cc3OC(F)F)n2)c2ncccc21]

2-(difluoromethoxy)-4-fluoro-1-nitrobenzene (compound 33)

Compound 32 (10 g, 63.7 mmol) was dissolved in DMF (100 mL), uniformly stirred, and sodium carbonate (40.5 g, 382.1 mmol) was added. After the mixture was heated to 90° C. in an oil bath, chlorodifluoroacetic acid (29.1 g, 223.0 mmol) was added slowly. The reaction was monitored by TLC and was complete after 1 h. As post-treatment, the Compound 26 (1.2 g, purity 60%, 2.95 mmol) was dissolved in sec-pentanol (30 mL), and p-toluene sulfonic acid (760 mg, 4.4 mmol) and compound 35 (650 mg, 2.95 mmol) were added sequentially. The mixture was heated to 110° C. to react for 4 h. After the completion of reaction, the system was cooled to room temperature, and stirring was continued for 30 min before filtration. The solid precipitant was washed with a small amount of sec-pentanol to obtain undried yellow crude product compound 36. The crude product was slurried with an appropriate amount of acetonitrile and filtered to obtain compound 36 (800 mg, 63%) as a light yellow solid. MS (ESI) (m/z): [M+H]$^+$ 431.1.

2-(difluoromethoxy)-N$^4$-(2-(dimethylamino)ethyl)-N$^4$-methyl-N$^1$-(4-(1-methyl-1H-pyrrolo[3,2-b]pyridin-3-yl)pyrimidin-2-yl)-5-nitrobenzene-1,4-diamine (compound 37a)

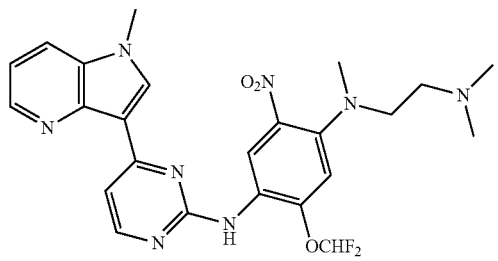 [SMILES: CN(C)CCN(C)c1cc(OC(F)F)c(Nc2nccc(-c3cn(C)c4cccnc34)n2)cc1[N+](=O)[O-]]

N,N-diisopropylethylamine (233 mg, 1.80 mmol) and N,N,N'-trimethylethylenediamine (170 mg, 1.67 mmol) were added sequentially to a solution of compound 36 (600 mg, 1.39 mmol) in N,N-dimethylacetamide (15 mL) at room temperature. The mixture was heated to 80° C. to react for 2 h. After the completion of reaction, ethyl acetate and water were added. The mixture was fully stirred and filtered over celite. The organic phase was washed several times with saturated brine, dried and concentrated to obtain compound 37a (680 mg, 96%) as a dark red solid. $^1$H NMR (400 MHz, CDCl$_3$): δ 9.68 (s, 1H), 8.62-8.58 (m, 1H), 8.48 (s, 1H), 8.44 (d, J=5.2 Hz, 1H), 8.28 (d, J=5.2 Hz, 1H), 7.70-7.64 (m, 1H), 7.36 (s, 1H), 7.23-7.19 (m, 1H), 7.01 (s, 1H), 6.67 (t, J=72 Hz, 1H), 3.95 (s, 3H), 3.23 (t, J=7.2 Hz, 2H), 2.88 (s, 3H), 2.54 (t, J=7.2 Hz, 2H), 2.26 (s, 6H); MS (ESI) (m/z): [M+H]$^+$ 513.2.

5-(difluoromethoxy)-N$^1$-(2-(dimethylamino)ethyl)-N$^1$-methyl-N$^4$-(4-(1-methyl-1H-pyrrolo[3,2-b]pyridin-3-yl)pyrimidin-2-yl)benzene-1,2,4-triamine) (compound 38a)

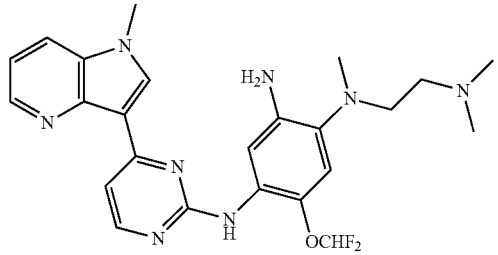

Compound 37a (700 mg, 1.37 mmol) was dissolved in ethanol (15 mL)/H$_2$O (5 mL), and iron powder (460 mg, 8.2 mmol) and ammonium chloride (50 mg, 0.96 mmol) were added. The reaction system was heated to reflux and reacted for 2 h. After the completion of reaction, the reactant was poured into a solution of dichloromethane:methanol=10:1, and an appropriate amount of water was added and stirred. The mixture was filtered over celite. The organic phase was dried and concentrated, and purified by column chromatography to obtain a light yellow solid 38a (300 ng, 45%). $^1$H NMR (400 MHz, CDCl$_3$): δ 8.63-8.59 (m, 1H), 8.45 (d, J=5.2 Hz, 1H), 8.24-8.18 (m, 2H), 8.05 (s, 1H), 7.70-7.65 (m, 1H), 7.28 (s, 1H), 7.23-7.18 (m, 1H), 6.88 (s, 1H), 6.44 (t, J=72 Hz, 1H), 3.89 (s, 3H), 2.95 (t, J=7.2 Hz, 2H), 2.66 (s, 3H), 2.45 (t, J=7.2 Hz, 2H), 2.30 (s, 6H); MS (ESI) (m/z): [M+H]$^+$ 483.2.

Example 18: N-(4-(difluoromethoxy)-2-((2-(dimethylamino)ethyl)(methyl)amino)-5-((4-((1-methyl-1H-pyrrolo[3,2-b]pyridin-3-yl)pyrimidin-2-yl)amino)phenyl)acrylamide (compound 39a)

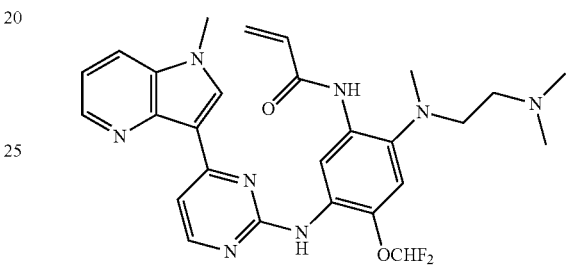

Compound 38a (120 mg, 0.25 mmol) was dissolved in dichloromethane (10 mL)/tert-butanol (1 mL), and triethylamine (50 mg, 0.50 mmol), EDCI (96 mg, 0.50 mmol), and acrylic acid (36 mg, 0.50 mmol) were added sequentially at 0-5° C. The mixture was stirred for 2 h at room temperature, and an appropriate amount of ethyl acetate was added. The organic phase was washed with water. The organic phase was dried and concentrated, and purified by column chromatography to obtain a whitish solid 39a (60 mg, 45%). $^1$H NMR (400 MHz, CDCl$_3$): δ 10.36 (be, 1H), 10.01 (s, 1H), 9.47 (bs, 1H), 8.62-8.58 (m, 1H), 8.44 (d, J=5.2 Hz, 1H), 8.30 (d, J=5.2 Hz, 1H), 7.70-7.65 (m, 1H), 7.51 (s, 1H), 7.21-7.15 (m, 1H), 7.07 (s, 1H), 6.68-6.32 (m, 3H), 5.76 (m, 1H), 4.01 (s, 3H), 2.86 (t, J=7.2 Hz, 2H), 2.70 (s, 3H), 2.32-2.22 (m, 8H); MS (ESI) (m/z): [M+H]$^+$ 537.2.

N-(2-(difluoromethoxy)-4-(4-methylpiperazin-1-yl)-5-nitrophenyl)-4-(1-methyl-1H-pyrrol o[3,2-b]pyridin-3-yl)pyrimidin-2-amine (compound 37b)

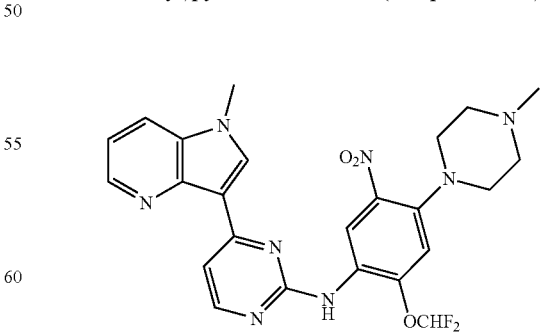

Compound 376 was prepared in the same manner as compound 37a, except that 4-methylpiperazine was used instead of N,N,N'-trimethylethylenediamine. MS (ESI) (m/z): [M+H]$^+$ 511.2.

6-(difluoromethoxy)-N¹-(4-(1-methyl-1H-pyrrolo[3,2-b]pyridin-3-yl)pyrimidin-2-yl)-4-(4-methylpiperazin-1-yl)benzene-1,3-diamine (compound 38b)

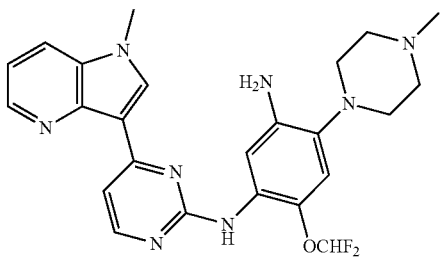 [SMILES: CN1CCN(c2cc(OC(F)F)c(Nc3nccc(-c4cn(C)c5cccnc45)n3)cc2[N+](=O)[O-])CC1]

Compound 38b was prepared in the same manner as compound 38a, except that compound 37b was used instead of compound 37a. ¹H NMR (400 MHz, CDCl$_3$): δ 8.64-8.60 (m, 1H), 8.45 (d, J=5.2 Hz, 1H), 8.24-8.18 (m, 2H), 8.09 (s, 1H), 7.71-7.67 (m, 1H), 7.27 (s, 1H), 7.22-7.18 (m, 1H), 6.88 (s, 1H), 6.43 (t, J=72 Hz, 1H), 4.04 (bs, 2H), 3.91 (s, 3H), 2.92 (m, 4H), 2.58 (m, 4H), 2.37 (s, 3H); MS (ESI) (m/z): [M+H]⁺ 481.2.

Example 19: N-(4-(difluoromethoxy)-5-((4-(1-methyl-1H-pyrrolo[3,2-b]pyridin-3-yl)pyrimidin-2-yl)amino)-2-(4-methylpiperazin-1-yl)phenyl)acrylamide (compound 39b)

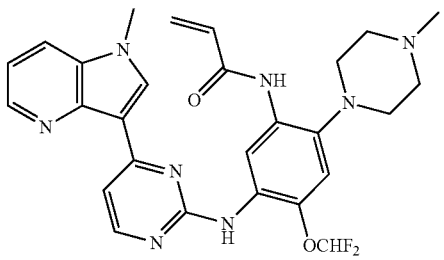 [SMILES: C=CC(=O)Nc1cc(Nc2nccc(-c3cn(C)c4cccnc34)n2)c(OC(F)F)cc1N1CCN(C)CC1]

Compound 39b was prepared in the same manner as compound 39a, except that compound 38b was used instead of compound 38a. ¹H NMR (400 MHz, CDCl$_3$): δ 9.96 (bs, 1H), 9.38 (s, 1H), 8.85 (bs, 1H), 8.62-8.58 (m, 1H), 8.44 (d, J=5.2 Hz, 1H), 8.32 (d, J=5.2 Hz, 1H), 7.70-7.56 (m, 1H), 7.50 (s, 1H), 7.20-7.16 (m, 1H), 7.05 (m, 1H), 6.70-6.30 (m, 3H), 5.82 (m, 1H), 4.00 (s, 3H), 2.92 (m, 4H), 2.62 (m, 4H), 2.41 (s, 3H); MS (ESI) (m/z): [M+H]⁺ 535.2.

N-(2-(difluoromethoxy)-4-(3-(dimethylamino)azetidin-1-yl)-5-nitrophenyl)-4-(1-methyl-1H-pyrrolo[3,2-b]pyridin-3-yl)pyrimidin-2-amine (compound 37c)

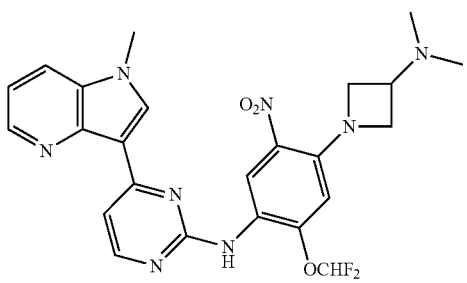 [SMILES: CN(C)C1CN(c2cc(OC(F)F)c(Nc3nccc(-c4cn(C)c5cccnc45)n3)cc2[N+](=O)[O-])C1]

Compound 37c was prepared in the same manner as compound 37a, except that N,N-dimethylazetidin-3-amine was used instead of N,N,N'-trimethylethylenediamine. ¹H NMR (400 MHz, CDCl$_3$): δ 9.81 (s, 1H), 8.65-8.63 (m, 1H), 8.62 (s, 1H), 8.48 (d, J=5.2 Hz, 1H), 8.32 (d, J=5.2 Hz, 1H), 7.74-7.71 (m, 1H), 7.34 (s, 1H), 7.27-7.23 (m, 1H), 6.66 (t, J=72.4 Hz, 1H), 6.43 (s, 1H), 4.16 (t, J=7.7 Hz, 2H), 4.00 (s, 3H), 3.76-3.72 (m, 2H), 3.28-3.18 (m, 1H), 2.24 (s, 6H); MS (ESI) (m/z): [M+H]⁺ 511.2.

6-(difluoromethoxy)-4-(3-(dimethylamino)azetidin-1-yl)-N¹-(4-(1-methyl-1H-pyrrolo[3,2-b]pyridin-3-yl)pyrimidin-2-yl)benzene-1,3-diamine compound 38c)

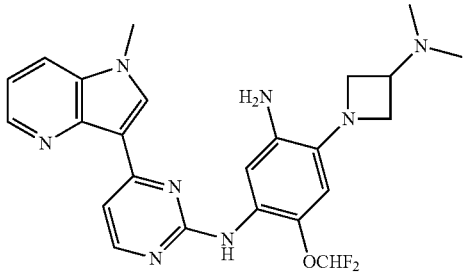

Compound 38c was prepared in the same manner as compound 38a, except that compound 37c was used instead of compound 37a. MS (ESI) (m/z): [M+H]⁺ 481.2.

Example 20: N-(4-(difluoromethoxy)-2-(3-(dimethylamino)azetidin-1-yl)-5-((4-(1-methyl-1H-pyrrolo[3,2-b]pyridin-3-yl)pyrimidin-2-yl)amino)phenyl)acrylamide (compound 39c)

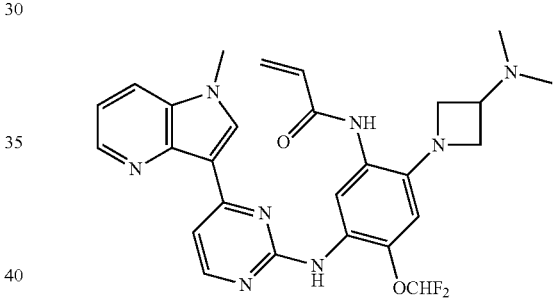

Compound 39c was prepared in the same manner as compound 39a, except that compound 38c was used instead of compound 38a. ¹H NMR (400 MHz, CDCl$_3$): δ 9.56 (s, 1H), 9.25 (s, 1H), 8.62 (d, J=3.8 Hz, 1H), 8.46 (d, J=5.2 Hz, 1-1), 8.30 (d, J=5.2 Hz, 1H), 7.82 (s, 1H), 7.71 (d, J=8.3 Hz, 1H), 7.41 (s, 1H), 7.23-7.21 (m, 1H), 6.80 (s, 1H), 6.77-6.33 (m, 3H), 5.85 (d, J=8.9 Hz, 1H), 4.03 (s, 3H), 3.90 (t, J=6.5 Hz, 2H), 3.66 (t, J=6.6 Hz, 2H), 3.28-3.14 (m, 1H), 2.28 (s, 6H); MS (ESI) (m/z): [M+H]⁺ 535.2.

N-(2-(difluoromethoxy)-4-(4-(dimethylamino)piperidin-1-yl)-5-nitrophenyl)-4-(1-methyl-1H-pyrrolo[3,2-b]pyridin-3-yl)pyrimidin-2-amine (compound 37d)

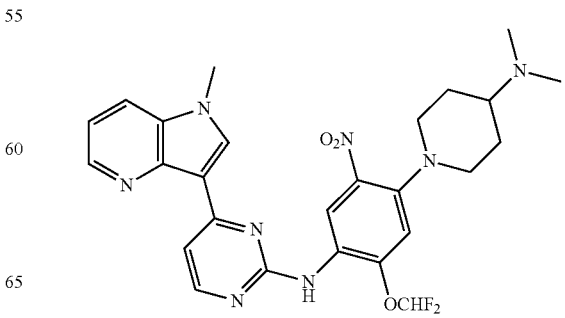

Compound 37d was prepared in the same manner as compound 37a, except that N,N-dimethylpiperidin-4-amine was used instead of N,N,N'-trimethylethylenediamine. $^1$H NMR (400 MHz, CDCl$_3$): δ 9.78 (s, 1H), 8.63-8.59 (m, 1H), 8.53 (s, 1H), 8.46 (d, J=5.2 Hz, 1H), 8.30 (d J=5.2 Hz, 1H), 7.73-7.65 (m, 1H), 7.42 (s, 1H), 7.25-7.19 (m, 1H), 6.92 (s, 1H), 6.65 (t, J=72 Hz, 1H), 3.95 (s, 3H), 3.32 (m, 2H), 2.82 (m, 2H), 2.44-2.22 (m, 7H), 1.98-1.74 (m, 4H); MS (ESI) (m/z): [M+H]$^+$ 539.2.

6-(difluoromethoxy)-4-(4-(dimethylamino)piperidin-1-yl)-N$^1$-(4-(1-methyl-1H-pyrrolo[3,2-b]pyridin-3-yl)pyrimidin-2-yl)benzene-1,3-diamine (compound 38d)

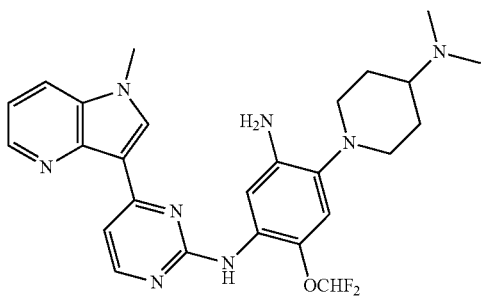 [SMILES: CN(C)C1CCN(c2cc(OC(F)F)c(Nc3nccc(-c4cn(C)c5cccnc45)n3)cc2[N+](=O)[O-])CC1]

Compound 38d was prepared in the same manner as compound 38a, except that compound 37d was used instead of compound 37a. $^1$H NMR (400 MHz, CDCl$_3$): δ 8.62-8.58 (m, 1H), 8.44 (d, J=5.2 Hz, 1H), 8.22-8.16 (m, 2H), 8.05 (s, 1H), 7.68-7.63 (m, 1H), 7.28 (s, 1H), 7.23-7.17 (m, 1H), 6.83 (s, 1H), 6.44 (t. J=72 Hz, 1H), 4.05 (bs, 2H), 3.87 (s, 3H), 3.18 (m, 2H), 2.64-2.54 (m, 2H), 2.34 (s, 6H), 2.26 (m, 1H), 1.95 (m, 2H), 1.68 (m, 2H); MS (ESI) (m/z): [M+H]$^+$ 509.2.

Example 21: N-(4-(difluoromethoxy)-2-(4-(dimethylamino)piperidin-1-yl)-5-((4-(1-methyl-1H-pyrrolo[3,2-b]pyridin-3-yl)pyrimidin-2-yl)amino)phenyl)acrylamide (compound 39d)

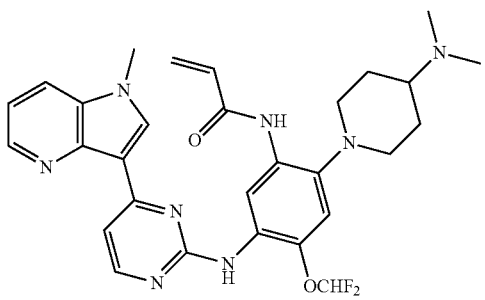 [SMILES: C=CC(=O)Nc1cc(Nc2nccc(-c3cn(C)c4cccnc34)n2)c(OC(F)F)cc1N1CCC(N(C)C)CC1]

Compound 39d was prepared in the same manner as compound 39a, except that compound 38d was used instead of compound 38a. $^1$H NMR (400 MHz, CDCl$_3$): δ 9.95 (s, 1H), 9.40 (s, 1H), 8.84 (s, 1H), 8.62-8.58 (m, 1H), 8.44 (d, J=5.2 Hz, 1H), 8.30 (d, J=5.2 Hz, 1H), 7.71-7.65 (m, 1H), 7.49 (s, 1H), 7.20-7.16 (m, 1H), 7.02 (s, 1H), 6.70-6.30 (m, 3H), 5.80 (m, 1H), 4.01 (s, 3H), 3.07-3.03 (m, 2H), 2.76-2.70 (m, 2H), 2.36 (s, 6H), 2.19 (m, 1H), 2.04 (m, 2H), 1.64 (m, 2H); MS (ESI) (m/z): [M+H]$^+$ 563.2.

(S)—N-(2-(difluoromethoxy)-4-(2-((dimethylamino)methy)pyrrol-1-yl)-5-nitrophenyl)-4-(1-methyl-1H-pyrrolo[3,2-b]pyridin-3-yl)pyrimidin-2-amine (compound 37e)

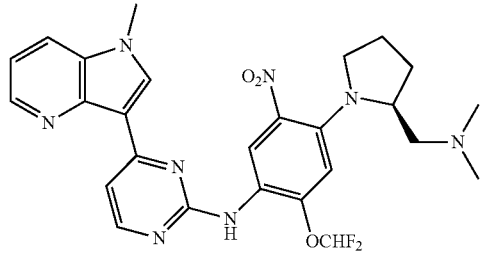 [SMILES: CN(C)C[C@@H]1CCCN1c1cc(OC(F)F)c(Nc2nccc(-c3cn(C)c4cccnc34)n2)cc1[N+](=O)[O-]]

Compound 37e was prepared in the same manner as compound 37a, except that (S)—N,N-dimethyl-1-(pyrrolidin-2-yl)-methanamine was used instead of N,N,N'-trimethylethylenediamine. $^1$H NMR (400 MHz, CDCl$_3$): δ 9.75 (s, 1H), 8.66-8.64 (m, 1H), 8.61 (s, 1H), 8.49 (d, J=5.2 Hz, 1H), 8.31 (d, J=5.2 Hz, 1H), 7.74-7.72 (m, 1H), 7.35 (s, 1H), 7.26-7.24 (m, 1H), 7.07 (s, 1H), 6.71 (t, J=72.4 Hz, 1H), 4.01 (s, 3H), 3.64-3.60 (m, 1H), 2.75-2.59 (m, 2H), 2.48-2.28 (m, 8H), 2.09-1.74 (m, 4H); MS (ESI) (m/z): [M+H]$^+$ 539.2.

(S)-6-(difluoromethoxy)-4-(2-((dimethylamino)methyl)pyrrolidin-1-yl)-N$^1$-(4-(1-methyl-1H-pyrrolo[3,2-b]pyridin-3-yl)pyrimidin-2-yl)benzene-1,3-diamine (compound 38e)

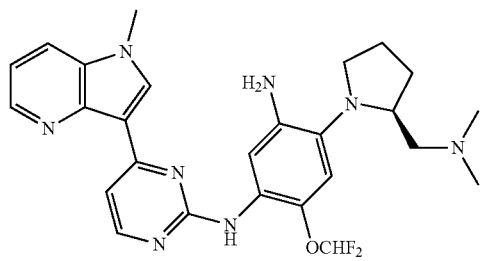 [SMILES: CN(C)C[C@@H]1CCCN1c1cc(OC(F)F)c(Nc2nccc(-c3cn(C)c4cccnc34)n2)cc1N]

Compound 38e was prepared in the same manner as compound 38a, except that compound 37e was used instead of compound 37a. MS (ESI) (m/z): [M+H]$^+$ 509.3.

Example 22: (S)—N-(4-(difluoromethoxy)-2-(2-((dimethylamino)methyl) pyrrolidin-1-yl)-5-((4-(1-methyl-1H-pyrrolo[3,2-b]pyridin-3-yl)pyrimidin-2-yl)amino)phenyl)acrylamide (compound 39e)

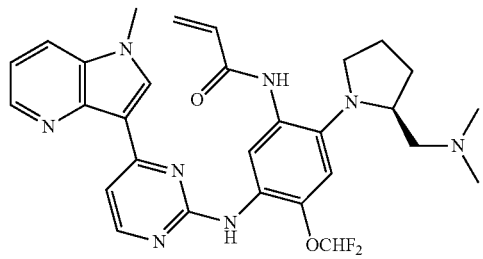 [SMILES: C=CC(=O)Nc1cc(Nc2nccc(-c3cn(C)c4cccnc34)n2)c(OC(F)F)cc1N1CCC[C@H]1CN(C)C]

Compound 39e was prepared in the same manner as compound 39a, except that compound 38e was used instead of compound 38a. ¹H NMR (400 MHz, CDCl₃) δ 9.82 (s, 1H), 9.73 (s, 1H), 9.28 (s, 1H), 8.59-8.58 (m, 1H), 8.43 (d, J=5.2 Hz, 1H), 8.30 (d, J=5.2 Hz, 1H), 7.69-7.67 (m, 1H), 7.53 (d, J=18.2 Hz, 1H), 7.20-7.18 (m, 1H), 7.03 (s, 1H), 6.93 (s, 1H), 6.82-6.39 (m, 2H), 5.81-5.78 (m, 1H), 3.98 (s, 3H), 3.81-3.59 (m, 2H), 2.90-2.84 (m, 2H), 2.56 (s, 6H), 2.24-2.20 (m, 1H), 2.10-1.72 (m, 4H); MS (ESI) (m/z): [M+H]⁺ 563.3.

N-(2-(difluoromethoxy)-4-(5-methyl-2,5diazaspiro [3.4]oct-2-yl)-5-nitrophenyl)-4-(1-meth yl-1H-pyrrolo[3,2-b]pyridin-3-yl)pyrimidin-2-amine (compound 37f)

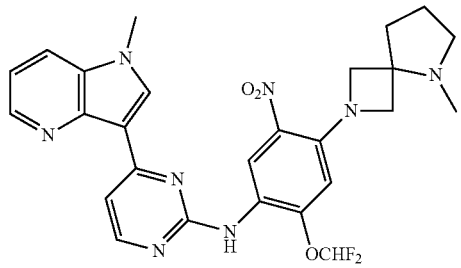

Compound 37f was prepared in the same manner as compound 37a, except that 5-methyl-2,5-diazaspiro[3.4]octane was used instead of N,N,N'-trimethylethylenediamine. ¹H NMR (400 MHz, CDCl₃): δ 9.74 (s, 1H), 8.64-8.58 (m, 1H), 8.58 (s, 1H), 8.44 (d, J=5.2 Hz, 1H), 8.28 (d, J=5.2 Hz, 1H), 7.72-7.64 (m, 1H), 7.28 (s, 1H), 7.24-7.18 (m, 1H), 6.64 (t, J=72 Hz, 1H), 6.40 (s, 1H), 4.10 (m, 2H), 3.90 (s, 3H), 3.70 (m, 2H), 2.74 (m, 2H), 2.50 (s, 3H), 2.12 (m, 2H), 1.81 (m, 2H); MS (ESI) (m/z): [M+H]⁺ 537.2.

6-(difluoromethoxy)-N¹-(4-(1-methyl-1H-pyrrolo[3,2-b]pyridin-3-yl)pyrimidin-2-yl)-4-(5-methyl-2,5diazaspiro[3.4]oct-2-yl)benzene-1,3-diamine (compound 38f)

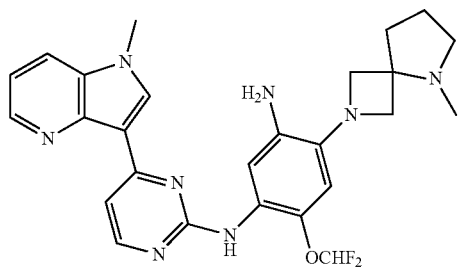 [SMILES: CN1CCCC12CN(c1cc(OC(F)F)c(Nc3nccc(-c4cn(C)c5cccnc45)n3)cc1[N+](=O)[O-])C2]

Compound 38f was prepared in the same manner as compound 38a, except that compound 37f was used instead of compound 37aj. ¹H NMR (400 MHz, CDCl₃): 8.63-8.59 (m, 1H), 8.43 (d, J=5.2 Hz, 1H), 8.24-8.16 (m, 2H), 7.93 (s, 1H), 7.69-7.65 (m, 1H), 7.23-7.18 (m, 1H), 7.15 (s, 1H), 6.50 (s, 1H), 6.45 (t, J=72 Hz, 1H), 3.94-3.84 (m, 5H), 3.60 (m, 2H), 2.74 (m, 2H), 2.50 (s, 3H), 2.18 (m, 2H), 1.81 (m, 2H); MS (ESI) (m/z): [M+H]⁺ 507.2.

Example 23: N-(4-(difluoromethoxy)-5-((4-(1-methyl-1H-pyrrolo[3,2-b]pyridin-3-yl)pyrimidin-2-yl)amino)-2-(5-methyl-2,5diazaspiro[3.4]oct-2-yl) phenyl)acryl amide (compound 39f)

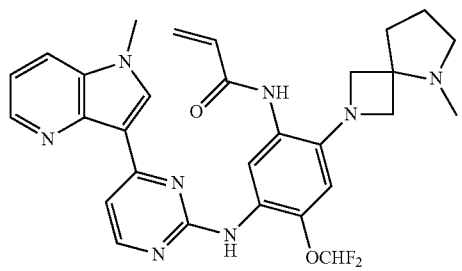 [SMILES: C=CC(=O)Nc1cc(Nc2nccc(-c3cn(C)c4cccnc34)n2)c(OC(F)F)cc1N1CC2(CCCN2C)C1]

Compound 39f was prepared in the same manner as compound 39a, except that compound 38f was used instead of compound 38a. ¹H NMR (400 MHz, CDCl₃): δ 9.40 (bs, 1H), 9.16 (s, 1H), 8.62-8.58 (m, 1H), 8.42 (d, J=5.2 Hz, 1H), 8.26 (d, J=5.2 Hz, 1H), 7.71-7.65 (m, 1H), 7.50 (s, 1H), 7.32 (s, 1H), 7.20-7.15 (m, 1H), 6.74-6.30 (m, 4H), 5.82 (m, 1H), 3.98 (s, 3H), 3.95-3.92 (m, 2H), 3.64-3.62 (m, 2H), 2.81-2.77 (m, 2H), 2.53 (s, 3H), 2.22-2.18 (m, 2H), 1.86-1.82 (m, 2H); MS (ESI) (m/z): [M+H]⁺ 561.2.

The synthesis route of compounds 51a-51f is as shown in Scheme 5:

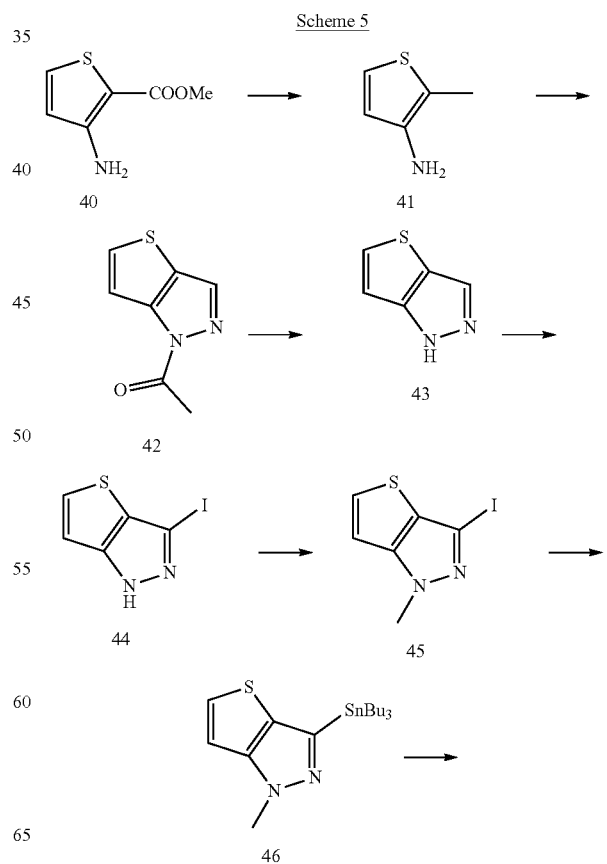

53
-continued

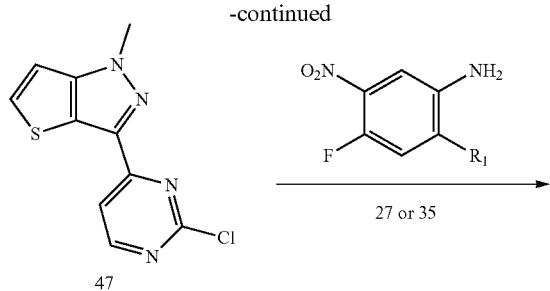

48a-48b

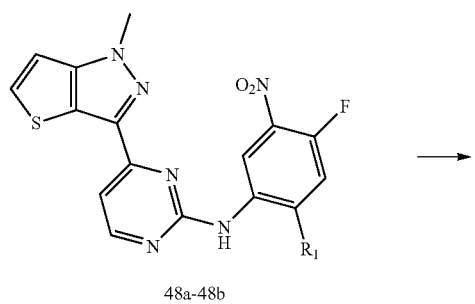

49a-49f

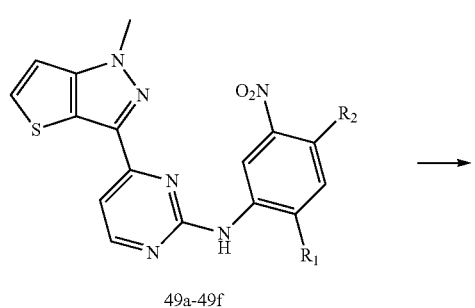

50a-50f

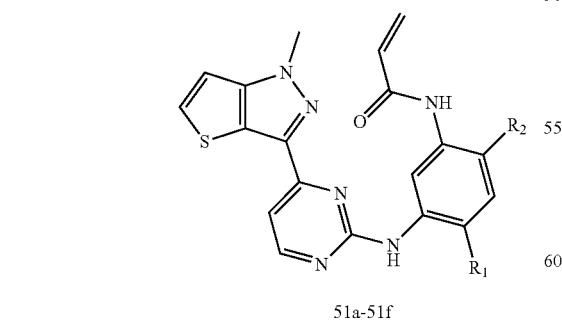

51a-51f

For the synthesis of compound 43, ee reference Synthesis (Germany) 2014, Vol. 46, p. 96-100, and for the synthesis of compound 46, see patent application WO 2013030138.

54

3-(2-chloropyrimidin-4-yl)-1-methyl-1H-thieno[3,2-c]pyrazole (compound 47)

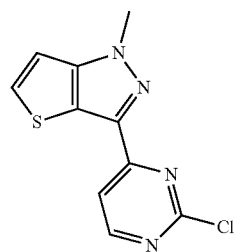 [SMILES: Cn1nc(-c2ccnc(Cl)n2)c2sccc21]

1-methyl-(tributyltin)-1H-thieno[3,2-c]pyrazole 46 (1.5 g, 3.5 mmol) was dissolved in DMF (50 mL) in a 100 mL single neck flask, and 2,4-dichloropyrimidine (0.778 g, 5.3 mmol), copper iodide (0.138 g, 0.7 mmol), and tetrakis (triphenylphosphine)palladium (0.202 g, 0.175 mmol) were added. The mixture was reacted for 1 hour under nitrogen at 80° C. Water was added to quench the reaction. The mixture was extracted with ethyl acetate for 3 times, dried over sodium sulfate, concentrated, and subjected to column chromatography to obtain product (0.8 g, 3.2 mmol). MS (ESI) [M+H]$^+$ 251.1.

N-(4-fluoro-2-methoxy-5-nitrophenyl)-4-(1-methyl-1H-thieno[3,2-c]pyrazol-3-yl)pyrimidin-2-amine (compound 48a)

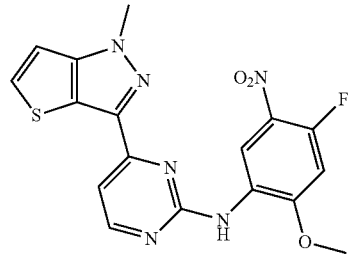 [SMILES: COc1cc(F)c([N+](=O)[O-])cc1Nc1nccc(-c2nn(C)c3ccsc23)n1]

Compound 47 (600 mg, 2.4 mmol) was dissolved in 2-pentanol (50 mL) in a 100 mL single neck flask, and compound 27 (580 mg, 3.1 mmol) and p-toluene sulfonic acid (1.2 g, 7.2 mmol) were added. The mixture was reacted for 3 h at 110° C. Water was added to quench the reaction. The mixture was extracted with ethyl acetate for 3 times, dried over sodium sulfate, concentrated, and subjected to column chromatography to obtain product (300 mg, 0.75 mmol). MS (ESI) (m/z): [M+H]$^+$ 401.1.

N-(2-(difluoromethoxy)-4-fluoro-5-nitrophenyl)-4-(1-methyl-1H-thieno[3,2-c]pyrazol-3-yl)pyrimidin-2-amine (compound 48b)

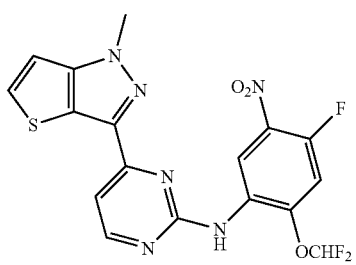 [SMILES: Cn1nc(-c2ccnc(Nc3cc([N+](=O)[O-])c(F)cc3OC(F)F)n2)c2sccc21]

Compound 48b was prepared in the same manner as compound 48a, except that compound 35 was used instead of compound 27. MS (ESI) [M+H]⁺ 437.1.

N¹-(2-(dimethylamino)ethyl)-5-methoxy-M-methyl-N⁴-(4-(1-methyl-1H-thieno[3,2-c]pyrazol-3-yl)pyrimidin-2-yl)-2-nitrobenzene-1,4-diamine (compound 49a)

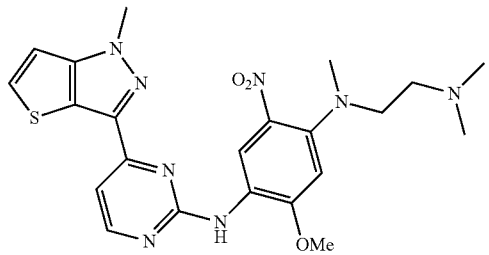

Compound 48a (400 mg, 1.0 mmol) was dissolved in dimethylacetamide (50 mL) in a 100 mL single neck flask, and N,N,N'-trimethylethylenediamine (153 mg, 1.5 mmol) and N,N-diisopropylethylamine (387 mg, 3.0 mmol) were added. The mixture was reacted for 2 h at 80° C. Water was added to quench the reaction. The mixture was extracted with ethyl acetate for 3 times, dried over sodium sulfate, concentrated, and subjected to column chromatography to obtain compound 49a (300 mg, 0.622 mmol). MS (EST) (m/z): [M+H]⁺ 483.3.

N¹-(2-(dimethylamino)ethyl)-5-methoxy-N¹-methyl-N⁴-(4-(1-methyl-1H-thieno[3,2-c]pyrazol-3-yl)pyrimidin-2-yl)benzene-1,2,4-triamine (compound 50a)

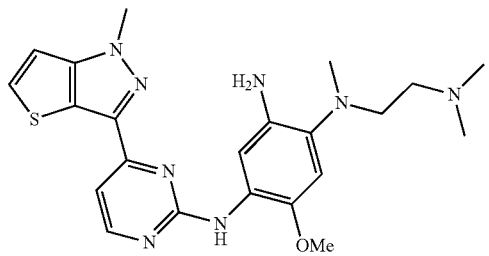 [SMILES: COc1cc(N(C)CCN(C)C)c([N+](=O)[O-])cc1Nc1nccc(-c2nn(C)c3ccsc23)n1]

Compound 49a (300 mg, 0.622 mmol) was dissolved in ethanol (20 ml) in a 100 mL single neck flask, and saturated ammonium chloride solution (20 ml) and iron powder (174 mg, 3.11 mmol) were added. The mixture was reacted for 2 h at 50° C. 50 mL of water was added. The mixture was extracted with ethyl acetate for 3 times, dried over sodium sulfate, concentrated, and subjected to column chromatography to obtain compound 50a (150 mg, 0.33 mmol). MS (ESI) (m/z): [M+H]⁺ 453.2.

Example 24: N-(2-((2-(dimethylamino)ethyl)(methyl)amino)-4-methoxy-5-((4-(1-methyl-1H-thieno[3,2-c]pyrazol-3-yl)pyrimidin-2-yl)amino)phenyl)acrylamide (compound 51a)

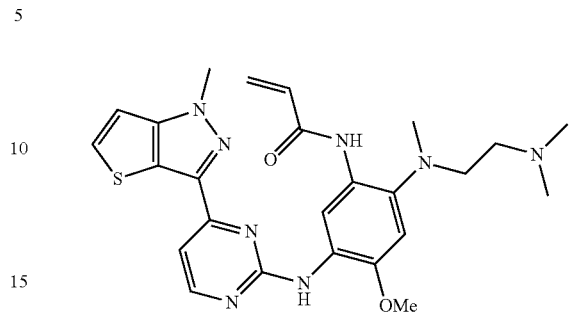

Compound 50a (150 mg, 0.33 mmol) was dissolved in 2.0 mL of dichloromethane in a 100 mL single neck flask, and acrylic, acid (28.7 mg, 0.39 mmol), EDCI (127 mg, 0.66 mmol), and triethylamine (100 mg, 0.99 mmol) were added. The mixture was reacted for 2 h at room temperature. Water (30 mL) was added. The mixture was extracted with dichloromethane for 3 times, dried over sodium sulfate, concentrated, and subjected to column chromatography to obtain compound 51a (30 rug, 0.059 mmol). ¹H NMR (400 MHz, CDCl₃): δ 10.20 (s, 1H), 9.47 (s, 1H), 8.57 (d, J=5.1 Hz, 1H), 7.62 (s, 1H), 7.43 (d, J=5.3 Hz, 1H), 7.37 (d, J=5.2 Hz, 1H), 6.93 (d, J=5.3 Hz, 1H), 6.81 (s, 1H), 6.45-6.39 (m, 2H), 5.70-5.67 (m, 1H), 4.13 (s, 3H), 3.90 (s, 3H), 2.93 (s, 2H), 2.74 (s, 3H), 2.26-2.33 (m, 8H), MS (ESI) [M+H]⁺ 507.2.

2-(difluoromethoxy)-N⁴-(2-(dimethylamino)ethyl)-N⁴-methyl-N¹-(4-(1-methyl-1H-thieno[3,2-c]pyrazol-3-yl)pyridin-2-yl)-5-nitrobenzene-1,4-diamine (compound 49b)

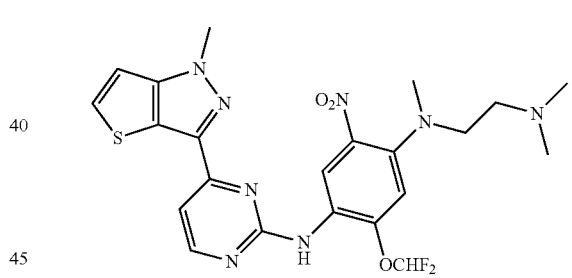

Compound 49b was prepared in the same manner as compound 49a, except that compound 48b was used instead of compound 48a. MS (ESI) (m/z): [M+H]⁺ 519.2.

5-(difluoromethoxy-N¹-(2-(dimethylamino)ethyl)-N¹-methyl-N⁴-(4-(1-methyl-1H-thieno[3,2-c]pyrazol-3-yl)pyrimidin-2-yl)benzene-1,2,4-triamine) (compound Sob)

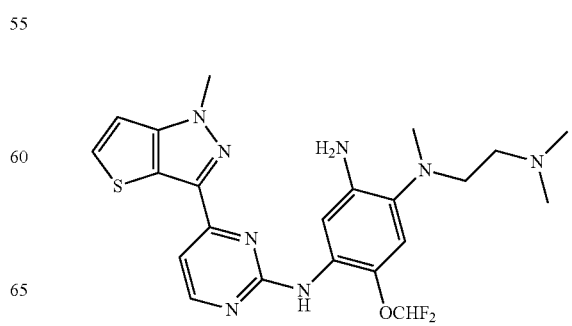

Compound 50I) was prepared in the same manner as compound 50a, except, that compound 49b was used instead of compound 49a. $^1$H NMR (400 MHz, CDCl$_3$): δ 8.47 (d, J=5.1 Hz, 1H), 7.73 (s, 1H), 7.39 (s, 1H), 7.35 (d, J=5.3 Hz, 1H), 7.11 (d, J=5.3 Hz, 1H), 6.93 (d, J=5.1 Hz, 1H), 6.86 (s, 1H), 6.45 (t, J=74.4 Hz, 1H), 4.43 (s, 3H), 3.00 (t, J=6.4 Hz, 2H), 2.66 (s, 3H), 2.61 (t, J=6.0 Hz, 2H), 2.42 (s, 6H). MS (ESI) (m/z): [M+H]$^+$ 489.2.

Example 25: N-(4-(difluoromethoxy)-2-((2-(dimethylamino)ethyl)methyl)amino)-5-((4-(1-methyl-1H-thieno[3,2-c]pyrazol-3-yl)pyrimidin-2-yl)amino) phenyl)acrylamide (compound 51b)

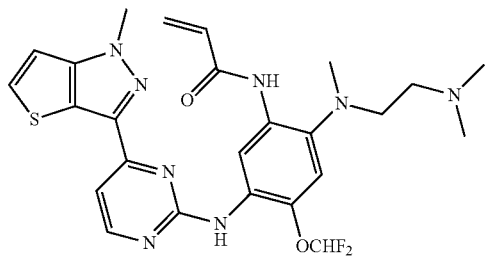 [SMILES: C=CC(=O)Nc1cc(Nc2nccc(-c3nn(C)c4ccsc34)n2)c(OC(F)F)cc1N(C)CCN(C)C]

Compound 51b was prepared in the same manner as compound 51a, except that compound 50b was used instead of compound 50a. $^1$H NMR (400 MHz, CDCl$_3$): δ 10.34 (s, 1H), 9.40 (s, 1H), 8.60 (d, J=5.2 Hz, 1H), 7.39 (d, J=5.4 Hz, 1H), 7.31 (s, 1H), 7.17 (d, J=5.4 Hz, 1H), 7.09 (s, 1H), 7.03 (d, J=5.2 Hz, 1H), 6.71-6.33 (m, 3H), 5.76-5.73 (m, 1H), 4.48 (s, 3H), 2.89-2.87 (m, 2H), 2.74 (s, 3H), 2.36-2.34 (m, 2H), 2.30 (s, 6H). MS (ESI) (m/z): [M+H]+ 543.3.

N-(2-(difluoromethoxy)-4-(4-methylpiperazin-1-yl)-5-nitrophenyl)-4-(1-methyl-1H-thieno[3,2-c]pyrazol-3-yl)pyrimidin-2-amine (compound 49c)

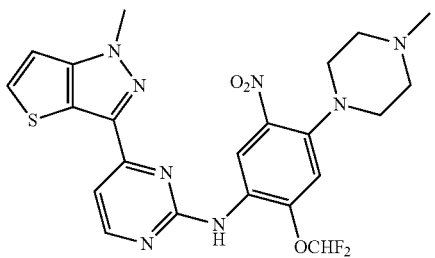

Compound 49c was prepared in the same manner as compound 49a, except that compound 48b was used instead of compound 48a, and 4-methylpiperazine was used instead of N,N,N'-trimethylethylenediamine. MS (ESI) (m/z): [M+H]$^+$ 517.1.

6-(difluoromethoxy)-N$^1$-(4-(1-methyl-1H-thieno[3,2-c]pyrazol-3-yl)pyrimidin-2-yl)-4-(4-methylpiperazin-1-yl)benzene-1,3-diamine compound 50c)

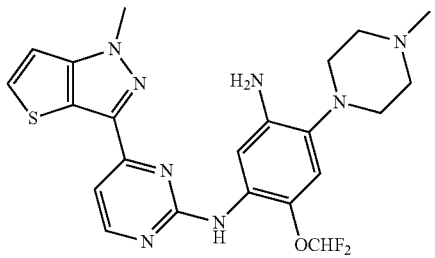 [SMILES: CN1CCN(c2cc(OC(F)F)c(Nc3nccc(-c4nn(C)c5ccsc45)n3)cc2N)CC1]

Compound 50c was prepared in the same manner as compound 50a, except that compound 49c was used instead of compound 49a. MS (ESI) (m/z): [M+H]$^+$ 487.1.

Example 26: N-(4-(difluoromethoxy)-5-((4-(1-methyl-1H-thieno[3,2-c]pyrazol-3-yl)pyrimidin-2-yl)amino)-2-(4-methylpiperazin-1-yl)phenyl)acrylamide (compound 51c)

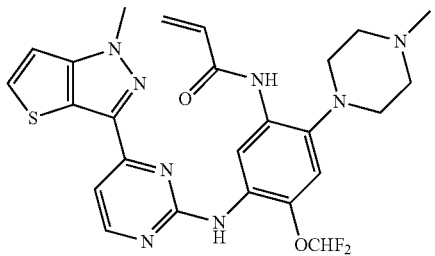 [SMILES: C=CC(=O)Nc1cc(Nc2nccc(-c3nn(C)c4ccsc34)n2)c(OC(F)F)cc1N1CCN(C)CC1]

Compound 5lc was prepared in the same manner as compound 51a, except that compound 50c was used instead of compound 50a. $^1$H NMR (400 MHz, CDCl$_3$): δ 9.36 (s, 1H), 8.62 (s, 1H), 8.58 (d, J=5.2 Hz, 1H), 7.36 (d, J=5.2 Hz, 1H), 7.31 (s, 1H), 7.14 (d, J=5.2 Hz, 1H), 7.06 (s, 1H), 7.02 (d, J=5.2 Hz, 1H), 6.50 (t, J=72 Hz, 1H), 6.44-6.22 (m, 2H), 5.82-5.78 (m, 1H), 4.47 (s, 3H), 2.93-2.89 (m, 4H), 2.64-2.60 (m, 4H), 2.39 (s, 3H); MS (ESI) (m/z): [M+H]$^+$ 541.2.

N-(2-(difluoromethoxy)-4-(3-(dimethylamino)azetidin-1-yl)-5-nitrophenyl)-4-(1-methyl-1H-thieno[3,2-c]pyrazol-3-yl)pyrimidin-2-amine (compound 49d)

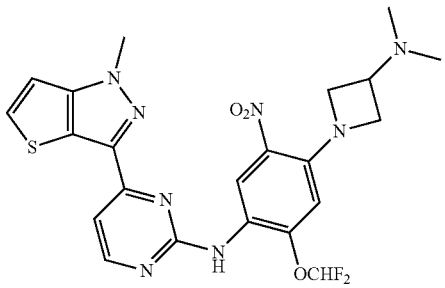 [SMILES: CN(C)C1CN(c2cc(OC(F)F)c(Nc3nccc(-c4nn(C)c5ccsc45)n3)cc2[N+](=O)[O-])C1]

Compound 49d was prepared in the same manner as compound 49a, except that compound 48b was used instead of compound 48a and N,N-dimethylazetidin-3-amine was used instead of N,N,N'-trimethylethylenediamine. $^1$H NMR (400 MHz, CDCl$_3$): δ 8.88 (s, 1H), 8.54 (d, J=5.2 Hz, 1H), 7.38 (d, J=5.2 Hz, 1H), 7.24 (s, 1H), 7.17 (d, J=5.2 Hz, 1H), 7.04 (d, J=5.2 Hz, 1H), 6.62 (t, J=72 Hz, 1H), 6.40 (s, 1H), 4.52 (s, 3H), 4.20-4.05 (m, 2H), 3.78-3.62 (m, 2H), 3.26-3.16 (m, 1H), 2.20 (s, 6H); MS (ESI) (m/z): [M+H]$^+$ 517.2.

6-(difluoromethoxy)-4-(3-(dimethylamino)azetidin-1-yl)-N$^1$-(4-(1-methyl-1H-thieno[3,2-c]pyrazol-3-yl)pyrimidin-2-yl)benzene-1,3-diamine (compound 50d)

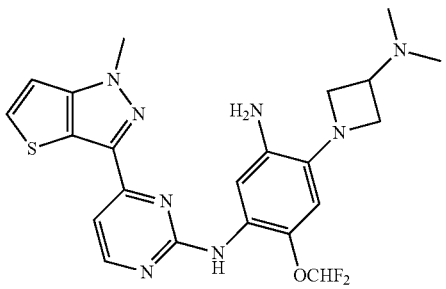

Compound 50d was prepared in the same manner as compound 50a, except that compound 49d was used instead of compound 49a. $^1$H NMR (400 MHz, CDCl$_3$): δ 8.51 (d, J=5.2 Hz, 1H), 7.65 (s, 1H), δ 7.38 (d, J=5.2 Hz, 1H), 7.22 (s, 1H), 7.16 (d, J=5.2 Hz, 1H), 6.96 (d, J=5.2 Hz, 1H), 6.52 (s, 1H), 6.43 (t, J=72 Hz, 1H), 4.46 (s, 3H), 3.96-3.90 (m, 2H), 3.62-3.52 (m, 2H), 3.16-3.08 (m, 1H), 2.20 (s, 6H); MS (ESI) (m/z): [M+H]$^+$ 487.2.

Example 27: N-(4-(difluoromethoxy)-2-(3-(dimethylamino)azetidin-1-yl)-5-((4-(1-methyl-1H-thieno[3,2-c]pyrazol-3-yl)pyrimidin-2-yl)amino)phenyl)acrylamide (compound 51d)

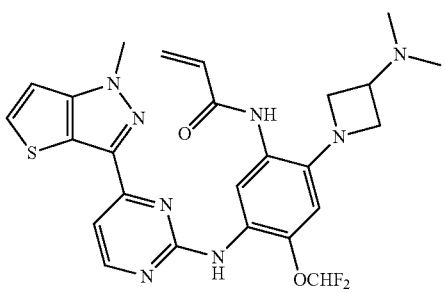 [SMILES: C=CC(=O)Nc1cc(Nc2nccc(-c3nn(C)c4ccsc34)n2)c(OC(F)F)cc1N1CC(N(C)C)C1]

Compound 51 d was prepared in the same manner as compound 51a, except that compound 50d was used instead of compound 50a. $^1$H NMR (400 MHz, CDCl$_3$): δ 8.65 (s, 1H), 8.51 (d, J=5.2 Hz, 2H), 7.42 (s, 1H), 736 (d, J=5.2 Hz, 1H), 7.21 (s, 1H), 7.14 (d, J=5.2 Hz, 1H), 6.98 (d, J=5.2 Hz, 1H), 6.62 (s, 1H), 6.51 (t, J=72 Hz, 1H), 6.48-6.26 (m, 2H), 5.84-5.76 (m, 1H), 4.43 (s, 3H), 3.94-3.84 (m, 2H), 3.66-3.58 (m, 2H), 3.16-3.08 (m, 1H), 2.19 (s, 6H); MS (ESI) (m/s): [M+H]$^+$ 541.2.

N-(2-(difluoromethoxy)-4-(4-(dimethyamino)piperidin-1-yl)-5-nitrophenyl)-4-(1-methyl-1H-thieno[3,2-c]pyrazol-3-yl)pyrimidin-2-amine (compound 49e)

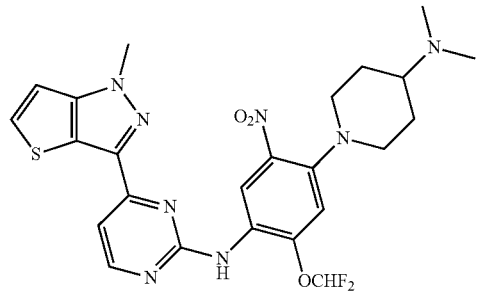 [SMILES: CN(C)C1CCN(c2cc(OC(F)F)c(Nc3nccc(-c4nn(C)c5ccsc45)n3)cc2[N+](=O)[O-])CC1]

Compound 49e was prepared in the sane manner as compound 49a, except that compound 48b was used instead of compound 48a and N N-dimethylpiperidin-4-amine was used instead of N,N,N'-trimethylethylenediamine. MS (ESI) (m/z): [M+H]$^+$ 545.2.

6-(difluoromethoxy)-4-(4-(dimethylamino)piperidin-1-yl)-N$^1$-(4-(1-methyl-1H-thieno[3,2-c]pyrazol-3-yl)pyrimidin-2-yl)benzene-1,3-diamine (compound 50e)

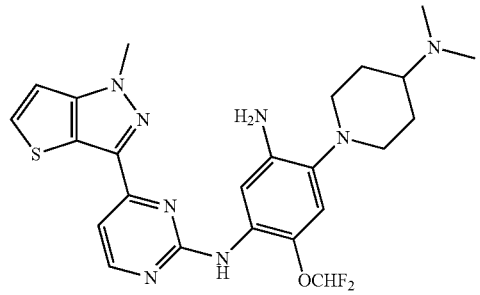

Compound 50e was prepared in the same manner as compound 50a, except that compound 49e was used instead of compound 49a. MS (ESI) (m/z): [M+H]$^+$ 515.2.

Example 28: N-(4-(difluoromethoxy)-2-(4-(dimethylamino)piperidin-1-yl)-5-((4-(1-methyl-1H-thieno[3,2-]pyrol-3-yl)pyrimidin-2-yl)amino)phenyl)acrylamide (compound 51e)

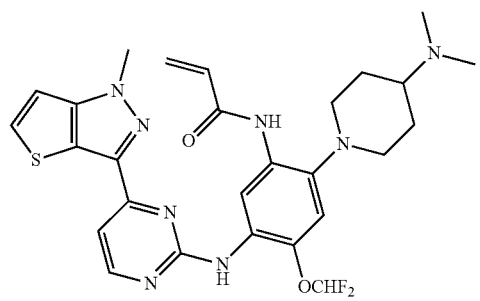 [SMILES: C=CC(=O)Nc1cc(Nc2nccc(-c3nn(C)c4ccsc34)n2)c(OC(F)F)cc1N1CCC(N(C)C)CC1]

Compound 51e was prepared in the same manner as compound 51a, except that compound 50e was used instead of compound 50a. $^1$H NMR (400 MHz, CDCl$_3$): δ 9.33 (s, 1H), 8.62-8.54 (m, 2H), 7.36 (d, J=5.2 Hz, 1H), 7.30 (s, 1H), 7.14 (d, J=5.2 Hz, 1H), 7.05-6.98 (m, 2H), 6.50 (t, J=72.0 Hz, 1H), 6.44-6.22 (m, 2H$_1$), 5.82-5.76 (m, 1H), 4.47 (s, 3H), 3.10-3.03 (m, 2H), 2.76-2.66 (m, 2H), 2.42 (s, 6H), 2.41-2.39 (m, 1H), 2.14-2.05 (m, 2H), 1.78-1.66 (m, 2H); MS (ESI) (m/z): [M+H]$^+$ 569.2.

N-(2-(difluoromethoxy)-4-(5-methyl-2,5-diazaspiro[3.4]oct-2-yl)-5-nitrophenyl)-4-(1-methyl-1H-thieno[3,2-c]pyrazol-3-yl)pyrimidin-2-amine (compound 49f)

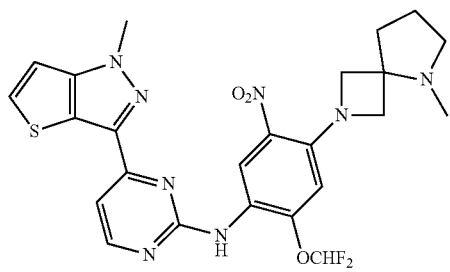 [SMILES: CN1CCCC12CN(c1cc(OC(F)F)c(Nc3nccc(-c4nn(C)c5ccsc45)n3)cc1[N+](=O)[O-])C2]

Compound 49f was prepared in the same manner as compound 49a, except that compound 48b was used instead of compound 48a and 5-methyl-2,5-diazaspiro[3.4]octane was used instead of N,N,N'-trimethylethylenediamine. $^1$H NMR (400 MHz, CDCl$_3$): δ 8.88 (s, 1H), 8.54 (d, J=5.2 Hz, 1H), 7.38 (d, J=5.2 Hz, 1H), 7.24 (s, 1H), 7.17 (d, J=5.2 Hz, 1H), 7.04 (d, J=5.2 Hz, 1H), 6.64 (t, J=72 Hz, 1H), 6.42 (s, 1H), 4.52 (s, 3H), 4.16-4.06 (m, 2H), 3.74-3.64 (m, 2H), 2.80-2.70 (m, 2H), 2.49 (s, 3H), 2.15-2.07 (m, 2H), 1.86-1.76 (m, 2H); MS (ESI) (m/z): [M+H]$^+$ 543.2.

6-(difluoromethoxy)-N-(4-(1-methyl-1H-thieno[3,2-c]pyrazol-3-yl)pyrimidin-2-yl)-4-(5-methyl-2,5-diazaspiro[3.4]oct-2-yl)benzene-1,3-diamine (compound 50f)

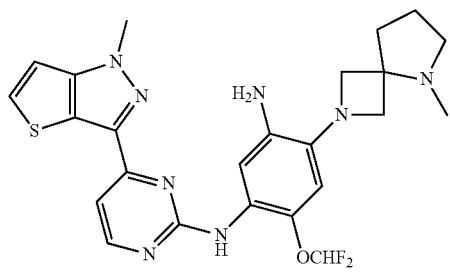 [SMILES: CN1CCCC12CN(c1cc(OC(F)F)c(Nc3nccc(-c4nn(C)c5ccsc45)n3)cc1N)C2]

Compound 50f was prepared in the same manner as compound 50a, except that compound 49f was used instead of compound 49a. $^1$H NMR (400 MHz. CDCl$_3$): δ 8.50 (d, J=5.2 Hz, 1H), 7.64 (s, 1H), 7.38 (d, J=5.2 Hz, 1H), 7.21 (s, 1H), 7.16 (d, J=5.2 Hz, 1H), 6.97 (d, J=5.2 Hz, 11), 6.50 (s, 1H), 6.44 (t, J=72 Hz, 1H), 4.46 (s, 3H), 3.94-3.88 (m, 2H), 3.66-3.60 (m, 2H), 3.55 (bs, 2H), 2.80-2.72 (m, 2H), 2.51 (s, 3H), 2.22-2.14 (m, 2H), 1.86-1.76 (m, 2H); MS (ESI) (m/z): [M+H]$^+$ 513.2.

Example 29: N-(4-(difluoromethoxy)-5-((4-(1-methyl-1H-thieno[3,2-c]pyrazol-3-yl)pyrimidin-2-yl)amino)-2-(5-methyl-2,5-diazaspiro[3.4]oct-2-yl)phenyl)acrylamide (compound 51f)

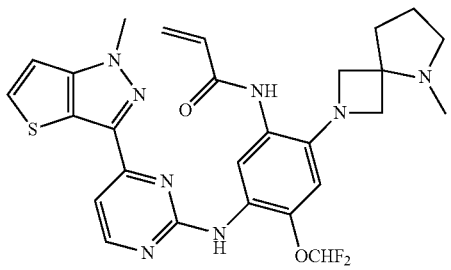 [SMILES: C=CC(=O)Nc1cc(Nc2nccc(-c3nn(C)c4ccsc34)n2)c(OC(F)F)cc1N1CC2(CCCN2C)C1]

Compound 51f was prepared in the same manner as compound 51a, except that compound 50f was used instead of compound 50a. $^1$H NMR (400 MHz, CDCl$_3$): δ 8.57 (s, 1H), 8.50 (d, J=5.2 Hz, 1H), 7.36 (d, J=5.2 Hz, 1H), 7.25 (m, 1H), 7.20 (s, 1H), 7.14 (d, J=5.2 Hz, 1H), 6.98 (d, J=5.2 Hz, 1H), 6.69-6.29 (m, 4H), 5.82-5.76 (m, 1H), 4.43 (s, 3H), 4.02-3.94 (m, 2H), 3.68-3.60 (m, 2H), 2.82-2.72 (m, 2H), 2.52 (s, 3H), 2.22-2.12 (m, 2H), 1.86-1.76 (m, 2H); MS (ESI) (m/z): [M+H]$^+$ 567.2.

The synthesis route of compound 63 is as shown in Scheme 6:

Scheme 6

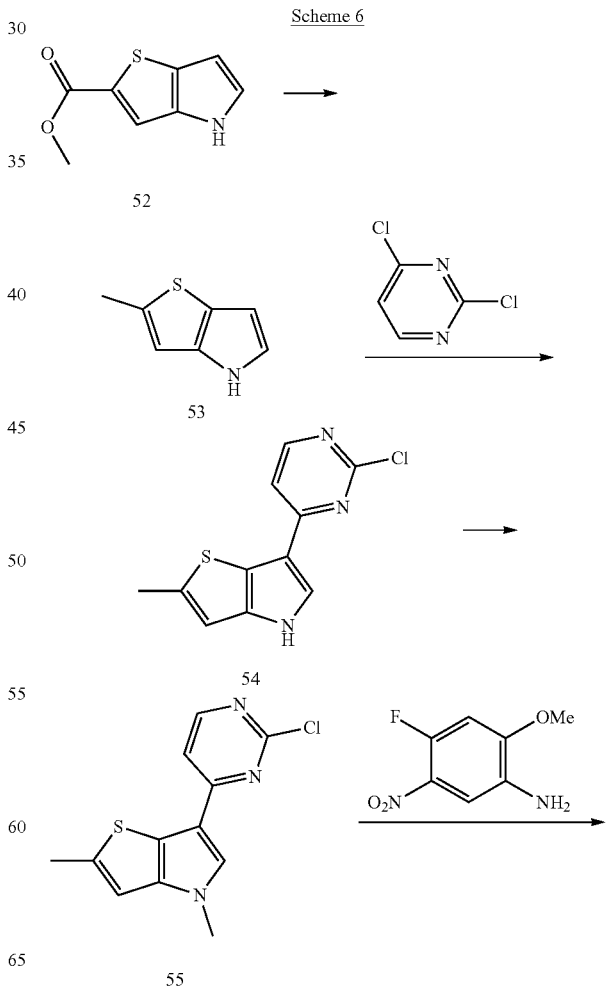

-continued

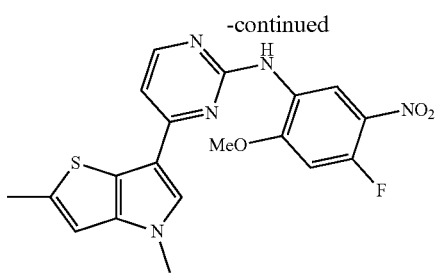

56

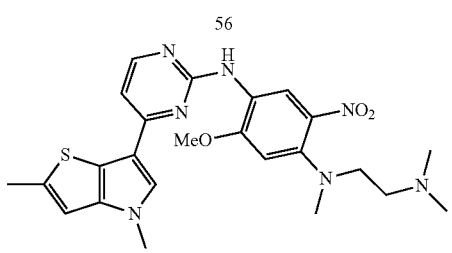

57

58

59

2-methyl-4H-thieno[3,2-b]pyrrole (compound 53)

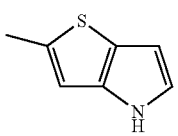

Compound 52 (3 g, 16.6 mmol, synthesized with reference to patent application US20080004327) was dissolved in 500 ml of tetrahydrofuran, and cooled. Lithium aluminum hydride (2.5 g, 66 mmol) was added slowly. The mixture was heated to 70° C. and stirred for 4 hours. After the mixture was cooled to room temperature, 1 M sodium bicarbonate solution was used to quench the reaction at 0° C. Then the mixture was filtered, spin-dried, and purified by column chromatography to obtain a white solid (1.8 g, 79%). MS (ESI) (m/z): [M+H]+138.1. $^1$H NMR (400 MHz, CDCl$_3$): δ 8.11 (br, 1H), 6.91-6.89 (m, 1H), 6.65 (s, 1H), 6.39 (s, 1H), 2.54 (s, 3H).

6-(2-chloropyrimidin-4-yl)-2-methyl-4H-thieno[3,2-b]pyrrole (compound 54)

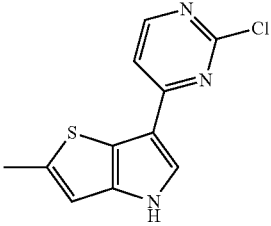 [SMILES: Cc1cc2[nH]cc(-c3ccnc(Cl)n3)c2s1]

2,4-dichloropyrimidine (2.44 g, 16.4 mmol) and iron trichloride (2.66 g, 16.4 mmol) were added into 200 mL of 1,2-dichloroethane, and stirred for 3 hours at room temperature. Compound 53 (1.5 g, 11 mmol) was added into the mixture, and stirred for 4 hours at room temperature. After filtration and concentration, the mixture was purified on a silica gel column to obtain a brown solid (100 mg, 2.4%). MS (ESI) (m/z): [M+H]+ 250.1. $^1$H NMR (400 MHz, CDCl$_3$): δ 9.50 (br, 1H), 8.38 (d, J=5.6 Hz, 1H), 7.33 (d, J=5.2 Hz, 1H), 7.05 (d, J=1.6 Hz, 1H), 6.67 (s, 1H), 2.57 (d, J=1.2 Hz, 3H), 6-(2-chloropyrimidin-4-yl)-2,4-dimethyl-4H-thieno[3,2-b]pyrrole (compound 55)

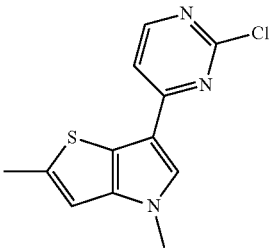 [SMILES: Cc1cc2c(s1)c(-c1ccnc(Cl)n1)cn2C]

Compound 54 (100 mg, 0.4 mmol), iodomethane (1.42 g, 4 mmol), and potassium carbonate (276 mg, 2 mmol) were added into 5 mL of DMF, stirred for one week at room temperature, and ethyl acetate was added to dilute the mixture. The mixture was washed sequentially with water and saturated brine, dried, and purified on a silica gel column to obtain a yellow solid (50 mg, 47%). MS (ESI) (m/z): [M+H]+ 264.1. $^1$H NMR (400 MHz, CDCl$_3$): δ 8.36 (d, J=5.6 Hz, 1H), 7.36 (d, J=5.6 Hz, 1H), 7.01 (s, 1H), 6.66 (s, 1H), 4.14 (s, 3H), 2.57 (d, J=0.8 Hz, 3H).

4-(2,4-dimethyl-4H-thieno[3,2-b]pyrrol-6-yl)-N-(4-fluor-2-methoxy-5-nitrophenyl)pyrimidin-2-amine (compound 56)

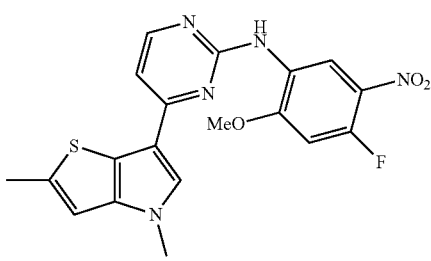 [SMILES: COc1cc(F)c([N+](=O)[O-])cc1Nc1nccc(-c2cn(C)c3cc(C)sc23)n1]

Compound 55 (50 mg, 0.19 mmol), 2-methoxy-4-fluoro-5-nitroaniline (71 mg, 0.38 mmol) and p-toluene sulfonic acid monohydrate (108 mg, 0.57 mmol) were added into 5 mL of sec-pentanol, and stirred for 5 hours at 100° C. The mixture was cooled and filtered. The solid was washed with ethyl acetate to obtain a yellow solid (65 mg, 83%). MS (ESI) (m/z): [M+H]+ 414.1. $^1$H NMR (400 MHz, CDCl$_3$): δ 9.35 (d, J=8.4 Hz, 1H), 8.33 (d, J=5.2 Hz, 1H), 7.59 (br, 1H), 7.05 (d, J=5.2 Hz, 1H), 6.96 (s, 1H), 6.75 (d, J=12 Hz, 1H), 6.68 (s, 1H), 4.15 (s, 3H), 4.02 (s, 3H), 2.57 (s, 3H).

N-(4-(2,4-dimethyl-4H-thieno[3,2-b]pyrrol-6-yl)pyrimidin-2-yl)-N$^4$-(2-(dimethylamino)ethyl)-2-methoxy-N$^4$-methyl-5-nitrobenzene-1,4-diamine (compound 57)

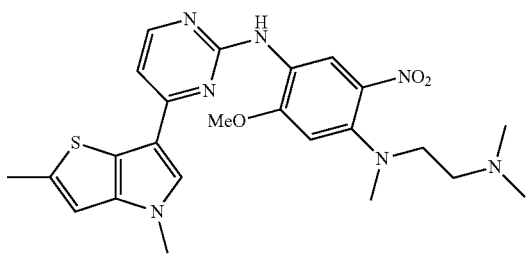

Compound 56 (65 mg, 0.16 mmol) and N,N,N'-trimethylethylenediamine (32 mg, 0.31 mmol) were dissolved in 10 ml of acetonitrile, and potassium carbonate (43 mg, 0.31 mmol) was added. The mixture was stirred for 4 hours at 80° C. Then, the mixture was filtered, concentrated, and purified on a silica gel column to obtain a red solid (55 mg, 70%). MS (ESI) (m/z): [M+H]+ 496.3. $^1$H NMR (400 MHz, CDCl$_3$): δ 9.05 (s, 1H), 8.31 (d, J=5.2 Hz, 1H), 7.48 (s, 1H), 7.00 (d, J=5.6 Hz, 1H), 6.94 (s, 1H), 6.76 (s, 1H), 6.68 (s, 1H), 4.15 (s, 3H), 4.00 (s, 3H), 3.41-3.37 (m, 2H), 2.88 (s, 3H), 2.80-2.77 (m, 2H), 2.57 (s, 3H), 2.46 (s, 6H).

N$^4$-(4-(2,4-dimethyl-4H-thieno[3,2-b]pyrol-yl)pyrimidin-2-yl)-N$^1$-(2-(dimethylamino)ethyl)-5-methoxy-N$^1$-toluene-1,2,4-triamine (compound 58)

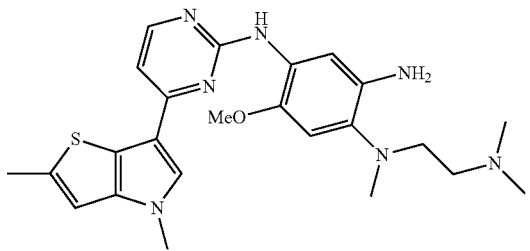

A mixture of compound 57 (55 mg, 0.11 mmol) and palladium on carbon in methanol was stirred for 1 h under a hydrogen atmosphere at room temperature. After filtration through celite, the filtrate was concentrated to obtain a yellow solid (50 mg, 98%). MS (ESI) (m/z): [M+H]+ 466.2. $^1$H NMR (400 MHz, CDCl$_3$): δ 8.28 (d, J=5.2 Hz, 1H), 7.94 (s, 1H), 7.48 (s, 1H), 6.91-6.90 (m, 2H), 6.70 (s, 1H), 6.66 (s, 1H), 4.13 (s, 3H), 3.83 (s, 3H), 2.97-2.94 (m, 2H), 2.67 (s, 3H), 2.57 (d, J=0.8 Hz, 3H), 2.41-2.38 (m, 2H), 2.26 (s, 6H).

Example 30: N—(5-((4-(2,4-dimethyl-4H-thieno[3,2-b]pyrol-6-yl)pyrimidin-2-yl)amino)-2-((2-(dimethyamino)ethyl)methyl)amino)-4-methoxyphenyl) acrylamide (compound 59)

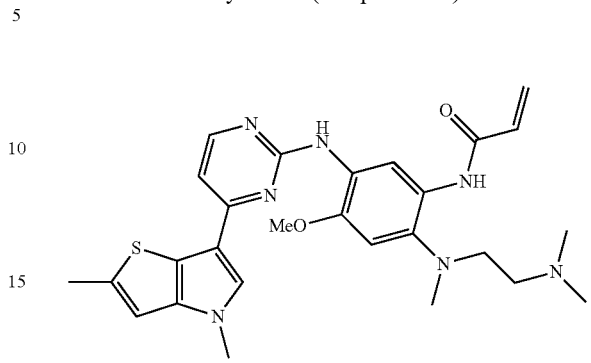

Compound 58 (50 mg, 0.1 mmol), triethylamine (33 mg, 0.32 mmol), and acrylic acid (23 mg, 0.32 mmol) were dissolved in 2 mL of dichloromethane, and catalytic amount of tert-butanol was added, and the mixture was cooled to −10° C. Subsequently, EDCI (41 mg, 0.22 mmol) was added and stirred for 2 hours at room temperature. The reaction solution was diluted with dichloromethane, washed with an aqueous solution of sodium bicarbonate and saturated brine, dried, and purified by a silica gel column and preparatory plate to obtain a yellow solid (7.7 mg, 13.8%). MS (ESI) (m/z): [M+H]+ 520.2. $^1$H NMR (400 MHz, CDCl$_3$): δ 9.49 (s, 1H), 927 (s, 1H), 8.32 (d, J=5.2 Hz, 1H), 7.51 (s, 1H), 7.06-693 (m, 3H), 6.68 (s, 1H), 6.63 (s, 1H), 6.42 (d, J=16.8 Hz, 1H), 5.71 (d, J=10.4 Hz, 1H), 4.06 (s, 3H), 3.87 (s, 3H), 3.18 (s, 2H), 2.93 (s, 2H), 2.69 (s, 3H), 2.66 (a, 6H), 2.56 (s, 3H).

The synthesis route of compound 72 is as shown in Scheme 7:

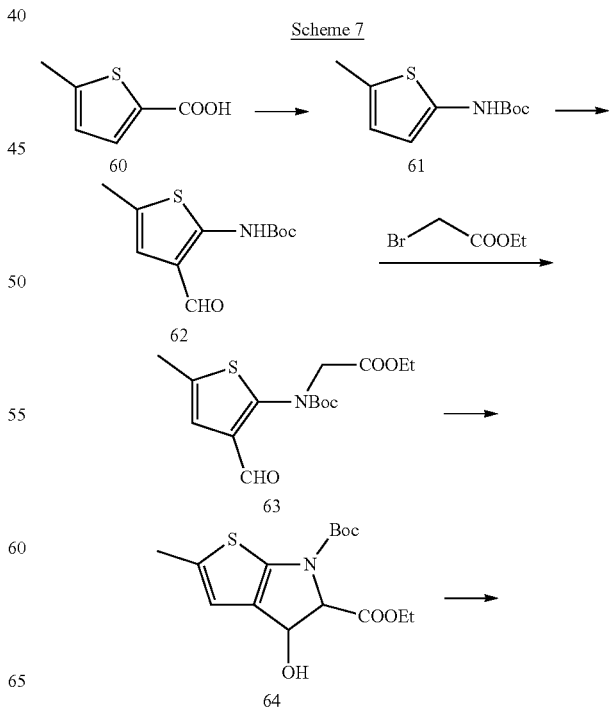

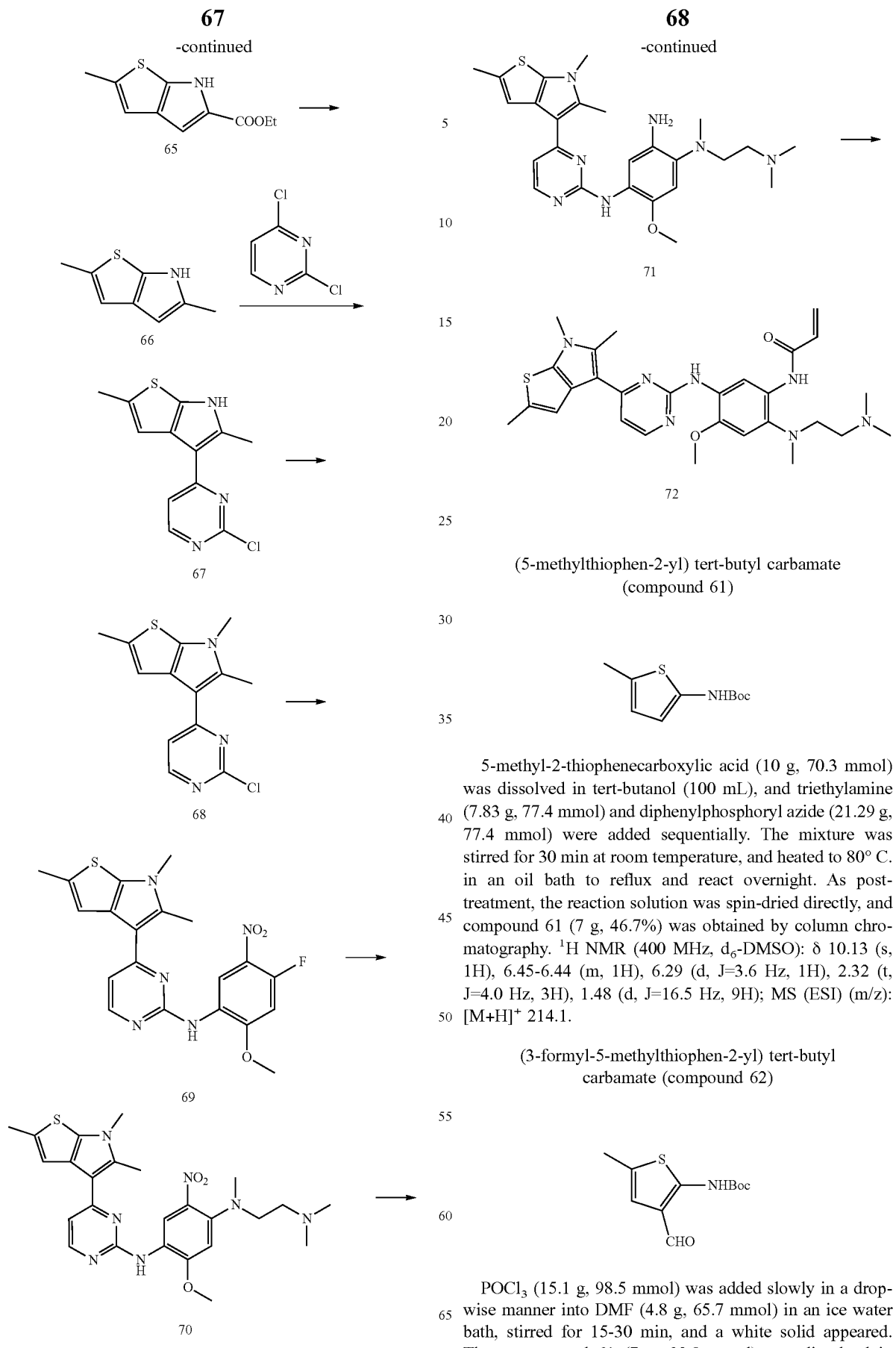

(5-methylthiophen-2-yl) tert-butyl carbamate (compound 61)

5-methyl-2-thiophenecarboxylic acid (10 g, 70.3 mmol) was dissolved in tert-butanol (100 mL), and triethylamine (7.83 g, 77.4 mmol) and diphenylphosphoryl azide (21.29 g, 77.4 mmol) were added sequentially. The mixture was stirred for 30 min at room temperature, and heated to 80° C. in an oil bath to reflux and react overnight. As post-treatment, the reaction solution was spin-dried directly, and compound 61 (7 g, 46.7%) was obtained by column chromatography. $^1$H NMR (400 MHz, d$_6$-DMSO): δ 10.13 (s, 1H), 6.45-6.44 (m, 1H), 6.29 (d, J=3.6 Hz, 1H), 2.32 (t, J=4.0 Hz, 3H), 1.48 (d, J=16.5 Hz, 9H); MS (ESI) (m/z): [M+H]$^+$ 214.1.

(3-formyl-5-methylthiophen-2-yl) tert-butyl carbamate (compound 62)

POCl$_3$ (15.1 g, 98.5 mmol) was added slowly in a dropwise manner into DMF (4.8 g, 65.7 mmol) in an ice water bath, stirred for 15-30 min, and a white solid appeared. Then, compound 61 (7 g, 32.8 mmol) was dissolved in tetrahydrofuran (100 mL), and the mixture was added into a reaction flask, heated to room temperature, and stirred to react overnight. The react solution was added slowly into warm water (100 mL) to quench the reaction. The mixture was extracted with ethyl acetate, and subjected to column chromatography to obtain compound 62 (3 g, 38.0%). $^1$H NMR (400 MHz, CDCl$_3$): δ 10.47 (s, 1H), 9.69 (s, 1H), 6.76 (s, 1H), 2.39 (s, 3H), 1.56 (s, 9H); MS (ESI) (m/z): [M+H]$^+$ 242.1.

2-((tert-butoxycarbonyl)(3-formyl-5-methylthiophen-2-yl)amino)ethyl acetate (compound 63)

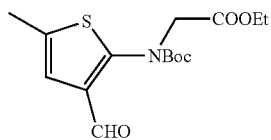 [SMILES: CCOC(=O)CN(C(=O)OC(C)(C)C)c1sc(C)cc1C=O]

Compound 62 (2.9 g, 12.0 mmol) was dissolved in DMF (30 mL), and potassium carbonate (2.5 g, 18.1 mmol) and ethyl bromoacetate (2.4 g, 14.4 mmol) were added. The mixture was stirred overnight at room temperature. As post-treatment, water (50 mL) was added, and the mixture was extracted with ethyl acetate, dried over sodium sulfate, and spin-dried to obtain crude product 63 (4 g, 100%), which was used directly as feed for the next step. MS (ESI) (m/z): [M+H]$^+$ 328.1.

6-tert-butyl-5-ethyl-4-hydroxyl-2-methyl-4H-thieno[2,3-b]pyrol-5,6(5H)-dicarboxylic acid ester (compound 64)

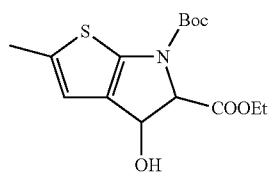 [SMILES: CCOC(=O)C1C(O)c2cc(C)sc2N1C(=O)OC(C)(C)C]

Compound 63 (4 g, 12.2 mmol) was dissolved in DMF (40 mL), and potassium carbonate (2.53 g, 18.3 mmol) was added. The mixture was heated to 60° C. in an oil bath to react overnight. As post-treatment, water (50 mL) was added, and the mixture was extracted with ethyl acetate. Compound 64 (3.8 g, 86.2%) was obtained by column chromatography.

Ethyl 2-methyl-6H-thieno[2,3-b]pyrrol-5-carboxylate (compound 65)

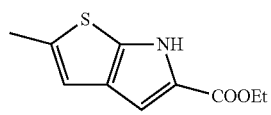

Compound 64 (3.8 g, 11.6 mmol) was dissolved in ethanol (15 mL), and 3 mL of concentrated hydrochloric acid was added. The mixture was stirred at room temperature. After the completion of reaction, the react solution was spin-dried directly. Water was added, and the resulted mixture was neutralized with potassium carbonate, extracted with ethyl acetate (50 mL), dried over sodium sulfate, and spin-dried to obtain compound 65 (1.8 g, 74%). MS (ESI) (m/z): [M+H]$^+$ 210.1.

2,5-dimethyl-6H-thieno[2,3-b]pyrrole (compound 66)

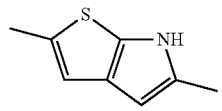

Compound 65 (500 mg, 2.4 mmol) was dissolved in anhydrous THF (5 mL), and cooled in ice-salt bath. Lithium aluminum hydride (226.7 mg, 6.0 mmol) was added slowly. Heat was generated and a large number of bubbles were generated. After the completion of addition, the system was heated to 70° C. in an oil bath to reflux. After the reaction was complete, the system was cooled in an ice water bath, and water and NaOH (aq) were added slowly. The mixture was extracted with ethyl acetate, filtered through celite, and spin-dried to obtain compound 66 (250 mg, 69.1%). $^1$H NMR (400 MHz, CDCl$_3$): δ 7.88 (s, 1H), 6.62 (t, J=6.0 Hz, 1H), 6.08-5.94 (m, 1H), 2.52 (d, J=1.2 Hz, 3H), 2.39-2.37 (m, 3H); MS (ESI) (m/z): [M+H]$^+$ 152.0.

4-(2-chloropyrimidin-4-yl)-2,5-dimethyl-6H-thieno[2,3-b]pyrrole (compound 67)

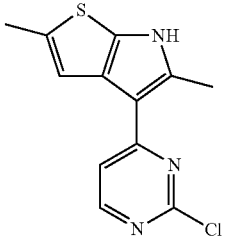

Compound 66 (200 mg, 1.3 mmol) was dissolved in 1,2-dichloromethane (5 mL), then 2,4-dichloropyrimidine (295.5 mg, 2.0 mmol) and aluminum trichloride (264.5 mg, 2.0 mmol) were added sequentially. The system was heated to 80° C. in an oil bath to react. After the reaction was complete, water (10 mL) was added to quench the reaction, the solid was filtered with suction, and dichloromethane was added to extract the mixture. The organic phase was dried by spin-drying, and subjected to column chromatography purification to obtain compound 67 (100 mg, 26.7%6). $^1$H NMR (400 MHz, CDCl$_3$): δ 9.73 (s, 1H), 8.29 (t, J=7.7 Hz, 1H), 7.18 (d, J=5.5 Hz, 1H), 6.88 (d, J=1.1 Hz, 1H), 2.59 (d, J=1.0 Hz, 3H), 2.49 (s, 3H); MS (ESI) (m/z): [M+H]$^+$ 264.0.

4-(2-chloropyrimidin-4-yl)-2,5,6-trimethyl-6H-thieno[2,3-b]pyrrole (compound 68)

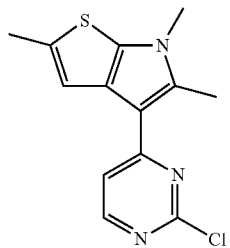

Compound 67 (73 mg, 0.38 mmol) was dissolved in DMF (5 mL), then iodomethane (47.14 mg, 0.45 mmol) and potassium carbonate (57.30 mg, 0.57 mmol) were added sequentially and stirred at room temperature. As post-treatment, water (10 mL) was added, and the mixture was extracted with ethyl acetate (10 mL), washed twice with saturated brine, dried and concentrated to obtain compound 68 (80 mg). MS (ESI) (m/z): [M+H]$^+$ 278.0.

N-(4-fluoro-2-methoxy-5-nitrophenyl)-4-(2,5,6-trimethyl-6H-thieno[2,3-b]pyrrol-4-yl)pyrimidin-2-amine (compound 69)

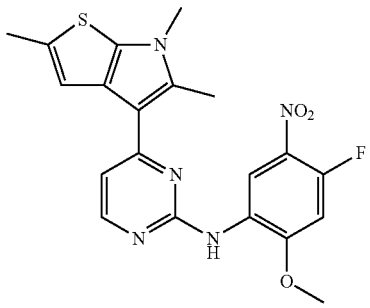 [SMILES: COc1cc(F)c([N+](=O)[O-])cc1Nc1nccc(-c2c(C)n(C)c3sc(C)cc23)n1]

Compound 68 (80 mg, 0.288 mmol) was dissolved in sec-pentanol (5 mL), then 4-fluoro-2-ethoxy-5-nitroaniline (53.6 mg, 0.288 mmol) and p-toluene sulfonic acid (82.18 mg, 0.430 mmol) were added sequentially, and the mixture was heated to 105° C. in an oil bath to react. As post-treatment, the reaction solution was spin-dried directly, and purified by preparative chromatography to obtain compound 69 (60 mg, 48.7%). $^1$H NMR (400 MHz, CDCl$_3$): δ 9.48 (d, J=8.4 Hz, 1H), 8.40 (d, J=5.3 Hz, 1H), 7.65 (s, 1H), 7.10 (d, J=5.3 Hz, 1H), 6.96 (s, 1H), 6.80 (d, J=4.2 Hz, 1H), 4.05 (s, 3H), 3.68 (s, 3H), 2.79 (s, 3H), 2.59 (s, 3H); MS (ESI) (m/z): [M+H]$^+$ 428.1.

N$^1$-(2-(dimethylamino)ethyl)-5-methoxy-N$^1$-methyl-2-nitro-N$^4$-(4-(2,5,6-trimethyl-6H-thieno[2,3-b]pyrrol-4-yl)pyrimidin-2-yl)benzene-1,4-diamine (compound 70)

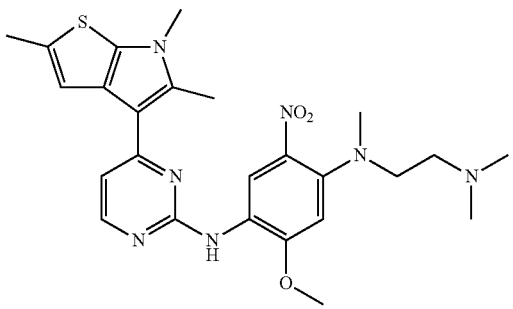

Compound 69 (60 mg, 0.14 mmol) was dissolved in DMF (5 mL), then N,N,N'-trimethylethylenediamine (17.2 mg, 0.16 mmol) and N,N-diisopropylethylamine (23.6 mg, 0.18 mmol) were added sequentially, and the mixture was heated to 85° C. in an oil bath and stirred. After the completion of reaction, water (10 mL) was added to quench the reaction. The mixture was extracted with ethyl acetate (10 mL), washed twice with saturated brine, dried by spin-drying, and purified by preparative chromatography to obtain compound 70 (50 mg, 69.9%). $^1$H NMR (400 MHz, CDCl$_3$): δ 9.19 (s, 1H), 8.37 (d, J=5.3 Hz, 1H), 7.60 (s, 1H), 7.03 (d, J=5.3 Hz, 1H), 6.95 (s, 11H), 6.87 (s, 1H), 4.05 (s, 3H), 3.65 (s, 3H), 3.52 (t, J=6.6 Hz, 2H), 3.49 (s, 3H), 3.02 (t, J=6.8 Hz, 2H), 2.88 (s, 3H), 2.76 (s, 3H), 2.66 (s, 6H); MS (ESI) (m/z): [M+H]$^+$ 510.2.

N$^1$-(2-(dimethylamino)ethyl)-5-methoxy-N$^1$-methyl-N$^4$-((2,5,6-triethyl-6H-thieno[2,3-b]pyrrol-4-yl)pyrimidin-2-yl)benzene-1,2,4-triamine (compound 71)

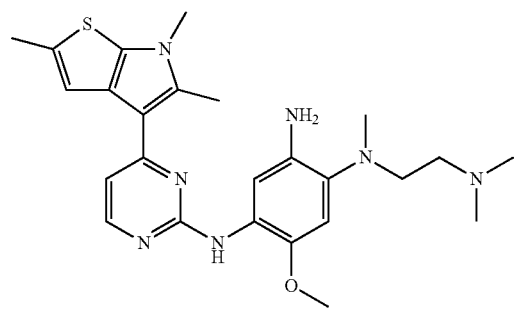

Compound 70 (50 mL, 0.098 mmol) was dissolved in ethanol (6 mL) and water (2 mL), then iron powder (32.87 mg, 0.587 mmol) and ammonium chloride (3.67 mg, 0.067 mmol) were added sequentially, and the mixture was heated to 80° C. in an oil bath to react. The reaction was complete in 2 hours. The reaction solution was filtered with suction, and purified by preparative chromatography to obtain compound 71 (21 mg, 44.68 V %). MS (ESI) (m/z): [M+H]$^+$ 480.2.

Example 31: N-(2-((2-(dimethylamino)ethyl)(methyl)amino)-4-methoxy-5-((4-(2,5,6-trimethyl-thieno[2,3-b]pyrrol-4-yl)pyrimidin-2-yl)amino)phenyl)acrylamide (compound 72)

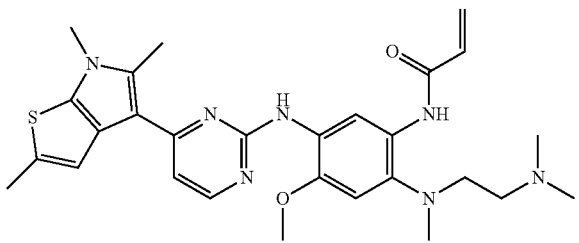

Compound 71 (21 mg, 0.044 mmol) was dissolved in DCM (5 mL) and tert-butanol (0.5 mL), cooled in an ice water bath, and EDCI (16.79 mg, 0.088 mmol), triethylamine (8.84 mg, 0.088 mmol), and acrylic acid (6.31 mg, 0.088 mmol) were added sequentially. The reaction was complete after stirring for 3 h. Compound 72 (5 mg, 21.39%) was obtained by preparative chromatography purification. $^1$H NMR (400 MHz, CDCl$_3$): δ 9.64 (s, 1H), 9.33 (s, 1H), 8.33 (d, J=5.4 Hz, 1H), 7.48 (s, 1H), 6.96 (d, J=5.5 Hz, 1H), 6.87 (s, 1H), 6.71 (s, 1H), 6.41 (d, J=16.8 Hz, 1H), 5.71 (d, J=11.7 Hz, 1H), 4.08 (s, 3H), 3.90 (s, 3H), 3.12 (s, 2H), 2.77 (s, 2H), 2.72 (s, 3H), 2.60 (s, 6H), 2.54 (s, 3H), 2.41 (s, 3H); MS (ESI) (m/z): [M+H]$^+$ 534.3.

The synthesis route of compounds 80a-80f is as shown in Scheme 8:

Scheme 8

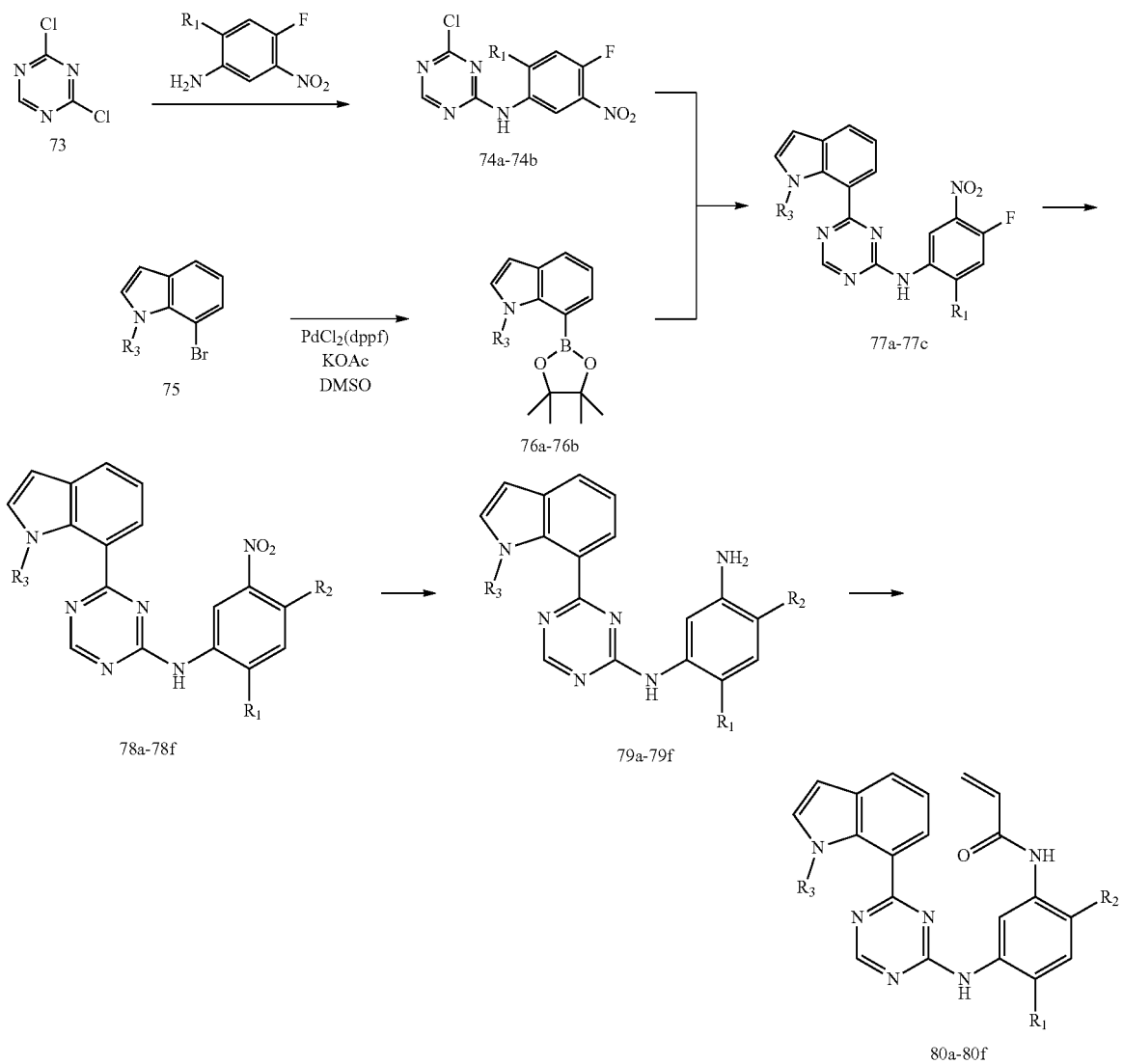

4-chloro-N-(4-fluoro-2-methoxy-5-nitrophenyl)-1,3,5-triazin-2-amine (compound 74a)

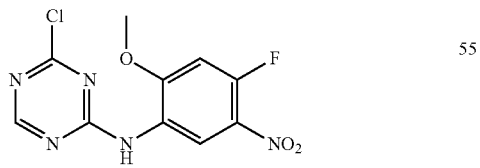

Compound 73 (1.77 g, 11.80 mmol) was dissolved in N,N-dimethylformamide (20 mL), then 2-methoxy-4-fluoro-5-nitroaniline (2 g, 10.74 mmol) and N,N-diisopropylethylamine (1.67 g, 12.92 mmol) were added sequentially, and stirred at room temperature. The reaction was complete after 3 hours, and water (50 mL) was added. A large amount of solid was precipitated, and the mixture was filtered with suction to obtain the crude product, which was washed twice with ethyl acetate to obtain pure product 74a (1.8 g, 56.25%). MS (ESI) (m/z): [M+H]$^+$ 300.0.

4-chloro-N-(2-(difluoromethoxy)-4-fluoro-5-nitrophenyl)-1,3,5-triazin-2-amine (compound 74b)

2-(difluoromethoxy)-4-fluoro-5-nitroaniline (30 g, 0.135 mol) was dissolved in DMF (100 mL) in a 250 mL single neck flask, and sodium bicarbonate (17 g, 0.20 mol) was added. Then compound 73 (30 g, 0.20 mol) was slowly added into the mixture in an ice bath, and the system was heated to room temperature to react for 2 h. Water was added to quench the reaction, The mixture was extracted with ethyl acetate for 3 times, dried over sodium sulfate, concentrated, and subjected to column chromatography to obtain compound 74b (50 g, 0.149 mol). $^1$H NMR (400 MHz, d$_6$-DMSO): δ 10.64 (s, 1H), 8.64 (s, 1H), 8.49 (d, J=7.7 Hz, 1H), 7.63 (d, J=12.0 Hz, 1H), 7.61-7.22 (m, 1H); MS (ESI) (m/z): [M+H]$^+$ 336.0.

7-(4,4,5,5-tetramethyl-1,3,2-dioxaborolan-2-yl)-1H-indole (compound 76a)

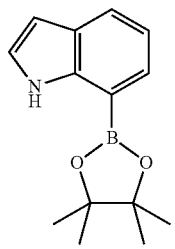 [SMILES: CC1(C)OB(c2cccc3cc[nH]c23)OC1(C)C]

7-bromoindole (20 g, 0.102 mol) was dissolved in DMSO (100 mL) in an 1 L single neck flask, and bis(pinacolato)diboron (39 g, 0.153 mol), [1,1'-bis(diphenylphosphino)ferrocene]dichloropalladium (Pd(dppf)Cl$_2$, 4 g, 0.005 mol), and potassium acetate (15 g, 0.153 mol) were added. The system was heated to 85° C. to react for 2 h. Water was added to quench the reaction. The mixture was extracted with ethyl acetate for 3 times, dried over sodium sulfate, concentrated, and subjected to column chromatography to obtain the product (25 g, 0.103 mol). $^1$H NMR (400 MHz, CDCl$_3$): δ 9.29 (s, 1H), 7.82 (d, J=7.9 Hz, 1H), 7.70 (d, J=7.0 Hz, 1H), 7.32-7.29 (m, 1H), 7.21-7.14 (m, 1H), 6.62-6.57 (m, 1H), 1.44 (s, 12H). MS (ESI) (m/z): [M+H]$^+$ 244.1.

1-methyl-7-(4,4,5,5-tetramethyl-1,3,2-dioxaborolan-2-yl)-H-indole (compound 76b)

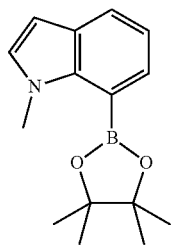 [SMILES: Cn1ccc2cccc(B3OC(C)(C)C(C)(C)O3)c21]

7-bromo-1-methyl-1H-indole (2 g, 0.01 mol) was dissolved in DMSO (50 mL) in a 100 mL single neck flask, and bis(pinacolato)diboron (5 g, 0.02 mol), Pd(dppf)Cl$_2$ (0.8 g, 0.00 mol), and potassium acetate (2.4 g, 0.024 mol) were added. The system was heated to 85° C. to react for 2 h. Water was added to quench the reaction. The mixture was extracted with ethyl acetate for 3 times, dried over sodium sulfate, concentrated, and subjected to column chromatography to obtain compound 76b (2.5 g, 0.012 mol). $^1$H NMR (400 MHz, CDCl$_3$): δ 7.79-7.72 (m, 1H), 7.70 (d, J=6.9 Hz, 1H), 7.13 (t, J=7.5 Hz, 1H), 7.04 (d, J=3.1 Hz, 1H), 6.52 (d, J=3.1 Hz, 1H), 4.00 (s, 3H), 1.43 (s, 12H); MS (ESI) (m/z): [M+H]$^+$ 258.1.

N-(4-fluoro-2-methoxy-5-nitrophenyl)-4-(H-indol-7-yl)-1,3,5-triazin-2-amine (compound 77a)

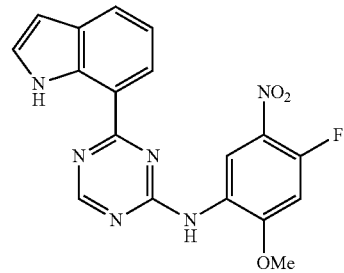 [SMILES: COc1cc(F)c([N+](=O)[O-])cc1Nc1ncnc(-c2cccc3cc[nH]c23)n1]

Compound 76a (609 mg, 2.5 mmol) was dissolved in 1,4-dioxane (50 mL) in a 100 mL single neck flask, then compound 74a (500 mg, 1.67 mmol), tetrakis(triphenylphosphine)palladium (193 mg, 0.167 mmol), sodium carbonate (442 mg, 4.17 mmol), and water (15 mL) were added, and the temperature was increased to 80° C. to react for 2 h. Water was added to quench the reaction. The mixture was extracted with ethyl acetate for 3 times, dried over sodium sulfate, concentrated, and subjected to column chromatography to obtain compound 77a (1 g, 2.6 mmol). MS (ESI) (m/z): [M+H]$^+$381.1.

N-(2-(difluoromethoxy)-4-fluoro-5-nitrophenyl)-4-(H-indol-7-yl)-1,3,5-triazin-2-amine (compound 77b)

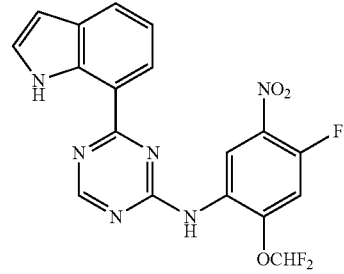 [SMILES: O=[N+]([O-])c1cc(Nc2ncnc(-c3cccc4cc[nH]c34)n2)c(OC(F)F)cc1F]

Compound 77b was prepared in the same manner as compound 77a, except that compound 74b was used instead of compound 74a. MS (ESI) (m/z): [M+H]$^+$ 417.1.

N-(4-fluoro-2-methoxy-S-nitrophenyl)-4-(1-methyl-1H-indol-7-yl)-1,3,5-triazin-2-amine (compound 77c)

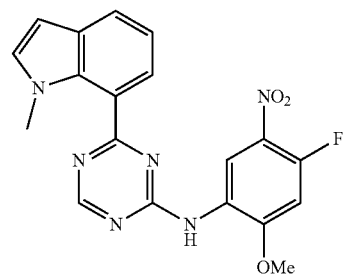 [SMILES: COc1cc(F)c([N+](=O)[O-])cc1Nc1ncnc(-c2cccc3ccn(C)c23)n1]

Compound 77c was prepared in the same manner as compound 77a, except that compound 76b was used instead of compound 76a. MS (ESI) (m/z): [M+H]$^+$ 395.1.

N¹-(4-(1H-indol-7-yl)-1,3,5-triazin-2-yl)-N-(2-(dimethylamino)ethyl)-2-methoxy-N⁴-methyl-5-nitrobenzene-1,4-diamine (compound 78a)

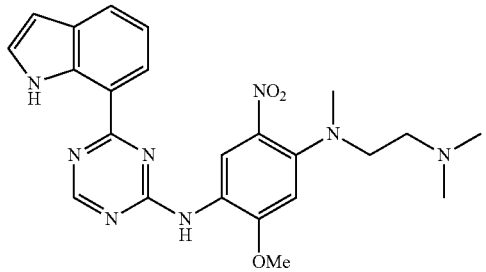 [SMILES: COc1cc(N(C)CCN(C)C)c([N+](=O)[O-])cc1Nc1ncnc(-c2cccc3cc[nH]c23)n1]

Compound 77a (1 g, 2.63 mmol) was dissolved in N,N-dimethylformamide (30 mL) in a 100 mL single neck flask, and N,N,N'-trimethylethylenediamine (458 mg, 3.95 mmol) and N,N-diisopropylethylamine (1.01 g, 7.89 mmol) were added. The temperature was increased to 60° C. to react for 2 hours. Water was added to quench the reaction. The mixture was extracted with ethyl acetate for 3 times, dried over sodium sulfate, concentrated, and subjected to column chromatography to obtain product 78a (400 mg, 0.866 mmol). ¹H NMR (400 MHz, CDCl₃): δ 10.91 (s, 1H), 9.31 (s, 1H), 8.84 (s, 1H), 8.57 (s, 1H), 7.91 (d, J=7.7 Hz, 1H), 7.69 (s, 1H), 7.40-7.30 (m, 2H), 6.70 (s, 1H), 6.66-6.62 (m, 1H), 3.99 (s, 3H), 3.35 (t, J=6.9 Hz, 2H), 2.94 (s, 3H₁), 2.62 (t, J=7.0 Hz, 2H), 2.31 (s, 6H); MS (ESI) (m/z): [M+H]⁺ 463.2.

N¹-(4-((1H-indol-7-yl)-1,3,5-triazin-2-yl)-2-(difluoromethoxy)-N⁴-(2-(dimethylamino)ethyl)-N⁴-methyl-5-nitrobenzene-1,4-diamine (compound 78b)

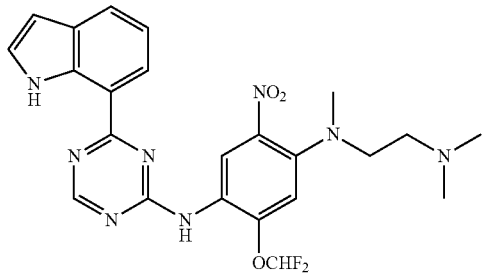 [SMILES: CN(C)CCN(C)c1cc(OC(F)F)c(Nc2ncnc(-c3cccc4cc[nH]c34)n2)cc1[N+](=O)[O-]]

Compound 78b was prepared in the same manner as compound 78a, except that compound 77b was used instead of compound 77a. MS (ESI) (m/z): [M+H]⁺ 499.2.

4-(H-indol-7-yl)-N-(2-methoxy-4-(4-methylpiperazin-1-yl)-5-nitrophenyl)-1,3,5-triazin-2-amine (compound 78c)

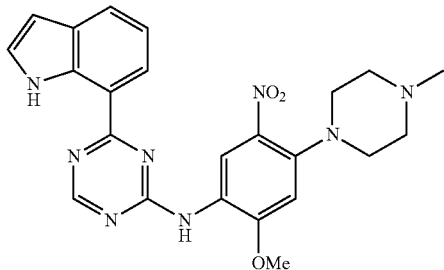 [SMILES: COc1cc(N2CCN(C)CC2)c([N+](=O)[O-])cc1Nc1ncnc(-c2cccc3cc[nH]c23)n1]

Compound 78c was prepared in the same manner as compound 78a, except that 4-methylpiperazine was used instead of N,N,N'-trimethylethylenediamine. ¹H NMR (400 MHz, d₆-DMSO): δ 11.90 (s, 1H), 9.90 (s, 1H), 8.85 (s, 1H), 8.74 (s, 1H), 8.35-8.33 (m, 1H), 7.88 (d, J=7.6 Hz, 1H), 7.58 (s, II), 7.20 (t, J=7.7 Hz, 1H), 6.90 (s, 1H), 6.64 (s, 1H), 4.07 (s, 3H), 3.27-3.23 (m, 4H), 2.98-2.82 (m, 4H), 2.74 (s, 3H); MS (ESI) (m/z): [M+H]⁺ 461.2.

N-(4-(3-(dimethylamino)azetidin-1-yl)-2-methoxy-5-nitrophenyl)-4-(1H-indol-7-yl)-1,3,5-triazin-2-amine (compound 78d)

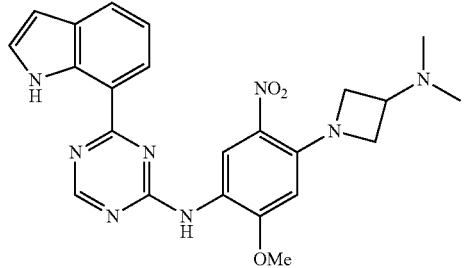 [SMILES: COc1cc(N2CC(N(C)C)C2)c([N+](=O)[O-])cc1Nc1ncnc(-c2cccc3cc[nH]c23)n1]

Compound 78d was prepared in the same manner as compound 78a, except that N,N-dimethylazetidin-3-amine was used instead of N,N,N'-trimethylethylenediamine. ¹H NMR (400 MHz, d₆-DMSO): δ 11.86 (s, 1H), 9.74 (s, 1H), 8.81 (s, 1H), 8.53 (s, 1H), 8.35 (s, 1H), 7.88 (d, J=6.9 Hz, 1H), 7.57 (s, 1H), 7.20 (t, J=7.3 Hz, 1H), 6.64 (s, 1H), 6.32 (s, 1H), 4.08-3.89 (m, 5H), 3.82-3.78 (m, 2H), 3.20-3.16 (m, 1H), 2.17 (s, 6H); MS (ESI) (m/z): [M+H]⁺ 461.2.

4-(1H-indol-7-yl)-N-(2-methoxy-4-(5-methyl-2,5-diazaspiro[3.4]oct-2-yl)-5-nitrophenyl)-1,3,5-triazin-2-amine (compound 78e)

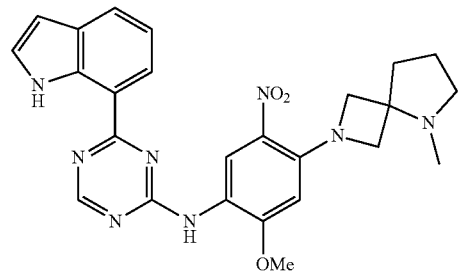 [SMILES: COc1cc(N2CC3(CCCN3C)C2)c([N+](=O)[O-])cc1Nc1ncnc(-c2cccc3cc[nH]c23)n1]

Compound 78e was prepared in the same manner as compound 78a, except that N,N-dimethylazetidin-3-amine was used instead of N,N,N'-trimethylethylenediamine. MS (ESI) (m/z): [M+H]⁺ 487.2.

N¹-(2-(dimethylamino)ethyl)-5-methoxy-N¹-methyl-N⁴-(4-(1-methyl-1H-indol-7-yl)-1,3,5-triazin-2-yl)-2-nitrobenzene-1,4-diamine (compound 78f)

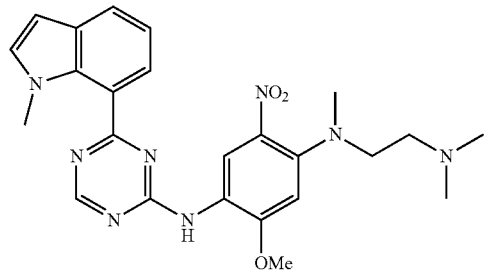 [SMILES: COc1cc(N(C)CCN(C)C)c([N+](=O)[O-])cc1Nc1ncnc(-c2cccc3ccn(C)c23)n1]

Compound 78f was prepared in the same manner as compound 78a, except that compound 77c was used instead of compound 77a. MS (ESI) (m/z): [M+H]+ 477.2.

N4-(4-(1H-indol-7-yl)-1,3,5-triazin-2-yl)-N1-(2-(dimethylamino)ethyl)-5-methoxy-N1-toluene-1,2,4-triamine compound 79a)

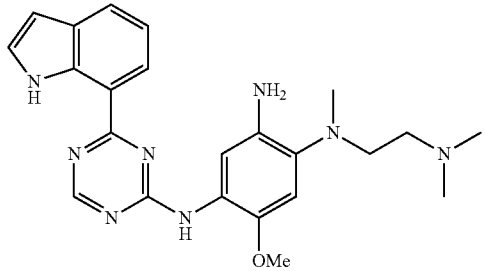

Compound 78a (200 mg, 0.433 mmol) was dissolved in ethanol (20 mL)-water (20 mL) in a 100 mL single neck flask, and iron powder (606 mg, 10.82 mmol) and ammonium chloride (139 mg, 2.6 mmol) were added. The temperature was increased to 50° C. to react for 2 hours. An aqueous solution of saturated sodium carbonate was added to quench the reaction. The mixture was extracted with ethyl acetate for 3 times, dried over sodium sulfate, concentrated, and subjected to column chromatography to obtain product 79a (150 mg, 0.35 mmol). MS (ESI) (m/z): [M+H]+ 433.2.

N4-(4-(1H-indol-7-yl)-1,3,5-triazin-2-yl)-5-(difluoromethoxy)-N1-(2-(dimethylamino)ethyl)-N1-toluene-1,2,4-triamine (compound 79b)

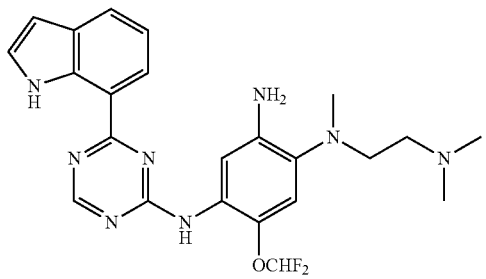

Compound 79b was prepared in the same manner as compound 79a, except that compound 78b was used instead of compound 78a. 1H NMR (400 MHz, CDCl3): δ 10.86 (s, 1H), 8.83 (s, 1f), 8.49-8.42 (m, 1H), 7.90 (d, J=7.7 Hz, 1H), 7.66 (s, 1H), 7.60 (s, 1H), 7.34 (s, 1H), 7.28 (m, 1H), 6.95 (s, 1H), 6.68-6.27 (m, 2H), 2.99 (t, J=6.3 Hz, 2H), 2.74 (s, 3H), 2.49 (t, J=6.3 Hz, 2H), 2.33 (s, 6H); MS (ESI) (m/z): [M+H]+ 469.2.

N1-(4-(1H-indol-7-yl)-1,3,5-triazin-2-yl)-6-methoxy-4-(4-methylpiperazin-1-yl)benzene-, 3-diamine (compound 79c)

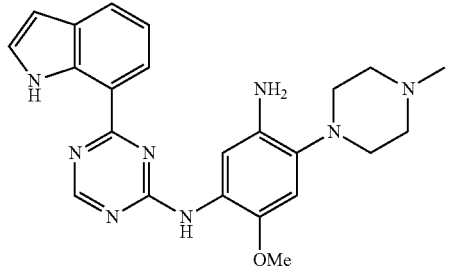

Compound 79c was prepared in the same manner as compound 79a, except that compound 78c was used instead of compound 78a. MS (ESI) (m/z): [M+H]+ 431.2.

N1-(4-(1H-indol-7-yl)-1,3,5-triazin-2-yl)-4-(3-(dimethylamino)azetidin-1-yl)-6-methoxyphenyl-1,3-diamine (compound 79d)

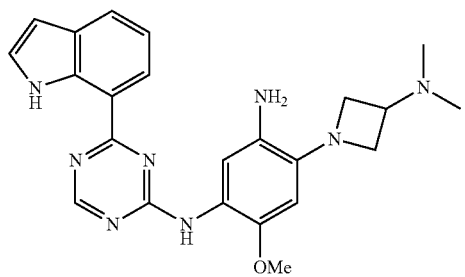 [SMILES: COc1cc(N2CC(N(C)C)C2)c(N)cc1Nc1ncnc(-c2cccc3cc[nH]c23)n1]

Compound 79d was prepared in the same manner as compound 79a, except that compound 78d was used instead of compound 78a. MS (ESI) (m/z): [M+H]+ 431.2.

N1-(4-(1H-indol-7-yl)-1,3,5-triazin-2-yl)-6-ethoxy-4-(5-methyl-2,5-diazaspiro[3.4]oct-2-yl)benzene-1,3-diamine (compound 79e)

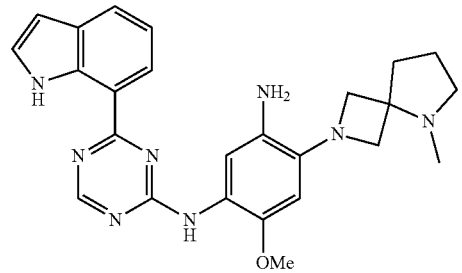

Compound 79e was prepared in the same manner as compound 79a, except that compound 78e was used instead of compound 78a. MS (ESI) (m/z): [M+H]+ 457.2.

N$^1$-(2-(dimethylamino)ethyl)-5-methoxy-N$^1$-methyl-N$^4$-(4-(1-methyl-1H-indol-7-yl)-1,3,5-triazin-2-yl)benzene-1,2,4-triamine (compound 79f)

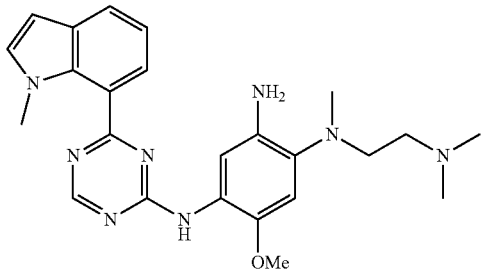

Compound 79f was prepared in the same manner as compound 79a, except that compound 78f was used instead of compound 78a. MS (ESI) (m/z): [M+H]$^+$ 447.3.

Example 32: N-(5-((4-(H-indol-7-yl)-1,3,5-triazin-2-yl)amino)-2-((2-(dimethylamino)ethyl)(methyl)amino)-4-methoxyphenyl)acylamide (compound 80a)

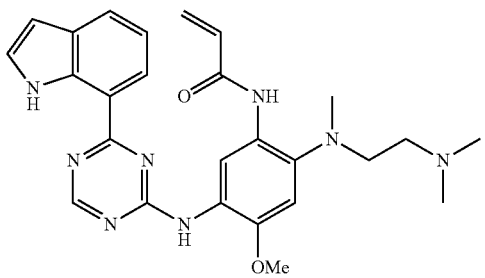 [SMILES: C=CC(=O)Nc1cc(Nc2ncnc(-c3cccc4cc[nH]c34)n2)c(OC)cc1N(C)CCN(C)C]

Compound 79a (200 mg, 0.463 mmol) was dissolved in dichloromethane (20 mL) in a 100 mL single neck flask, and acrylic acid (33.3 mg, 0.463 mmol) and EDCI (222 mg, 1.15 mmol) were added. The mixture was reacted at room temperature for 2 hours. Water was added to quench the reaction. The mixture was extracted 3 times with dichloromethane, dried over sodium sulfate, concentrated, and subjected to column chromatography to obtain product 84a (95 mg, 0.195 mmol). $^1$H NMR (400 MHz, CDCl$_3$): δ 10.94 (s, 1H), 10.20 (s, 1H), 9.68 (s, 1H), 8.89 (s, 1H), 7.89 (d, J=7.7 Hz, 1H), 7.79 (s, 1H), 7.32 (d, J=7.2 Hz, 1H), 6.86 (s, 1H), 6.66-6.49 (m, 2H), 6.41-6.32 (m, 1H), 5.79-5.72 (m, 1H), 3.92 (s, 3H), 2.99-2.88 (m, 2H), 2.77 (s, 3H), 2.40-2.34 (m, 2H), 2.32 (s, 6H); MS (ESI) (m/z): [M+H]$^+$ 487.2.

Example 33: N-(5-((4-(1H-indol-7-yl)-1,3,5-triazin-2-yl)amino)-4-(difluoromethoxy)-2-((2-(dimethylamino)ethyl)(methyl)amino)phenyl)acrylamide (compound 80b)

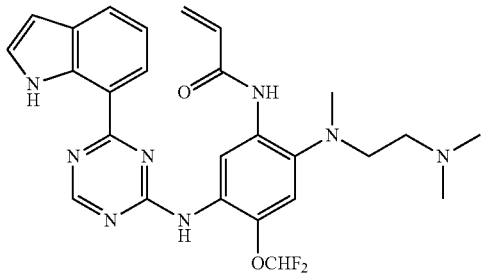 [SMILES: C=CC(=O)Nc1cc(Nc2ncnc(-c3cccc4cc[nH]c34)n2)c(OC(F)F)cc1N(C)CCN(C)C]

Compound 80b was prepared in the same manner as compound 80a, except that compound 79b was used instead of compound 79a. $^1$H NMR (400 MHz, CDCl$_3$): δ 10.90 (s, 1H), 10.36 (s, 1H), 9.69 (s, 1H), 8.88 (s, 1H), 8.72 (s, 1H), 7.90 (d, J=7.7 Hz, 1H), 7.57 (s, 1H), 7.31 (d, J=7.8 Hz, 2H), 7.12 (s, 1H), 6.73-6.34 (m, 4H), 5.80 (d, J=10.2 Hz, 1H), 2.96-2.86 (m, 2H), 2.76 (s, 3H$_1$), 2.45-2.35 (m, 2H), 2.33 (s, 6H); MS (ESI) (m/z): [M+H]$^+$ 523.2.

Example 34: N-(5-((4-(1H-indol-7-yl)-1,3,5-triazin-2-yl)amino)-4-methoxy-2-(4-methylpiperazin-1-yl)phenyl)acrylamide (compound 80c)

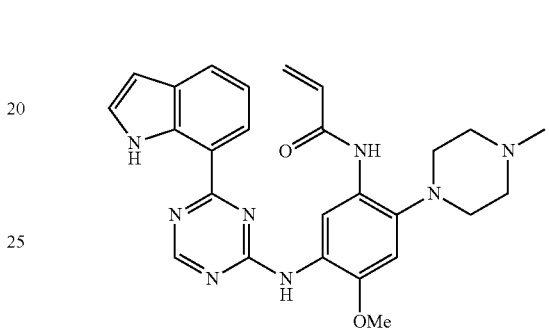

Compound 80c was prepared in the same manner as compound 80a, except that compound 79c was used instead of compound 79a. $^1$H NMR (400 MHz, CDCl$_3$): δ 10.94 (s, 1H), 9.59 (s, 1H), 8.86-8.48 (m, 3H), 7.95-7.76 (m, 2H), 7.41-7.25 (m, 2H), 6.82 (s, 1H), 6.62 (s, 1H), 6.51-6.47 (m, 1H), 6.37-6.30 (m, 1H), 5.81 (d, J=10.3 Hz, 1H), 3.90 (s, 3H), 3.06-3.00 (m, 41H), 2.88-2.80 (m, 4H), 2.51 (s, 3H); MS (ESI) (m/z): [M+H]$^+$ 485.2.

Example 35: N—(5-((4-(1H-indol-7-yl)-1,3,5-triazin-2-yl)amino)-2-(3-(dimethylamino)azetidin-1-yl)-4-methoxyphenyl)acylamide (compound 80d)

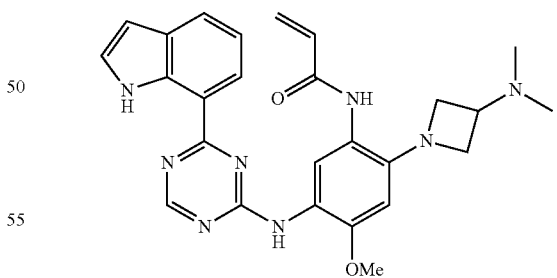

Compound 80d was prepared in the same manner as compound 80a, except that compound 79d was used instead of compound 79a. $^1$H NMR (400 MHz, CDCl$_3$): δ 10.92 (s, 1H), 8.79 (s, 1H), 8.59 (s, 1H), 7.87 (d, J=7.3 Hz, 1H), 7.68 (s, 1H), 7.42-7.21 (m, 4H), 6.61 (s, 1H), 6.52-6.48 (m, 1H), 6.38-6.31 (m, 2H), 5.81 (d, J=10.2 Hz, 1H), 4.13-3.81 (m, 5H), 3.71-3.67 (m, 2H), 3.16-3.12 (m, 1H), 2.22 (s, 6H);MS (ESI) (m/z): [M+H]$^+$ 485.2.

Example 36: N-(5-(((4-(1H-indol-7-yl)-1,3,5-triazin-2-yl)amino)-4-methoxy-2-(5-methyl-2,5-diazaspiro[3.4]oct-2-yl)phenyl)acrylamide (compound 80e)

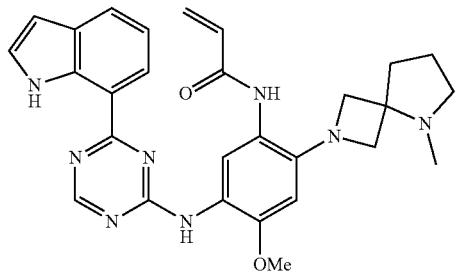 [SMILES: C=CC(=O)Nc1cc(Nc2ncnc(-c3cccc4cc[nH]c34)n2)c(OC)cc1N1CC2(CCCN2C)C1]

Compound 80e was prepared in the same manner as compound 80a, except that compound 79e was used instead of compound 79a. ¹H NMR (400 MHz, CDCl₃): δ 11.05-10.71 (m, 1H), 8.72 (s, 1H), 8.58-8.00 (m, 2H), 7.85-7.56 (m, 3H), 7.31 (s, 1H), 7.21 (t, J=7.6 Hz, 1H), 6.65-6.29 (m, 3H), 6.05 (s, 1H), 5.77 (d, J=10.7 Hz, 1H), 4.02-4.00 (m, 2H), 3.79 (s, 3H), 3.65-3.63 (m, 2H), 2.88-2.73 (m, 2H), 2.53 (s, 3H), 2.12-2.10 (m, 2H), 1.81-1.77 (m, 2H); MS (ESI) (m/z): [M+H]⁺ 511.3.

Example 37: N-(2-((2-(dimethylamino)ethyl)(methyl)amino)-4-methoxy-5-((4-(1-methyl-1H-indol-7-yl)-1,3,5-triazin-2-yl)amino)phenyl)acrylamide (compound 80f)

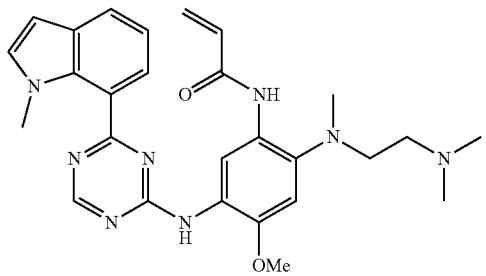 [SMILES: C=CC(=O)Nc1cc(Nc2ncnc(-c3cccc4ccn(C)c34)n2)c(OC)cc1N(C)CCN(C)C]

Compound 80f was prepared in the same manner as compound 80a, except that compound 79f was used instead of compound 79a. ¹H NMR (400 MHz, CDCl₃): δ 10.14 (s, 1H), 9.65 (s, 1H), 8.98 (s, 1H), 7.87 (s, 1H), 7.79 (d, J=7.2 Hz, 1H), 7.24 (t, J=7.7 Hz, 1H), 7.09 (d, J=3.1 Hz, 1H), 6.83 (s, 1H), 6.60 (d, J=3.1 Hz, 1H), 6.49 (d, J=15.7 Hz, 1H), 6.39-6.28 (m, 1H), 5.73 (d, J=10.6 Hz, 1H), 3.90 (s, 3H), 3.76 (s, 3H), 2.99-2.86 (m, 2H), 2.75 (a, 3H), 2.33 (m, 81H).

The synthesis route of compound 85 is as shown in Scheme 9:

Scheme 9

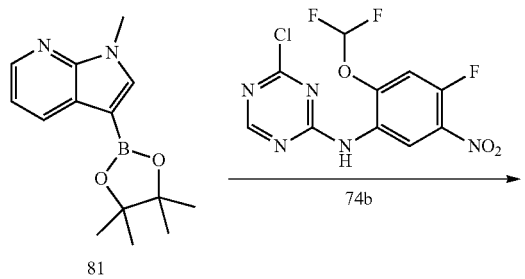

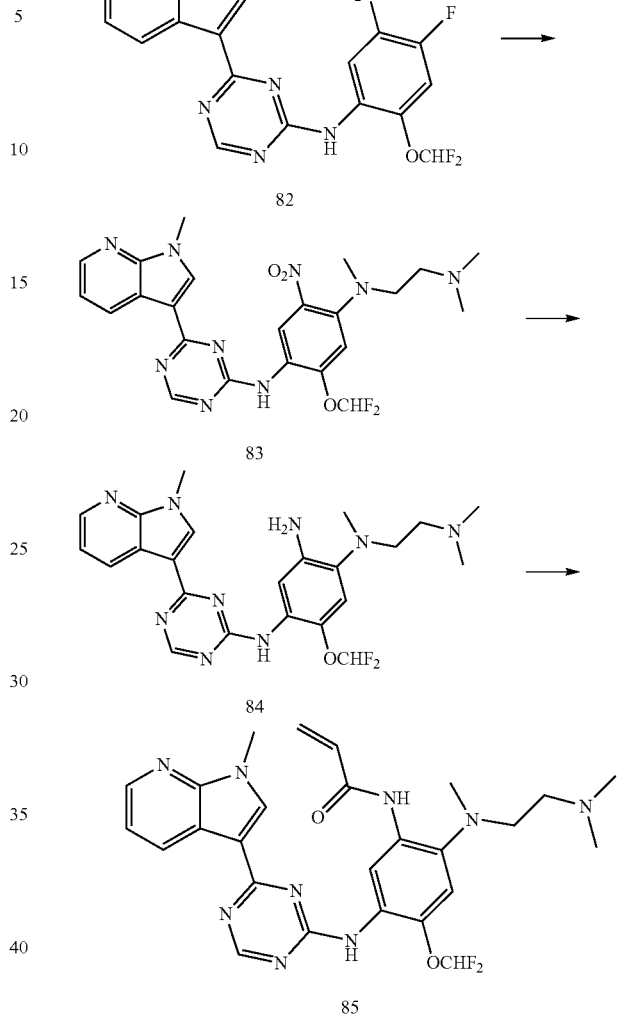

N-(2-(difluoromethoxy)-4-fluoro-5-nitrophenyl)-4-(1-methyl-1H-pyrrolo[2,3-b]pyridin-3-yl)-1,3,5-triazin-2-amine (compound 82)

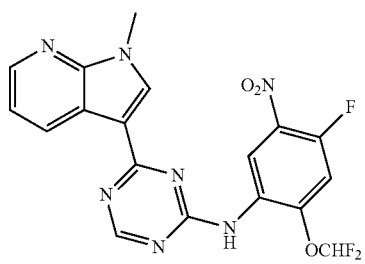 [SMILES: Cn1cc(-c2ncnc(Nc3cc([N+](=O)[O-])c(F)cc3OC(F)F)n2)c2cccnc21]

Compound 81 (15 g, 0.058 mol) was dissolved in 1,4-dioxane (150 mL) and water (50 mL), then compound 74b (13 g, 0.038 mol) and sodium carbonate (12.3 g, 0.116 mol) were added. After 3 times of nitrogen replacement, tetrakis(triphenylposhine)palladium (9 g, 0.008 mol) was added and the air was further replaced 3 times with nitrogen. The mixture was heated to 90° C. in an oil bath to react, and the reaction was complete after 1 h. The mixture was filtered with suction through celite, and purified by column chromatography to obtain compound 82 (7 g, 41.90%). ¹H NMR (400 MHz, CDCl₃): δ 9.80 (s, 1H), 8.85-8.83 (m, 1H), 8.80 (s, 1H), 8.47-8.45 (m, 2H), 7.48-7.45 (m, 1H), 7.33-7.30 (m, 1H), 7.22 (d, J=10.7 Hz, 1H), 6.97-6.59 (m, 1H), 4.05 (s, 3H); MS (ESI) (m/z): [M+H]⁺ 432.1.

2-(difluoromethoxy)-N⁴-(2-(dimethylamino)ethyl)-N⁴-methyl-N¹-(4-(1-methyl-1H-pyrrolo[2,3-b]pyridin-3-yl)-1,3,5-triazin-2-yl)-5-nitrobenzene-1,4-diamine (compound 83)

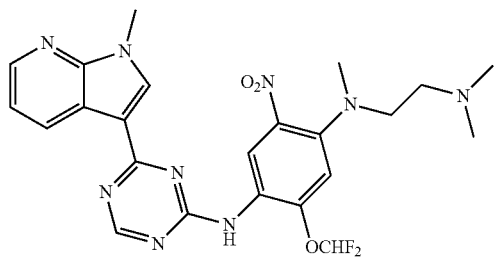

Compound 82 (7 g, 0.016 mol) was dissolved in DMF (100 mL), N,N-diisopropylethylamine (2.73 g, 0.021 mol) and N,N,N'-trimethylethylenediamine (1.99 g, 0.019 mol) were added to the reaction solution, and the mixture was heated to 80° C. in an oil bath and stirred. The reaction was complete in 0.5 hour. Water (100 mL) was added to quench the reaction. The mixture was extracted with dichloromethane, washed twice with saturated brine, and purified by column chromatography to obtain compound 83 (3.0 g, 36.14%). ¹H NMR (400 MHz, CDCl₃): δ 9.23 (s, 1H), 8.82-8.80 (m, 1H), 8.72 (s, 1H), 8.44-8.43 (m, 1H), 8.41 (s, 1H), 7.43 (s, 1H), 7.31-7.28 (m, 1H), 7.05 (s, 1H), 6.91-6.48 (m, 1H), 4.03 (s, 3H), 3.33 (t, J=7.0 Hz, 2H), 2.93 (d, J=10.1 Hz, 3H), 2.59 (t, J=7.0 Hz, 2H), 2.29 (s, 6H); MS (ESI) (m/z): [M+H]⁺ 514.2.

5-(difluoromethoxy)-N¹-(2-(dimethylamino)ethyl)-N¹-methyl-N⁴-(4-(1-methyl-H-pyrrolo[2,3-b]pyridin-3-yl)-1,3,5-triazin-2-yl)benzene-1,2,4-triamine (compound 84)

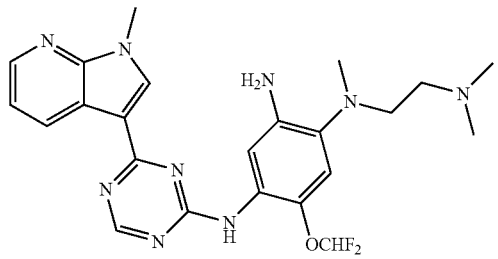 [SMILES: CN(C)CCN(C)c1cc(OC(F)F)c(Nc2ncnc(-c3cn(C)c4ncccc34)n2)cc1[N+](=O)[O-]]

Compound 83 (3.2 g, 6.23 mmol) was dissolved in ethanol (30 mL), water (10 mL) was added, then iron powder (2.09 g, 37.42 mmol) and ammonium chloride (0.23 g, 4.30 mmol) were added to the reaction solution, and the mixture was stirred and heated to 80° C. in an oil bath. The reaction was complete after 3 h. The reaction solution was filtered with suction directly. The filtrate was spin-dried and purified by column chromatography to obtain compound 84 (3.1 g, 99.7%). MS (ESI) (m/z): [M+H]⁺ 484.2.

Example 38: N-(4-(difluoromethoxy)-2-((2-(dimethylamino)ethyl)(methyl)amino)-5-((4-(1-methyl-1H-pyrrolo[2,3-b]pyridin-3-yl)-1,3,5-triazin-2-yl)amino)phenyl)acrylamide (compound 85)

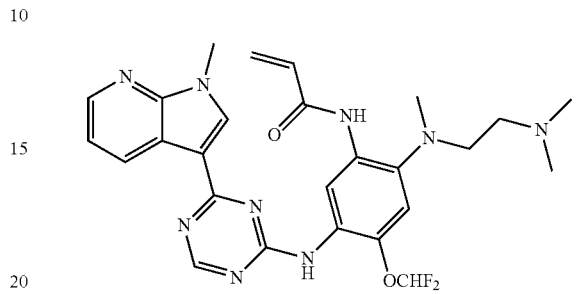

Compound 84 (3.1 g, 6.41 mmol) was dissolved in dichloromethane (50 mL), and tert-butanol (5 mL) was added. The mixture was cooled in an ice water bath, and acrylic acid (0.92 g, 12.77 mmol), EDCI (2.46 g, 12.83 mmol), and triethylamine (1.30 g, 12.87 mmol) were added. The reaction was complete after 3 h. Saturated potassium carbonate solution was added and stirred for 10 min. The mixture was extracted with dichloromethane, and purified by column chromatography to obtain compound 85 (1.1 g, 31.9%). ¹H NMR (400 MHz, CDCl₃): δ 10.41 (s, 1H), 10.03 (s, 1H), 9.39 (bs, 1H), 8.87-8.85 (m, 1H), 8.76 (s, 1H), 8.43-8.41 (m, 1H), 7.56 (s, 1-), 7.26-7.24 (m, 1H), 7.11 (s, 1H), 6.76-6.33 (m, 3H), 5.83-5.81 (m, 1H), 4.10 (s, 3H), 2.93-2.85 (m, 2H), 2.75 (s, 3H), 2.36-2.34 (m, 2H), 2.32 (s, 6H); MS (ESI) (m/z): [M+H]⁺538.2.

The synthesis route of compound 89 is as shown in Scheme 10:

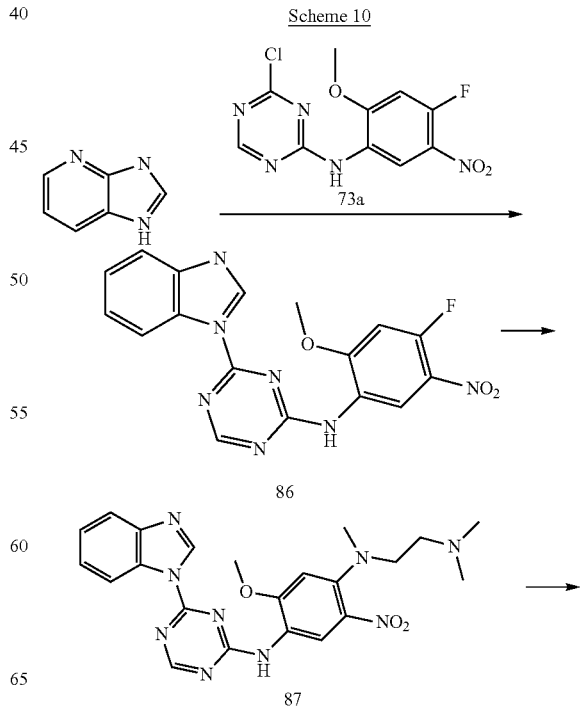

-continued

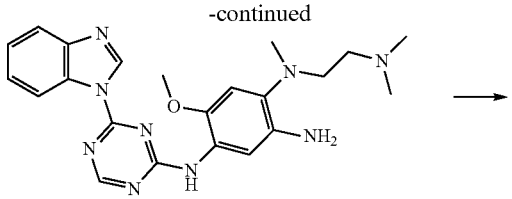

88

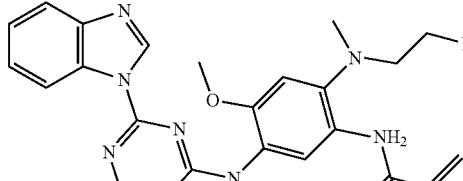

89

Synthesis of 4-(1H-benzo[d]imidazol-1-yl)-N-(4-fluoro-2-methoxy-5-nitrophenyl)-1,3,5-triazin-2-amine (compound 86

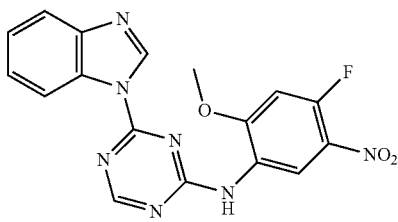 [SMILES: COc1cc(F)c([N+](=O)[O-])cc1Nc1ncnc(-n2cnc3ccccc32)n1]

Compound 74a (500 nag, 1.67 mmol) was dissolved in DMF (30 mL) in a 100 mL single neck flask, and benzimidazole (179 mg, 1.52 mmol) and potassium carbonate (419 mg, 3.04 mmol) were added. The mixture was reacted at room temperature for 16 h. Water was added to quench the reaction. The mixture was extracted with ethyl acetate for 3 times, dried over sodium sulfate, concentrated, and subjected to column chromatography to obtain compound 86 (300 mg, 0.785 mmol). $^1$H NMR (400 MHz, d$_6$-DMSO): δ 10.17 (s, 1H), 9.14-8.95 (m, 1H), 8.81 (s, 1H), 8.61-8.52 (m, 1H), 7.79 (d, J=7.3 Hz, 1H), 7.57-7.18 (s, 3H), 3.99 (s, 3H); MS (ESI) (m/z): [M+H]$^+$ 382.1.

$N^1$-(4-(1H-benzo[d]imidazol-1-yl)-1,3,5-triazin-2-yl)-$N^4$-(2-(dimethylamino)ethyl)-2-methoxy-$N^4$-methyl-5-nitrobenzene-1,4-diamine (compound 87)

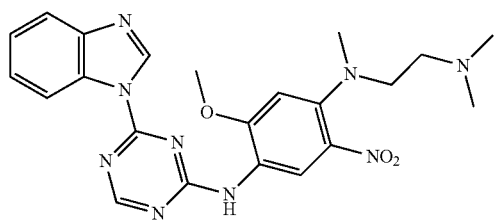 [SMILES: COc1cc(N(C)CCN(C)C)c([N+](=O)[O-])cc1Nc1ncnc(-n2cnc3ccccc32)n1]

Compound 86 (650 mg, 1.7 mmol) was dissolved in N,N-dimethylacetamide (50 mL) in a 100 mL single neck flask, and N,N,N'-trimethylethylenediamine (297 mg, 2.6 mmol) and N,N-diisopropylethylamine (658 mg, 5.1 mmol) were added. The temperature was increased to 60° C. to react for 2 h. Water was added to quench the reaction. The mixture was extracted with ethyl acetate for 3 times, dried over sodium sulfate, concentrated, and subjected to column chromatography to obtain compound 87 (300 mg, 0.65 mmol). $^1$H NMR (400 MHz, CDCl$_3$) δ 9.12-8.63 (m, 3H), 8.59-8.46 (m, 1H), 7.84 (d, J=7.8 Hz, 1H), 7.81-7.69 (m, 1H), 7.47-7.38 (m, 2H), 6.71 (s, 1H), 3.99 (s, 3H), 3.36 (s, 2H), 2.94 (s, 3H), 2.62 (t, J=6.7 Hz, 2H), 2.30 (s, 6H); MS (ESI) (m/z): [M+H]$^+$ 464.2.

$N^4$-(4-(1H-benzo[d]imidazol-1-yl)-1,3,5-triazin-2-yl)-$N^1$-(2-(dimethylamino)ethyl)-5-methoxy-$N^1$-toluene-1,2,4-triamine (compound 88)

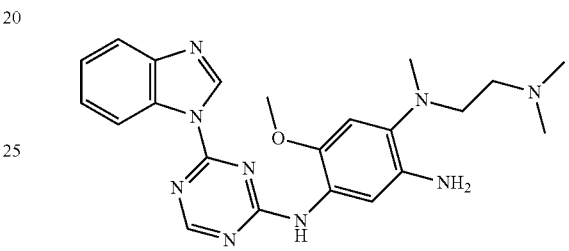

Compound 87 (500 mg, 1.08 mmol) was dissolved in ethanol (20 mL)-water (2 mL) in a 100 mL single neck flask, and iron powder (604 mg, 10.08 mmol) and ammonium chloride (604 mg, 10.08 mmol) were added. The temperature was increased to 50° C. to react for 2 h. An aqueous solution of saturated sodium carbonate was added to quench the reaction. The mixture was extracted with ethyl acetate for 3 times, dried over sodium sulfate, concentrated, and subjected to column chromatography to obtain compound 88 (250 mg, 0.577 mmol). MS (ESI) (m/z): [M+H]$^+$ 434.2.

Example 39: N-(5-((4-(1H-benzo[d]imidazol-1-yl)-1,3,5-triazin-2-yl)amino)-2-((2-(dimethylamino)ethyl)(methyl)amino)-4-methoxyphenyl)acrylamide (compound 89)

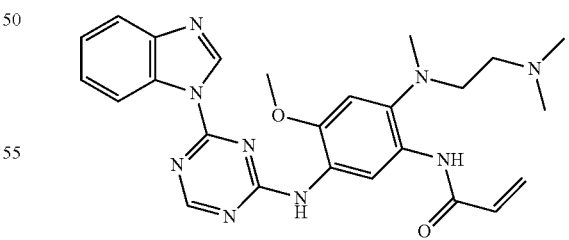

Compound 89 was prepared in the same manner as compound 85, except that compound 88 was used instead of compound 84. $^1$H NMR (400 MHz, CDCl$_3$): δ 10.23 (s, 1H), 9.74 (s, 2H), 9.61 (s, 1H), 8.73 (s, 1H), 8.61 (s, 1H), 7.98 (s, 1H), 7.88-7.86 (m, 1H), 7.38 (m, 2H), 6.70-6.36 (m, 2H), 5.76 (d, J=10.7 Hz, 1H), 3.93 (s, 3H), 2.93 (s, 2H), 2.77 (s, 3H), 2.33 (s, 8H); MS (ESI) (m/z): [M+H]$^+$ 488.2.

The synthesis route of compounds 97a-97e is as shown in Scheme 11:

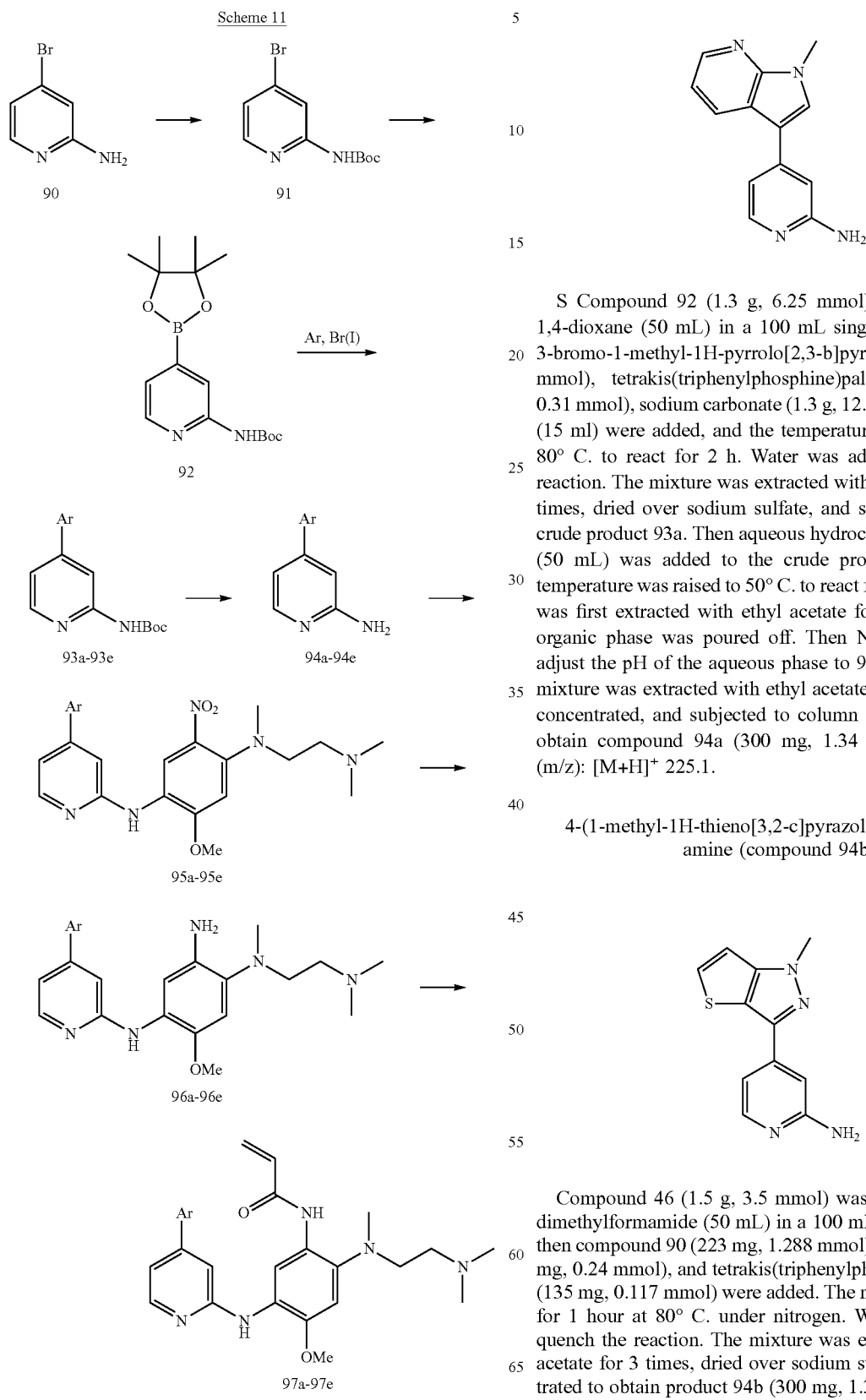

4-(1-methyl-1H-pyrrolo[2,3-b]pyridin-3-yl)pyridin-2-amine (compound 94a)

S Compound 92 (1.3 g, 6.25 mmol) was dissolved in 1,4-dioxane (50 mL) in a 100 mL single neck flask, then 3-bromo-1-methyl-1H-pyrrolo[2,3-b]pyridine (2 g, 6.25 mmol), tetrakis(triphenylphosphine)palladium (360 mg, 0.31 mmol), sodium carbonate (1.3 g, 12.5 mmol), and water (15 ml) were added, and the temperature was increased to 80° C. to react for 2 h. Water was added to quench the reaction. The mixture was extracted with ethyl acetate for 3 times, dried over sodium sulfate, and spin-dried to obtain crude product 93a. Then aqueous hydrochloric acid solution (50 mL) was added to the crude product 93a, and the temperature was raised to 50° C. to react for 2 h. The mixture was first extracted with ethyl acetate for 2 times, and the organic phase was poured off. Then NaOH was used to adjust the pH of the aqueous phase to 9. Subsequently, the mixture was extracted with ethyl acetate for 3 times, dried, concentrated, and subjected to column chromatography to obtain compound 94a (300 mg, 1.34 mmol). MS (ESI) (m/z): $[M+H]^+$ 225.1.

4-(1-methyl-1H-thieno[3,2-c]pyrazol-3-yl)pyridin-2-amine (compound 94b)

Compound 46 (1.5 g, 3.5 mmol) was dissolved in N,N-dimethylformamide (50 mL) in a 100 mL single neck flask, then compound 90 (223 mg, 1.288 mmol), copper iodide (44 mg, 0.24 mmol), and tetrakis(triphenylphosphine)palladium (135 mg, 0.117 mmol) were added. The mixture was reacted for 1 hour at 80° C. under nitrogen. Water was added to quench the reaction. The mixture was extracted with ethyl acetate for 3 times, dried over sodium sulfate, and concentrated to obtain product 94b (300 mg, 1.3 mmol). MS (ESI) (m/z): $[M+H]^+$ 231.1.

4-(1-methyl-1H-pyrazolo[4,3-c]pyridin-3-yl)pyridin-2-amine (compound 94c)

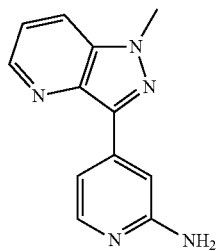 [SMILES: Cn1nc(-c2ccnc(N)c2)c2ncccc21]

Compound 92 (1.3 g, 4.06 mmol) was dissolved in 1,4-dioxane (50 mL) in a 100 mL single neck flask, then 3-iodo-1-methyl-1H-pyrazolo[4,3-b]pyridine (400 mg, 1.54 mmol), tetrakis(triphenylphosphine)palladium (178 mg, 0.308 mmol), sodium carbonate (408 ms, 3.85 mmol) and water (15 ml) were added, and the temperature was increased to 80° C. to react for 2 hours. Water was added to quench the reaction. The mixture was extracted with ethyl acetate for 3 times, dried over sodium sulfate, and concentrated to obtain crude product 93c. Then aqueous hydrochloric acid solution (50 ml) was added to the crude product, and the temperature was raised to 50° C. to react for 2 h. The mixture was first extracted with ethyl acetate for 2 times, and the organic layer was poured off. Then NaOH was used to adjust the pH of the aqueous phase to 9. Subsequently, the mixture was extracted with ethyl acetate for 3 times, dried, concentrated, and subjected to column chromatography to obtain product 94c (350 mg, 1.56 mmol). MS (ESI) (m/z): $[M+H]^+$ 226.1.

4-(pyrazolo[1,5-a]pyrimidin-3-yl)pyridin-2-amine (compound 94d)

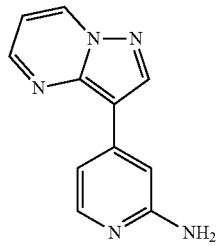 [SMILES: Nc1cc(-c2cnn3cccnc23)ccn1]

Compound 94d was prepared in the same manner as compound 94a, except that 3-bromopyrazolo[1,5-a]pyrimidine was used instead of 3-bromo-1-methyl-1H-pyrrolo[2,3-b]pyridine. $^1$H NMR (400 MHz, $d_6$-DMSO): δ 9.23-9.19 (m, 1H), 8.75 (s, 1H), 8.73-8.71 (m, 1H), 7.92 (d, J=5.2 Hz, 1H), 7.31 (s, 1H), 7.22-7.14 (m, 2H), 5.90 (bs, 2H); MS (ESI) (m/z): $[M+H]^+$ 212.1.

4-(imidazo[1,2-a]pyridin-3-yl)pyridin-2-amine (compound 94e)

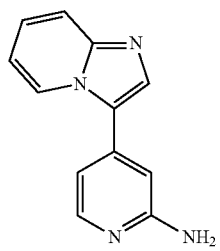 [SMILES: Nc1cc(-c2cnc3ccccn23)ccn1]

Compound 94e was prepared in the same manner as compound 94a, except that 3-bromoimidazo[1,2-a]pyridine was used instead of 3-bromo-1-methyl-1H-pyrrolo[2,3-b]pyridine. MS (ESI) (m/z): $[M+H]^+$ 211.1.

$N^1$-(2-(dimethylamino)ethyl)-5-methoxy-$N^1$-methyl-$N^4$-(4-(1-methyl-1H-pyrrolo[2,3-b]pyridin-3-yl)pyridin-2-yl)-2-nitrobenzene-1,4-diamine (compound 95a)

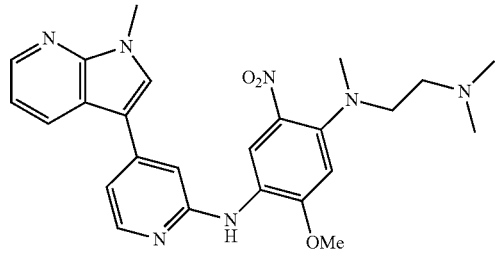 [SMILES: COc1cc(N(C)CCN(C)C)c([N+](=O)[O-])cc1Nc1cc(-c2cn(C)c3ncccc23)ccn1]

Compound 94a (400 mg, 1.79 mmol) was dissolved in DMF (50 mL) in a 100 mL single neck flask, and compound 11a (886 mg, 2.7 mmol), tri(dibenzylideneacetone)dipalladium (16 mg, 0.0179 mmol), 4,5-bis(diphenylphosphino)-9,9-dimethylxanthene (21 mg, 0.0358 mmol) and cesium carbonate (1.75 g, 5.37 mmol) were added. The temperature was increased to 85° C. to react for 12 hours. Water was added to quench the reaction. The mixture was extracted with ethyl acetate for 3 times, dried over sodium sulfate, concentrated, and subjected to column chromatography to obtain compound 95a (300 mg, 0.63 mmol). MS (ESI) (m/z): $[M+H]^+$ 476.2.

$N^1$-(2-(dimethylamino)ethyl)-5-methoxy-$N^1$-methyl-$N^4$-(4-(1-methyl-1H-thieno[3,2-c]pyrazol-3-yl)pyridin-2-yl)-2-nitrobenzene-1,4-diamine (compound 95b)

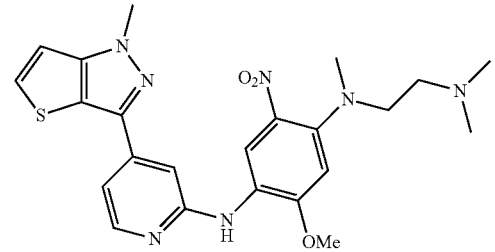 [SMILES: COc1cc(N(C)CCN(C)C)c([N+](=O)[O-])cc1Nc1cc(-c2nn(C)c3ccsc23)ccn1]

Compound 95b was prepared in the same manner as compound 95a, except that compound 94b was used instead of compound 94a. MS (ESI) (m/z): $[M+H]^+$ 482.2.

$N^1$-(2-(dimethylamino)ethyl)-5-methoxy-$N^1$-methyl-$N^4$-(4-(1-methyl-1H-pyrazolo[4,3-c]pyridin-3-yl)pyridin-2-yl)-2-nitrobenzene-1,4-diamine (compound 95c)

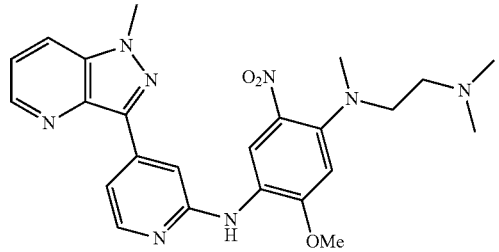 [SMILES: COc1cc(N(C)CCN(C)C)c([N+](=O)[O-])cc1Nc1cc(-c2nn(C)c3cccnc23)ccn1]

Compound 95c was prepared in the same manner as compound 95a, except that compound 94c was used instead of compound 94a. MS (ESI) (m/z): [M+H]+ 477.2.

N$^1$-(2-(dimethylamino)ethyl)-5-methoxy-N$^1$-methyl-2-nitro-N$^1$-(4-(pyrazolo[1,5-a]pyrimidin-3-yl)pyridin-2-yl)benzene-1,4-diamine (compound 95d)

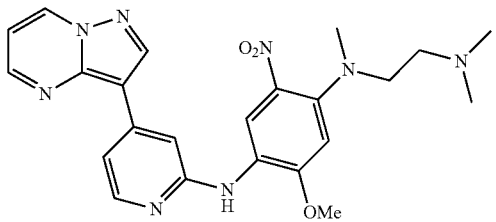 [SMILES: COc1cc(N(C)CCN(C)C)c([N+](=O)[O-])cc1Nc1cc(-c2cnn3cccnc23)ccn1]

Compound 95d was prepared in the same manner as compound 95a, except that compound 94d was used instead of compound 94a. MS (ESI) (m/z): [M+H]+ 463.1.

N$^1$-(2-(dimethylamino)ethyl)-N-(4-(imidazo[1,2-a]pyridin-3-yl)pyridin-2-yl)-5-methoxy-N-methyl-2-nitrobenzene-1,4-diamine (compound 95e)

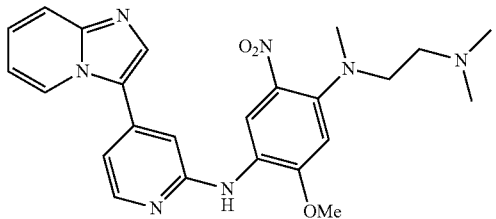 [SMILES: COc1cc(N(C)CCN(C)C)c([N+](=O)[O-])cc1Nc1cc(-c2cnc3ccccn23)ccn1]

Compound 95e was prepared in the same manner as compound 95a, except that compound 94e was used instead of compound 94a. $^1$H NMR (400 MHz, CDCl$_3$): δ 8.82 (s, 1H), 8.53 (d, J=7.0 Hz, 1H), 8.43-8.35 (m, 1H), 7.85 (s, 1H), 7.73 (d, J=9.1 Hz, 1H), 7.35-7.26 (m, 1H), 7.05-6.95 (m, 3H), 6.91 (s, 1H), 6.71 (s, 1H), 3.99 (s, 3H), 3.35-3.26 (m, 2H$_{11}$), 2.90 (s, 3H), 2.67-2.56 (m, 2H), 2.30 (s, 6H); MS (ESI) (m/z): [M+H]+ 462.2.

N$^1$-(2-(dimethylamino)ethyl)-5-methoxy-N$^1$-methyl-N$^4$-(4-(1-methyl-1H-pyrrolo[2,3-b]pyridin-3-yl)pyridin-2-yl)benzene-1,2,4-triamine (compound 96a)

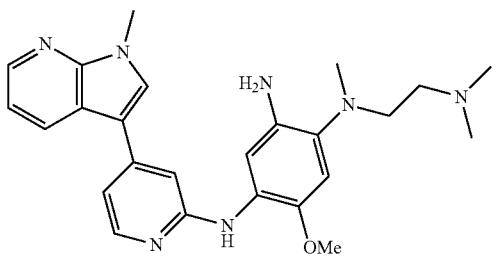

Compound 95a (475 mg, 2.37 mmol) was dissolved in ethanol (20 mL)-water (20 mL) in a 100 mL single neck flask, and iron powder (1.3 g, 23.75 mmol) and ammonium chloride (1.3 g, 23.75 mmol) were added. The temperature was increased to 50° C. to react for 2 hours. An aqueous solution of saturated sodium carbonate was added to quench the reaction. The mixture was extracted with ethyl acetate for 3 times, dried over sodium sulfate, concentrated, and subjected to column chromatography to obtain product 96a (100 mg, 0.224 mmol). MS (ESI) (m/z): [M+H]+ 446.3.

N$^1$-(2-(dimethylamino)ethyl)-5-methoxy-N$^1$-methyl-N$^4$-(4-(1-methyl-1H-thieno[3,2-c]pyrazol-3-yl)pyridin-2-yl)benzene-1,2,4-triamine (compound 96b)

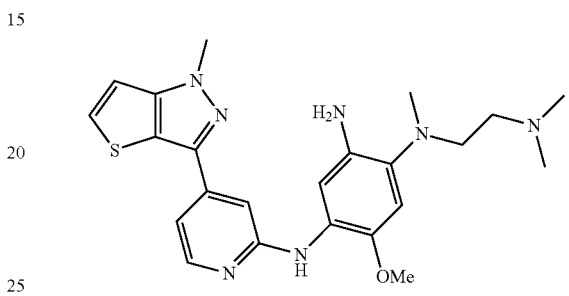

Compound 96b was prepared in the same manner as compound 96a, except that compound 95b was used instead of compound 95a. MS (ESI) (m/z): [M+H]+ 452.2.

N$^1$-(2-(dimethylamino)ethyl)-5-methoxy-N$^1$-methyl-N$^4$-(4-(1-methyl-1H-pyrazolo[4,3-c]pyridin-3-yl)pyridin-2-yl)benzene-1,2,4-triamine (compound 96c)

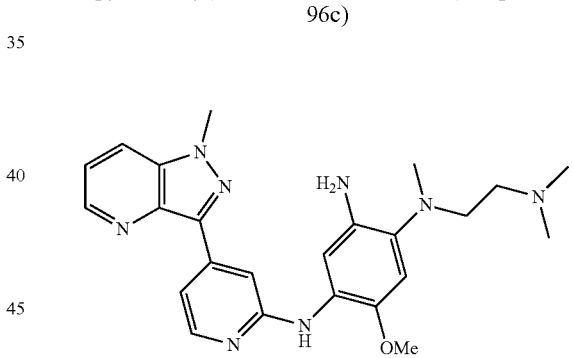

Compound 96c was prepared in the same manner as compound 96a, except that compound 95c was used instead of compound 95a. MS (ESI) (m/z): [M+H]+ 447.3.

N$^1$-(2 (dimethylamino)ethyl)-5-methoxy-N$^1$-methyl-N$^4$-(4-(pyrazolo[1,5-a]pyrimidin-3-yl)pyridin-2-yl)benzene-1,2,4-triamine (compound 96d)

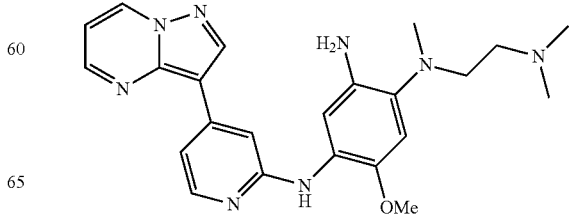

Compound 96d was prepared in the same manner as compound 96a, except that compound 95d was used instead of compound 95a. $^1$H NMR (400 MHz, d$_6$-DMSO): δ 9.25-9.21 (m, 1H), 8.78 (s, 1H), 8.75-8.71 (m, 1H), 8.13-8.10 (d, J=5.2 Hz, 1H), 7.69 (s, 1H), 7.63 (s, 1H), 7.49 (s, 1H), 7.48-7.43 (m, 1H), 7.21-7.17 (m, 1H), 6.74 (s, 1H), 3.75 (s, 3H), 3.18 (s, 3H), 2.90 (t, J=7.2 Hz, 2H), 2.42 (t, J=7.2 Hz, 2H), 2.23 (s, 6H); MS (ESI) (m/z): [M+H]$^+$ 433.2.

$N^1$-(2-(dimethylamino)ethyl)-$N^4$-(4-imidazo[1,2-a]pyridin-3-yl)pyridin-2-yl)-5-methoxy-$N^1$-toluene-1,2,4-triamine (compound 96e)

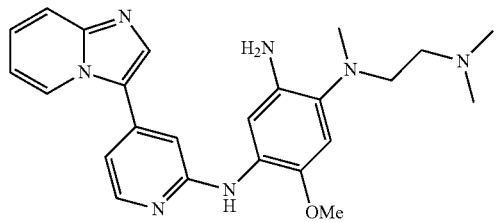

Compound 96e was prepared in the same manner as compound 96a, except that compound 95e was used instead of compound 95a. MS (ESI) (m/z): [M+H]$^+$ 432.2.

Example 40: N-(2-((2-(dimethylamino)ethyl)(methyl)amino)-4-methoxy-5-((4-(1-methyl-1H-pyrrolo[2,3-b]pyridin-3-yl)pyridin-2-yl)amino)phenyl)acrylamide (compound 97a)

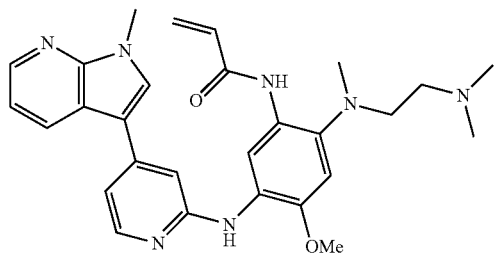 [SMILES: C=CC(=O)Nc1cc(Nc2cc(-c3cn(C)c4ncccc34)ccn2)c(OC)cc1N(C)CCN(C)C]

Compound 96a (445 mg, 0.45 mmol) was dissolved in dichloromethane (50 mL) in a 100 mL single neck flask, and acrylic acid (72 mg, 0.67 mmol) and EDCI (173 mg, 0.9 mmol) were added. The mixture was reacted at room temperature for 2 hours, and water was added to quench the reaction. The mixture was extracted 3 times with DCM, dried over sodium sulfate, concentrated, and subjected to column chromatography to obtain product 97a (30 mg, 0.06 mmol). $^1$H NMR (400 MHz, CD$_3$OD): δ 8.52 (s, 1H), 8.45 (dd, J=8.0, 1.3 Hz, 1H), 8.38-8.32 (m, 1H), 8.12 (d, J=5.4 Hz, 1H), 8.06 (s, 1H), 7.41 (s, 1H), 7.24 (dd, J=8.0, 4.8 Hz, 1H), 7.16 (dd, J=5.5, 1.4 Hz, 1H), 7.00 (s, 1H), 6.62-6.55 (m, 1H), 6.48-6.41 (m, 1H), 5.86-5.83 (m, 1H), 3.96 (d, J=3.8 Hz, 6H), 3.20 (s, 2H), 2.73 (s, 3H), 2.50 (s, 5H); MS (ESI) (m/z): [M+H]$^+$ 500.3.

Example 41: N-(2-((2-(dimethylamino)ethylmethyl)amino)-4-methoxy-5-((4-(1-methyl-1H-thieno[3,2-c]pyrazol-3-yl)pyridin-2-yl)amino)phenyl)acrylamide (compound 97b)

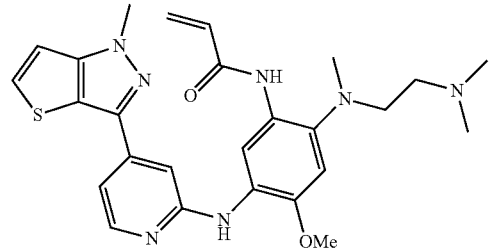 [SMILES: C=CC(=O)Nc1cc(Nc2cc(-c3nn(C)c4ccsc34)ccn2)c(OC)cc1N(C)CCN(C)C]

Compound 97b was prepared in the same manner as compound 97a, except that compound 96b was used instead of compound 96a. $^1$H NMR (400 MHz, CD$_3$OD) δ 8.58 (s, 1H), 8.18-8.11 (m, 1H), 7.61 (d, J=5.3 Hz, 1H), 7.21 (d, J=1.7 Hz, 2H), 7.15 (d, J=5.3 Hz, 1H), 7.00 (s, 1H), 6.63-6.48 (m, 1H), 6.40-6.29 (min, 1H), 5.80 (d, J=10.2 Hz, 1H), 4.09 (s, 3H), 3.92 (s, 4H), 3.13 (t, J=5.5 Hz, 3H), 2.72 (d, J=5.9 Hz, 3H), 2.59 (s, 2H), 2.39 (s, 6H); MS (ESI) (m/z): [M+H]$^+$ 506.2.

Example 42: N-(2-((2-(dimethylamino)ethyl)(methyl)amino)-4-methoxy-5-((4-(1-methyl-1H-pyrazolo[4,3-b]pyridin-3-yl)pyridin-2-yl)amino)phenyl)acrylamide (compound 97c)

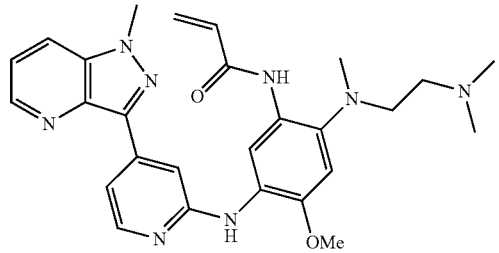 [SMILES: C=CC(=O)Nc1cc(Nc2cc(-c3nn(C)c4cccnc34)ccn2)c(OC)cc1N(C)CCN(C)C]

Compound 97c was prepared in the same manner as compound 97a, except that compound 96c was used instead of compound 96a. $^1$H NMR (400 MHz. CD$_3$OD) δ 8.72 (d, J=11.8 Hz, 1H), 8.63 (m, 1H), 8.20 (d, J=5.4 Hz, 1H), 8.12-8.06 (m, 2H), 7.75 (m, 1H), 7.46 (m, 1H), 6.99 (s, 1H), 6.55-6.50 (m, 1H), 6.35 (m, 1H), 5.79 (d, J=10.2 Hz, 1H), 4.18 (s, 3H), 3.93 (d, J=4.8 Hz, 3H), 3.11 (d, J=5.5 Hz, 2H), 2.72 (s, 3H), 2.36 (m, 6H); MS (ESI) (m/z): [M+H]$^+$ 501.3.

Example 43: N-(2-((2-(dimethylamino)ethyl)(methyl)amino)-4-methoxy-5-((4-(pyrazolo[1,5-a]pyrimidin-3-yl)pyridin-2-yl)amino)phenyl)acrylamide (compound 97d)

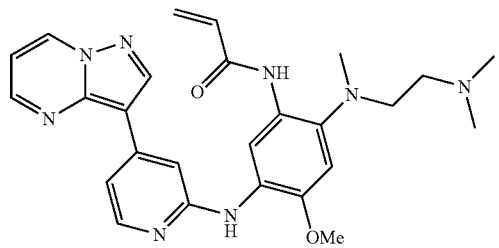 [SMILES: C=CC(=O)Nc1cc(Nc2cc(-c3cnn4cccnc34)ccn2)c(OC)cc1N(C)CCN(C)C]

Compound 97d was prepared in the same manner as compound 97a, except that compound 96d was used instead of compound 96a. $^1$H NMR (400 MHz. CDCl$_3$): δ 10.07 (bs, 1H), 9.06 (s, 1H), 8.87 (bs, 1H), 8.74-8.70 (m, 1H), 8.63-8.59 (m, 1H), 8.28 (d, J=5.2 Hz, 1H), 7.82 (s, 1H), 7.64-7.60 (m, 1H), 7.14 (s, 1H), 6.93-6.87 (m, 1H), 6.78 (s, 1H), 6.52-6.38 (m, 2H), 5.73-5.67 (m, 1H), 3.87 (s, 3H), 2.94 (t, J=7.2 Hz, 2H), 2.71 (s, 3H), 2.41 (t, J=7.2 Hz, 2H), 2.34 (s, 6H); MS (ESI) (m/z): [M+H]$^+$ 487.2.

Example 44: N-(2-((2-(dimethylamino)ethyl) (methyl)amino)-5-((4-(imidazo[1,2-a]pyridin-3-yl) pyridin-2-yl)amino)-4-methoxyphenyl)acrylamide (compound 97e)

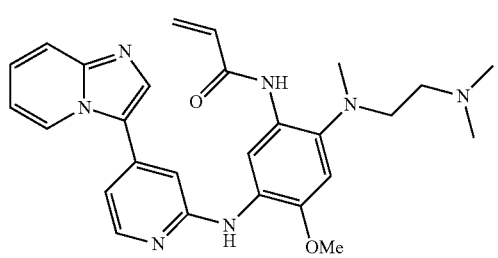 [SMILES: C=CC(=O)Nc1cc(Nc2cc(-c3cnc4ccccn34)ccn2)c(OC)cc1N(C)CCN(C)C]

Compound 97e was prepared in the same manner as compound 97a, except that compound 96e was used instead of compound 96a. $^1$H NMR (400 MHz, CDCl$_3$): δ 9.85 (s, 1H), 9.02 (s, 1H), 8.77 (d, J=6.9 Hz, 1H), 8.32 (d, J=5.2 Hz, 1H), 7.94 (s, 1H), 7.73 (d, J=7.3 Hz, 1H), 7.39-7.21 (m, 2H), 7.10-6.84 (m, 4H), 6.76 (s, 1H), 6.50-6.45 (m, 1H), 5.76-5.74 (m, 1H), 3.86 (s, 3H), 3.12-3.06 (m, 2H), 2.75-2.72 (m, 5H), 2.55 (s, 6H); MS (ESI) (m/z): [M+H]$^+$ 486.3.

The synthesis route of compound 103 is as shown in Scheme 12:

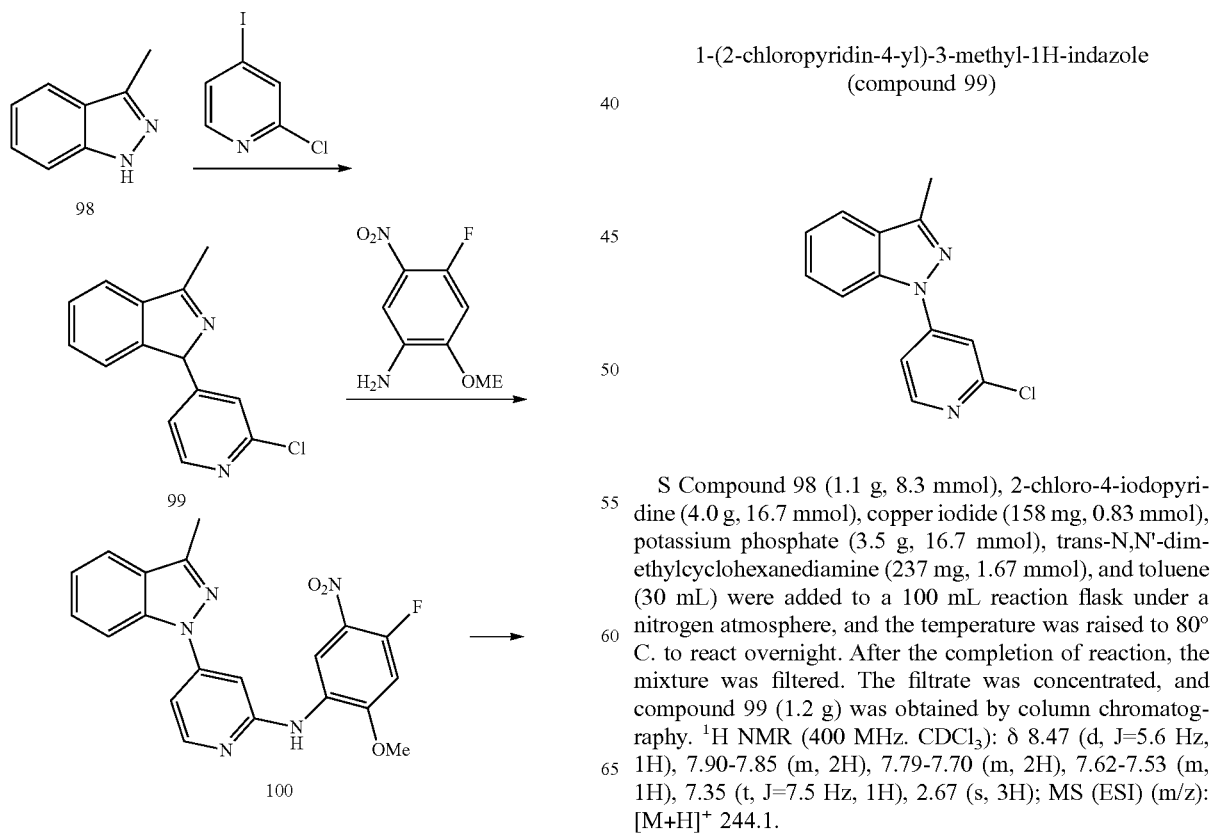

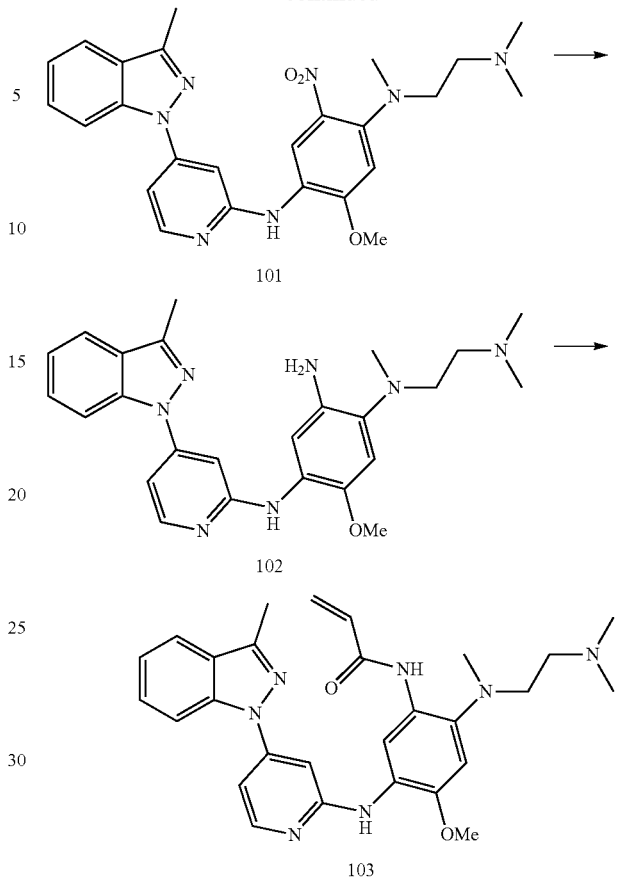

1-(2-chloropyridin-4-yl)-3-methyl-1H-indazole (compound 99)

S Compound 98 (1.1 g, 8.3 mmol), 2-chloro-4-iodopyridine (4.0 g, 16.7 mmol), copper iodide (158 mg, 0.83 mmol), potassium phosphate (3.5 g, 16.7 mmol), trans-N,N'-dimethylcyclohexanediamine (237 mg, 1.67 mmol), and toluene (30 mL) were added to a 100 mL reaction flask under a nitrogen atmosphere, and the temperature was raised to 80° C. to react overnight. After the completion of reaction, the mixture was filtered. The filtrate was concentrated, and compound 99 (1.2 g) was obtained by column chromatography. $^1$H NMR (400 MHz. CDCl$_3$): δ 8.47 (d, J=5.6 Hz, 1H), 7.90-7.85 (m, 2H), 7.79-7.70 (m, 2H), 7.62-7.53 (m, 1H), 7.35 (t, J=7.5 Hz, 1H), 2.67 (s, 3H); MS (ESI) (m/z): [M+H]$^+$ 244.1.

N-(4-fluoro-2-methoxy-5-nitrophenyl)-4-(3-methyl-H-indazol-1-yl)pyridin-2-amine (compound 100)

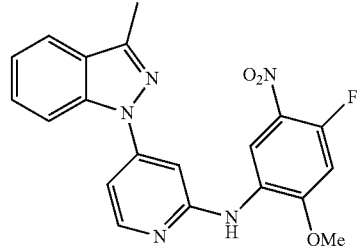 [SMILES: COc1cc(F)c([N+](=O)[O-])cc1Nc1cc(-n2nc(C)c3ccccc32)ccn1]

Compound 99 (1.2 g, 4.9 mmol), 4-fluoro-2-methoxy-5-nitroaniline (1.2 g, 6.3 mmol), palladium acetate (110 mg, 0.49 mmol), 4,5-bis(diphenylphosphino)-9,9-dimethylxanthene (566 mg, 0.98 mmol), potassium tert-butoxide (1.1 g, 9.8 mmol), and toluene (20 mL) were added to a 100 mL reaction flask under a nitrogen atmosphere, and the temperature was raised to 100° C. to react overnight. After the completion of reaction, the mixture was filtered. The filtrate was concentrated, and compound 100 (500 mg) was obtained by column chromatography. $^1$H NMR (400 MHz, CDCl$_3$): δ 9.37 (d, J=8.2 Hz, 1H), 8.42 (d, J=5.2 Hz, 1H), 7.93 (d, J=8.5 Hz, 1H), 7.77 (d, J=8.0 Hz, 1H), 7.58-7.54 (m, 1H), 7.37-7.31 (m, 2H), 7.26 (s, 1H), 7.13 (s, 1H), 6.77 (d, J=12.1 Hz, 1H), 4.05 (s, 3H), 2.68 (s, 3H); MS (ESI) (m/z): [M+H]$^+$ 394.1.

N$^1$-(2-(dimethylamino)ethyl)-5-methoxy-N$^1$-methyl-N$^4$-(4-(3-methy-H-indazol-1-yl)pyridin-2-yl)-2-nitrobenzene-1,4-diamine (compound 101)

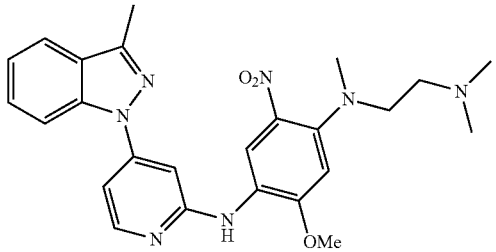 [SMILES: COc1cc(N(C)CCN(C)C)c([N+](=O)[O-])cc1Nc1cc(-n2nc(C)c3ccccc32)ccn1]

N,N-diisopropylethylamine (0.5 mL) and N,N,N'-trimethylethylenediamine (0.36 mL, 2.8 mmol) were added sequentially to a solution of compound 100 (500 rug, 1.4 mmol) in N,N-dimethylacetamide (15 mL) at room temperature. The mixture was heated to 80° C. and reacted for 2 h. After the completion of reaction, ethyl acetate and water were added. The mixture was fully stirred and filtered over celite. The organic phase was washed several times with saturated brine. After drying and concentration, compound 101 (500 mg) was obtained by column chromatography. MS (ESI) (m/z): [M+H]$^+$ 476.2.

N$^1$-(2-(dimethylamino)ethyl)-5-methoxy-N$^1$-methyl-N$^4$-(4-(3-methyl-1H-indazol-1-yl)pyri din-2-yl)benzene-1,2,4-triamine (compound 102)

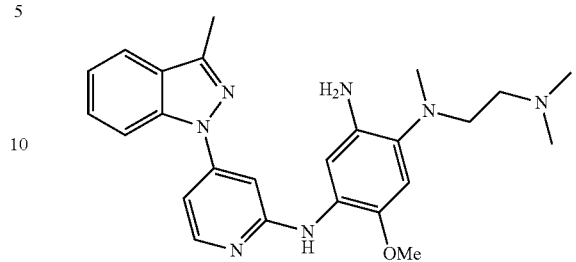

Compound 102 was prepared in the same manner as compound 96a, except that compound 101 was used instead of compound 95a. $^1$H NMR (400 MHz, CDCl$_3$): δ 8.32 (d, J=6.0 Hz, 1H), 7.87 (d, J=8.3 Hz, 1), 7.76 (d, J=8.2 Hz, 1H), 7.64 (s, 1H) 7.58-7.44 (m, 1H), 7.34-7.24 (m, 2H), 7.20 (s, 1H), 6.99 (s, 1H), 6.74 (s, 1H), 3.85 (s, 3H), 3.01 (t, J=6.6 Hz, 2H), 2.70 (s, 3H), 2.67 (s, 3H), 2.48 (m, 2H), 2.33 (s, 6H); MS (ESI) (m/z): [M+H]$^+$ 446.3.

Example 45: N-(2-((2-(dimethylamino)ethyl)(methyl)amino)-4-methoxy-5-((4-(3-methyl-1H-indazol-1-yl)pyridin-2-yl)amino)phenyl)acrylamide (compound 103)

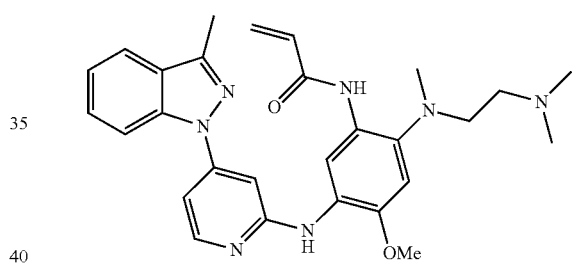

Compound 103 was prepared in the same manner as compound 97a, except that compound 102 was used instead of compound 96a. $^1$H NMR (400 MHz, CDCl$_3$) δ 10.16 (s, 1H), 9.22 (s, 1H), 8.35 (d, J=5.6 Hz, 1H), 8.11 (d, J=8.5 Hz, 11H), 7.71 (d, J=8.0 Hz, 1H), 7.48 (t, J=7.7 Hz, 1H), 7.38 (s, 1H), 7.27-7.24 (m, 2H), 7.03 (s, 1H), 6.82 (s, 1H), 6.52-6.42 (m, J=19.5 Hz, 2H), 5.75 (d, J=11.6 Hz, 1H), 3.88 (s, 3H), 2.92 (m, 2H), 2.74 (s, 3H), 2.66 (s, 3H), 2.31-2.25 (n, 8H); MS (ESI) (m/z): [M+H]$^+$ 500.3.

Biological Activity Testing

MIT cell proliferation assay is described as follows.

Tumor cell proliferation and growth inhibition analysis: H1975 (non-small-cell lung cancer cells. EGFR L858K/T790M) and A431 (human epidermal cancer cells, EGFR wild type) cells were commercially available from the ATCC cell bank. The growth medium for H1975 cells was RPMI-1640 (GIBCO, A10491-065), 10% fetal bovine serum. The growth medium for A431 cells was DMEM (GIBCO, 11995-065), 10% fetal bovine serum. The influence exerted by the compounds on the proliferation activity of tumor cells was detected by Cell Titer-Glo assay. Tumor cells were exposed to the treatment conditions for 72 h, and the cell density used in each experiment for each cell line was adjusted according to the 72 h cell growth curve. 10 concentration gradients and three-fold dilutions (0.5 nM-10 μM) were set for compounds to be tested, and 3 parallel controls were used for each concentration value.

Trypsin was used for digesting cells in the logrithmic growth phase to prepare cell suspension, which was counted by a Roche counter and appropriately diluted with complete medium to a final cell concentration of $1\sim2\times10^3$ cell/mL. 384-well plates were seeded with cells, and 22.6 μL were seeded for each well. 3 parallels were set. The plates were incubated in an incubator with 5% $CO_2$ at 37° C. overnight. The compounds were dissolved in DMSO to prepare 10 μmol/L mother liquor. Then the compounds were diluted gradiently with a BRAVO instrument, and the concentrations of compound obtained by stepwise dilution were 10 μmol/L, 3.33 μmol/L, 1.11 μmol/L, 0.37 μmol/L, 0.123 μmol/L, 0.041 μmol/L, 0.0137 μmol/L, 0.00457 μmol/L, 0.00152 μmol/L, and 0.0005 μmol/L respectively. 2 μL of compound solution was added into 18 μL of culture medium, and fully mixed. Then 2 μL of mixed solution of compound and culture medium was added into 18 μL of culture medium, and fully mixed. 2.4 μL of mixtures were added into a 384-well plates. 2.4 μL of diluted DMSO was used instead of compound solutions as 0% inhibition control (the final concentration of DMSO should be lower than 0.1% to reduce the influence caused by DMSO). After cultivation for 72 h, 24 μL of Cell Titer-Glo reagent was added. The contents were mixed on an orbital shaker for 2 min to induce cell lysis. The 384-well plates were incubated at room temperature for 10 min to stabilize the fluorescent signal value. Data was read by Infinite® M1000 PRO (TECAN), and calculated with GraphPad Prism version 5.0. GI50 value was obtained by adjustment using a non-linear regression model of dose response curves.

The testing results are shown as follows.

| compound | H1975 $GI_{50}$ (nM) | A431 $GI_{50}$ (nM) |
|---|---|---|
| Example 1 (compound 14a) | 7.3 | ~110 |
| Example 2 (compound 14b) | 168.4 | 727.7 |
| Example 3 (compound 14c) | 82.4 | 1238 |
| Example 4 (compound 14d) | 844.1 | ~63370 |
| Example 5 (compound 14e) | 31.2 | 1219 |
| Example 6 (compound 21a) | 4 | 89.1 |
| Example 7 (compound 21b) | 49 | ~1722 |
| Example 8 (compound 21c) | 26.1 | 298.9 |
| Example 9 (compound 21d) | 24.2 | >1000 |
| Example 10 (compound 21e) | 284.8 | >1000 |
| Example 11 (compound 21f) | 36 | 689.6 |
| Example 12 (compound 31a) | 6.8 | 10210 |
| Example 13 (compound 31b) | 174.7 | 1555 |
| Example 14 (compound 31c) | 1465 | ~3523 |
| Example 15 (compound 31d) | 77.5 | 5367 |
| Example 16 (compound 31e) | 2878 | 2095 |
| Example 17 (compound 31f) | 39.8 | 1302 |
| Example 18 (compound 39a) | 6.7 | 295.8 |
| Example 19 (compound 39b) | 165.6 | 1440 |
| Example 20 (compound 39c) | >1000 | >1000 |
| Example 21 (compound 39d) | 35.9 | 318.6 |
| Example 22 (compound 39e) | 184.1 | 724 |
| Example 23 (compound 39f) | 110.3 | 2440 |
| Example 24 (compound 51a) | 10.7 | 208.8 |
| Example 25 (compound 51b) | 6.5 | 85.8 |
| Example 26 (compound 51c) | 296.1 | 1127 |
| Example 27 (compound 51d) | 1096 | 2543 |
| Example 28 (compound 51e) | 260.8 | 5302 |
| Example 29 (compound 51f) | 60.3 | >1000 |
| Example 30 (compound 59) | 21.5 | 942.9 |
| Example 31 (compound 72) | 33.5 | 625.2 |
| Example 32 (compound 80a) | 9.4 | 147.1 |
| Example 33 (compound 80b) | 9.8 | 100.1 |
| Example 34 (compound 80c) | 462.3 | 2568 |
| Example 35 (compound 80d) | 1556 | 3322 |
| Example 36 (compound 80e) | 114.2 | 1115 |
| Example 37 (compound 80f) | 440.8 | 1317 |
| Example 38 (compound 85) | 8.3 | 144.2 |
| Example 39 (compound 89) | 21.2 | 15.2 |
| Example 40 (compound 97a) | 28.9 | 198.1 |
| Example 41 (compound 97b) | ~36.5 | ~800 |
| Example 42 (compound 97c) | 16.3 | 264.2 |
| Example 43 (compound 97d) | 19.1 | 266.8 |
| Example 44 (compound 97e) | 103.9 | 638.4 |
| Example 45 (compound 103) | 7.6 | 798.2 |
| AZD9291 | 2.8 | 40.1 |
| Irresa | 736.4 | 70.9 |

What is claimed is:

1. A compound represented by formula (I), or a pharmaceutically acceptable salt or a solvate thereof:

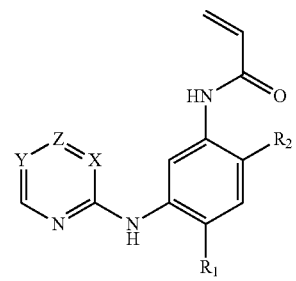

(I)

wherein
X is CH, Y is CH, Z is C—$R_a$, $R_1$ is methoxy; or X is nitrogen, Y is CH, Z is C—$R_b$, $R_1$ is methoxy or difluoromethoxy; or X is nitrogen, Y is nitrogen, Z is C—$R_c$, $R_1$ is methoxy or difluoromethoxy; or X is nitrogen, Y is nitrogen, Z is C—$R_d$, $R_1$ is difluoromethoxy;

$R_a$ is 3-methyl-1H-indazol-1-yl, 1-methyl-1H-pyrrolo[2,3-b]pyridin-3-yl, 1-methyl-1H-thieno[3,2-c]pyrazol-3-yl, 1-methyl-1H-pyrazolo[4,3-b]pyridin-3-yl, pyrazolo[1,5-a]pyrimidin-3-yl, or imidazo[1,2-a]pyridin-3-yl;

$R_b$ is benzo[d]isoxazol-3-yl, 1-methyl-1H-pyrrolo[3,2-b]pyridin-3-yl, 2,4-dimethyl-4H-thieno[3,2-b]pyrrol-6-yl, 2,5,6-trimethyl-6H-thieno[2,3-b]pyrrol-4-yl, or 1-methyl-1H-thieno[3,2-c]pyrazol-3-yl;

$R_c$ is 1H-benzo[d]imidazol-1-yl, 1H-indol-7-yl or 1-methyl-1H-indol-7-yl;

$R_d$ is 1-methyl-1H-pyrrolo[2,3-b]pyridin-3-yl; and $R_2$ is (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl, or 5-methyl-2,5-diazaspiro[3.4]oct-2-yl;

provided that the compound is not

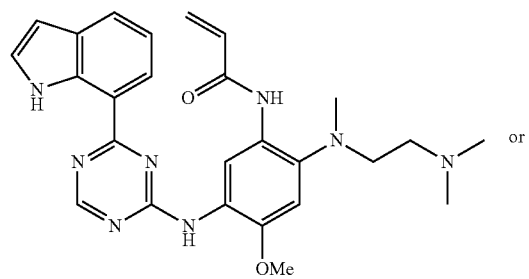

or

-continued

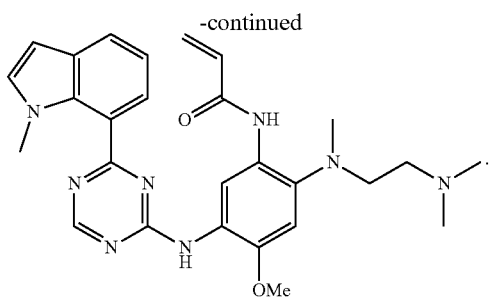

2. The compound according to claim 1, or a pharmaceutically acceptable salt or a solvate thereof, which has a structure represented by formula (II),

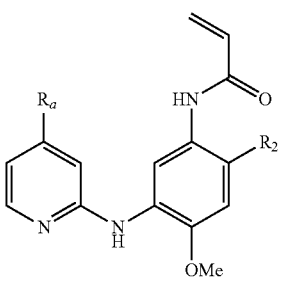

wherein
R$_a$ is 3-methyl-1H-indazol-1-yl, 1-methyl-1H-pyrrolo[2,3-b]pyridin-3-yl, 1-methyl-1H-thieno[3,2-c]pyrazol-3-yl, 1-methyl-1H-pyrazolo[4,3-b]pyridin-3-yl, pyrazolo[1,5-a]pyrimidin-3-yl, or imidazo[1,2-a]pyridin-3-yl; and
R$_2$ is (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl, or 5-methyl-2,5-diazaspiro[3.4]oct-2-yl.

3. The compound according to claim 1, or a pharmaceutically acceptable salt or a solvate thereof, which has a structure represented by formula (III),

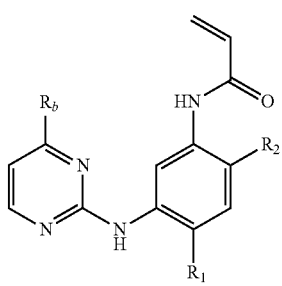

wherein
R$_b$ is benzo[d]isoxazol-3-yl, 1-methyl-1H-pyrrolo[3,2-b]pyridin-3-yl, 2,4-dimethyl-4H-thieno[3,2-b]pyrrol-6-yl, 2,5,6-trimethyl-6H-thieno[2,3-b]pyrrol-4-yl, or 1-methyl-1H-thieno[3,2-c]pyrazol-3-yl;
R$_1$ is methoxy or difluoromethoxy; and
R$_2$ is (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl, or 5-methyl-2,5-diazaspiro[3.4]oct-2-yl.

4. The compound according to claim 1, or a pharmaceutically acceptable salt or a solvate thereof, which has a structure represented by formula (IV),

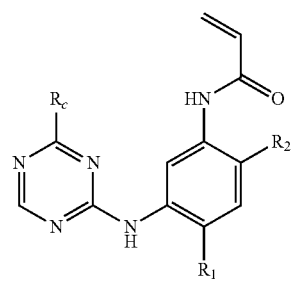

wherein
R$_c$ is 1H-benzo[d]imidazol-1-yl, 1H-indol-7-yl, or 1-methyl-1H-indol-7-yl;
R$_1$ is methoxy or difluoromethoxy; and
R$_2$ is (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl, or 5-methyl-2,5-diazaspiro[3.4]oct-2-yl.

5. The compound according to claim 1, or a pharmaceutically acceptable salt or a solvate thereof, which has a structure represented by formula (V),

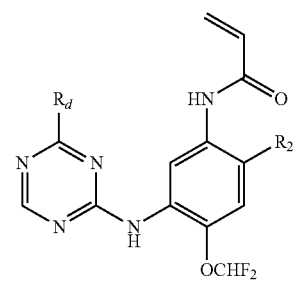

wherein
R$_d$ is 1-methyl-H-pyrrolo[2,3-b]pyridin-3-yl; and
R$_2$ is (2-(dimethylamino)ethyl)(methyl)amino, 4-methylpiperazin-1-yl, 3-(dimethylamino)azetidin-1-yl, 4-(dimethylamino)piperidin-1-yl, (S)-2-((dimethylamino)methyl)pyrrolidin-1-yl, or 5-methyl-2,5-diazaspiro[3.4]oct-2-yl.

6. The compound according to claim 3, or a pharmaceutically acceptable salt or a solvate thereof, wherein R$_b$ is benzo[d]isoxazol-3-yl, 1-methyl-1H-pyrrolo[3,2-b]pyridin-3-yl, or 1-methyl-H-thieno[3,2-c]pyrazol-3-yl.

7. The compound according to claim 4, or a pharmaceutically acceptable salt or a solvate thereof, wherein R is 1H-indol-7-yl.

8. The compound according to claim 1, or a pharmaceutically acceptable salt or a solvate thereof, wherein R$_2$ is (2-(dimethylamino)ethyl)(methyl)amino.

9. The compound according to claim 1, or a pharmaceutically acceptable salt or a solvate thereof, wherein the compound represented by the formula (I) is:
N-(5-((4-(benzo[d]isoxazol-3-yl)pyrimidin-2-yl)amino)-4-(difluoromethoxy)-2-((2-(dimethylamino)ethyl)(methyl)amino)phenyl)acrylamide, N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide, N-(4-(difluoromethoxy)-2-((2-(dimethylamino)ethyl)(methyl)amino)-5-((4-(1-methyl-1H-pyrrolo[3,2-b]pyridin-3-yl)pyrimidin-2-yl)amino)phenyl)acrylamide, N-(4-(difluoromethoxy)-2-((2-(dimethylamino)ethyl)(methyl)amino)-5-((4-(1-methyl-1H-thieno[3,2-c]pyrrol-3-yl)pyrimidin-2-yl)amino)phenyl)acrylamide, N-(5-((4-(1H-indol-7-yl)-1,3,5-triazin-2-yl)amino)-4-(difluoromethoxy)-2-((2-(dimethylamino)ethyl)(methyl)amino)phenyl)acrylamide, N-(4-(difluoromethoxy)-2-((2-(dimethylamino)ethyl)(methyl)amino)-5-((4-(1-methyl-1H-pyrrolo[2,3-b]pyridin-3-yl)-1,3,5-triazin-2-yl)amino)phenyl)acrylamide, N-(5-((4-(benzo[d]isoxazol-3-yl)pyrimidin-2-yl)amino)-2-((2-(dimethylamino)ethyl)(methyl)amino)-4-methoxyphenyl)acrylamide, or N-(2-((2-(dimethylamino)ethyl)(methyl)amino)-4-methoxy-5-((4-(1-methyl-1H-thieno[3,2-c]pyrrol-3-yl)pyrimidin-2-yl)amino)phenyl)acrylamide.

10. A pharmaceutical composition comprising the compound according to claim 1, or a pharmaceutically acceptable salt, or a solvate thereof, and a pharmaceutically acceptable diluent and/or carrier.

11. The composition of claim 10, further comprising an additional anti-tumor substance.

12. A method for producing an anti-cancer effect in a warm-blooded animal in need of such treatment, which comprises administering to the animal an effective amount of the compound according to claim 1 or a pharmaceutically acceptable salt or a solvate thereof;
wherein the anti-cancer effect is an effect against colon cancer, non-small-cell lung cancer, or skin cancer.

13. The method of claim 12, further comprising administering to the animal an additional anti-tumor substance for the simultaneous, separate or sequential production of an anti-cancer effect.

14. A method for preparing the compound according to claim 1 or a pharmaceutically acceptable salt or a solvate thereof, which comprises:
in the presence of an organic solvent, making a compound represented by the following formula (VI) or a salt thereof react with a carboxylic acid or a carboxylic acid derivatives,

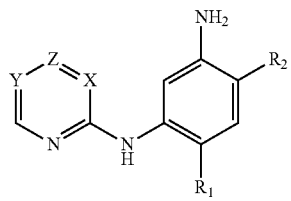

(VI)

wherein, in formula (VI), X, Y, Z, $R_1$, and $R_2$ have the same meaning as in the formula (I).

15. The method according to claim 14 wherein the organic solvent includes dichloromethane, tetrahydrofuran, N,N-dimethylformamide, or N,N-dimethylacetamide, and the carboxylic acid or carboxylic acid derivatives includes acrylic acid, acryloyl chloride or acrylic ester.

16. The method according to claim 14, wherein the compound represented by the formula (VI) is:

$N^4$-(4-(4-benzo[d]isoxazol-3-yl)pyrimidin-2-yl)-$N^1$-(2-(dimethylamino)ethyl)-5-methoxy-$N^1$-toluene-1,2,4-triamine, $N^4$-(4-(benzo[d]isoxazol-3-yl)pyrimidin-2-yl)-5-(difluoromethoxy)-$N^1$-(2-(dimethylamino)ethyl)-$N^1$-toluene-1,2,4-triamine, $N^1$-(2-(dimethylamino)ethyl)-5-methoxy-$N^1$-methyl-$N^4$-(4-(1-methyl-1H-pyrrolo[3,2-b]pyridin-3-yl)pyrimidin-2-yl)benzene-1,2,4-triamine, 5-(difluoromethoxy)-$N^1$-(2-(dimethylamino)ethyl)-$N^1$-methyl-$N^4$-(4(1-methyl-1H-pyrrolo[3,2-b]pyridin-3-yl)pyrimidin-2-yl)benzene-1,2,4-triamine, $N^1$-(2-(dimethylamino)ethyl)-5-methoxy-$N^1$-methyl-$N^4$-(4-(1-methyl-1H-thieno[3,2-c]pyrazol-3-yl)pyrimidin-2-yl)benzene-1,2,4-triamine, 5-(difluoromethoxy)-$N^1$-(2-(dimethylamino)ethyl)-$N^1$-methyl-$N^4$-(4-(1-methyl-1H-thieno[3,2-c]pyrazol-3-yl)pyrimidin-2-yl)benzene-1,2,4-triamine, $N^4$-(4-(1H-indol-7-yl)-1,3,5-triazin-2-yl)-$N^1$-(2-(dimethylamino)ethyl)-5-methoxy-$N^1$-toluene-1,2,4-triamine, $N^4$-(4-(1H-indol-7-yl)-1,3,5-triazin-2-yl)-5-(difluoromethoxy)-$N^1$-(2-(dimethylamino)ethyl)-$N^1$-toluene-1,2,4-triamine, or 5-(difluoromethoxy)-$N^1$-(2-(dimethylamino)ethyl)-$N^1$-methyl-$N^4$-(4-(1-methyl-1H-pyrrolo[2,3-b]pyridin-3-yl)-1,3,5-triazin-2-yl)benzene-1,2,4-triamine.

17. A method for treating cancer, comprising administering to a warm-blooded animal in need of such treatment an effective amount of the compound of claim 1 or a pharmaceutically acceptable salt or a solvate thereof;
wherein the cancer is colon cancer, non-small-cell lung cancer, or skin cancer.

18. The method of claim 17, wherein the animal is a human being.

19. The method of claim 18, wherein the cancer is colon cancer.

20. The method of claim 18, wherein the cancer is non-small-cell lung cancer.

21. The method of claim 18, wherein the cancer is skin cancer.

* * * * *

UNITED STATES PATENT AND TRADEMARK OFFICE
CERTIFICATE OF CORRECTION

PATENT NO. : 10,377,747 B2  
APPLICATION NO. : 15/745187  
DATED : August 13, 2019  
INVENTOR(S) : Jiaquan Wu et al.

Page 1 of 1

It is certified that error appears in the above-identified patent and that said Letters Patent is hereby corrected as shown below:

In the Claims

Column 104, Line 46: in Claim 5, delete "-H-" and insert -- -1H- -- therefor.

Column 104, Line 55: in Claim 6, delete "-H-" and insert -- -1H- -- therefor.

Column 104, Line 57: in Claim 7, delete "R" and insert -- $R_c$ -- therefor.

Column 106, Line 16: in Claim 16, delete "-methyl-$N^1$-" and insert -- -methyl-$N^4$- -- therefor.

Column 106, Line 20: in Claim 16, delete "-(4(1" and insert -- -(4-(1 -- therefor.

Signed and Sealed this  
Eighth Day of October, 2019

Andrei Iancu  
*Director of the United States Patent and Trademark Office*